US008420087B2

(12) United States Patent
Gillies et al.

(10) Patent No.: US 8,420,087 B2
(45) Date of Patent: Apr. 16, 2013

(54) INTERLEUKIN-12 TARGETED TO ONCOFOETAL FIBRONECTIN

(75) Inventors: Stephen Gillies, Carlisle, MA (US); Kin-Ming Lo, Lexington, MA (US); Yan Lan, Belmont, MA (US); Rakesh Verma, London (GB)

(73) Assignees: Antisoma Research Limited (GB); EMD Serono Research Center, Inc., Billerica, MA (US)

(*) Notice: Subject to any disclaimer, the term of this patent is extended or adjusted under 35 U.S.C. 154(b) by 1277 days.

(21) Appl. No.: 10/596,997

(22) PCT Filed: Jan. 5, 2005

(86) PCT No.: PCT/GB2005/000007
§ 371 (c)(1),
(2), (4) Date: Apr. 9, 2007

(87) PCT Pub. No.: WO2005/066348
PCT Pub. Date: Jul. 21, 2005

(65) Prior Publication Data
US 2007/0202103 A1    Aug. 30, 2007

Related U.S. Application Data

(60) Provisional application No. 60/534,307, filed on Jan. 5, 2004.

(51) Int. Cl.
A61K 39/00      (2006.01)
A61K 39/395    (2006.01)
C12P 21/08      (2006.01)
C07K 16/00      (2006.01)

(52) U.S. Cl.
USPC .................. 424/134.1; 424/141.1; 424/178.1; 424/85.2; 435/69.7; 530/387.1

(58) Field of Classification Search .................. None
See application file for complete search history.

(56) References Cited

U.S. PATENT DOCUMENTS

| | | | |
|---|---|---|---|
| 4,440,859 A | 4/1984 | Rutter et al. |
| 4,469,797 A | 9/1984 | Albarella |
| 4,530,901 A | 7/1985 | Weissmann |
| 4,582,800 A | 4/1986 | Crowl |
| 4,677,063 A | 6/1987 | Mark et al. |
| 4,678,751 A | 7/1987 | Goeddel |
| 4,704,362 A | 11/1987 | Itakura et al. |
| 4,710,463 A | 12/1987 | Murray |
| 4,757,006 A | 7/1988 | Toole, Jr. et al. |
| 4,766,075 A | 8/1988 | Goeddel et al. |
| 4,810,648 A | 3/1989 | Stalker |
| 5,019,368 A | 5/1991 | Epstein et al. |
| 5,073,627 A | 12/1991 | Curtis et al. |
| 5,199,942 A | 4/1993 | Gillies |
| 5,349,053 A | 9/1994 | Landolfi |
| 5,457,038 A | 10/1995 | Trinchieri et al. |
| 5,480,981 A | 1/1996 | Goodwin et al. |
| 5,609,846 A | 3/1997 | Goldenberg |
| 5,614,184 A | 3/1997 | Sytkowski et al. |
| 5,650,150 A | 7/1997 | Gillies |
| 5,650,492 A | 7/1997 | Gately et al. |
| 5,709,859 A | 1/1998 | Aruffo et al. |
| 5,728,552 A | 3/1998 | Fujisawa et al. |
| 5,858,347 A | 1/1999 | Bauer et al. |
| 5,891,680 A | 4/1999 | Lieschke et al. |
| 5,922,685 A | 7/1999 | Rakhmilevich et al. |
| 5,994,104 A | 11/1999 | Anderson et al. |
| 6,086,875 A | 7/2000 | Blumberg et al. |
| 6,169,070 B1 | 1/2001 | Chen et al. |
| 6,335,176 B1 | 1/2002 | Inglese et al. |
| 6,444,792 B1 | 9/2002 | Gray et al. |
| 6,485,726 B1 | 11/2002 | Blumberg et al. |
| 6,500,641 B1 | 12/2002 | Chen et al. |
| 6,551,592 B2 | 4/2003 | Thierfelder et al. |
| 6,620,413 B1 | 9/2003 | DeSauvage et al. |
| 6,750,329 B1 | 6/2004 | Rosenblum et al. |
| 6,838,260 B2 * | 1/2005 | Gillies et al. |
| 2001/0053539 A1 | 12/2001 | Lauffer et al. |
| 2002/0142374 A1 | 10/2002 | Gallo et al. |

(Continued)

FOREIGN PATENT DOCUMENTS

EP    0 239 400    9/1987
EP    0 251 744    1/1988

(Continued)

OTHER PUBLICATIONS

Mariani et al. Cancer, 80(12 Suppl):2484-2489, 1997.*
Rudikoff et al. Proc. Natl. Acad. Sci. USA, 79(6):1979-1983, Mar. 1982.*
Schier et al. Journal of Molecular Biology, 263:551-567, 1996.*
International Search Report in International Application No. PCT/GB2005/000007, 8 pages, mailed Sep. 12, 2005.
Written Opinion of the International Searching Authority in International Application No. PCT/GB2005/000007, 11 pages, mailed Sep. 12, 2005.
International Preliminary Report on Patentability in International Application No. PCT/GB2005/000007, 19 pages, date of completion of report: Apr. 18, 2006.
Castellani, P., et al., "Differentiation between High- and Low-Grade Astrocytoma Using a Human Recombinant Anti body to the Extra Domain—B of Fibronectin," *American Journal of Pathology*, 161(5):1695-1700 (Nov. 2002).

(Continued)

*Primary Examiner* — Elly-Gerald Stoica
(74) *Attorney, Agent, or Firm* — Hamilton, Brook, Smith & Reynolds, P.C.

(57)    ABSTRACT

The invention provides a compound comprising a target specific portion and an effector portion wherein the target specific portion comprises or consists of a monoclonal antibody having specificity for oncofoetal fibronectin, or a fragment or variant thereof which retains the antigen binding specificity of the parent monoclonal antibody and the effector portion comprises or consists of interleukin-12, or a functional fragment or variant thereof, characterized in the monoclonal antibody having specificity for oncofoetal fibronectin binds to a region of oncofoetal fibronectin other than the ED-B region. The invention further provides nucleic acids encoding the compounds of the invention, and the use of such compounds in medicine, e.g. in the treatment of cancer.

10 Claims, 12 Drawing Sheets

U.S. PATENT DOCUMENTS

| | | |
|---|---|---|
| 2002/0192222 A1 | 12/2002 | Blumberg et al. |
| 2003/0012789 A1 | 1/2003 | Blumberg et al. |
| 2004/0013640 A1 | 1/2004 | Zardi et al. |

FOREIGN PATENT DOCUMENTS

| | | |
|---|---|---|
| EP | 0 258 067 | 3/1988 |
| EP | 0 344 134 | 11/1989 |
| EP | 0 350 230 | 1/1990 |
| EP | 0 375 562 | 6/1990 |
| EP | 0 396 387 | 11/1990 |
| EP | 0 433 827 | 6/1991 |
| EP | 0 706 799 | 4/1996 |
| EP | 0 790 309 | 8/1997 |
| WO | WO 88/00052 | 1/1988 |
| WO | WO 89/02922 | 4/1989 |
| WO | WO 90/01063 | 2/1990 |
| WO | WO 91/00360 | 1/1991 |
| WO | WO 91/14438 | 10/1991 |
| WO | WO 95/21258 | 8/1995 |
| WO | WO 95/31483 | 11/1995 |
| WO | WO 96/04388 | 2/1996 |
| WO | WO 96/18412 | 6/1996 |
| WO | WO 96/40792 | 12/1996 |
| WO | WO 97/00319 | 1/1997 |
| WO | WO 97/20062 | 6/1997 |
| WO | WO 97/24440 | 7/1997 |
| WO | WO 97/33617 | 9/1997 |
| WO | WO 97/33619 | 9/1997 |
| WO | WO 97/43316 | 11/1997 |
| WO | WO 97/45544 A1 | 12/1997 |
| WO | WO 98/00127 | 1/1998 |
| WO | WO 98/28427 | 7/1998 |
| WO | WO 98/30706 | 7/1998 |
| WO | WO 98/46257 | 10/1998 |
| WO | WO 99/02709 | 1/1999 |
| WO | WO 99/29732 | 6/1999 |
| WO | WO 99/43713 | 9/1999 |
| WO | WO 99/52562 | 10/1999 |
| WO | WO 99/53958 | 10/1999 |
| WO | WO 00/11033 | 3/2000 |
| WO | WO 00/40615 | 7/2000 |
| WO | WO 00/69913 | 11/2000 |
| WO | WO 01/07081 | 2/2001 |
| WO | WO 01/36489 | 5/2001 |
| WO | WO 01/58957 | 8/2001 |
| WO | WO 02/02143 | 1/2002 |
| WO | WO 02/066514 | 8/2002 |
| WO | WO 02/072605 | 9/2002 |
| WO | WO 02079232 A2 * | 10/2002 |
| WO | WO 02/090566 | 11/2002 |
| WO | WO 03/015697 | 2/2003 |
| WO | WO 03/048334 | 6/2003 |
| WO | WO 03/076469 | 9/2003 |
| WO | WO 03/077834 | 9/2003 |
| WO | WO 03/093478 | 11/2003 |

OTHER PUBLICATIONS

Courtenay-Luck, N.S. and Jones, D., "Immunotherapeutic Antibody Fusion Proteins." In *Recombinant Antibodies for Immunotherapy*, Cambridge University Press., pp. 190-200 (2009).

Afonso, et al., "The adjuvant effect of interleukin-12 in a vaccine against Leishmania major", *Science*, 263(5144):235-7 (1994).

Ansell, et al., "Phase 1 study of interleukin-12 in combination with rituximab in patients with B-cell non-Hodgkin lymphoma", *Blood*, 99(1):67-74 (2002).

Barbulescu, et al., "IL-12 and IL-18 differentially regulate the transcriptional activity of the human IFN-gamma promoter in primary CD4+ T lymphocytes", *J. Immunol.*, 160(8):3642-7 (1998).

Beggs, "Transformation of yeast by a replicating hybrid plasmid", *Nature*, 275(5676):104-9 (1978).

Berent, et al., "Comparison of oligonucleotide and long DNA fragments as probes in DNA and RNA dot, southern, northern, colony and plaque hybridizations", *Biotechniques*, 3:208-220 (1985).

Better, et al., "*Escherichia coli* secretion of an active chimeric antibody fragment", *Science*, 240(4855):1041-3 (1988).

Bird, et al., "Single-chain antigen-binding proteins", *Science*, 242(4877):423-6 (1988).

Bitonti, et al., "Transepithelial absorption of an erythropoietin-Fc fusion protein after delivery to the central airways", *Respiratory Drug Delivery*, 8:308-312 (2002).

Boshart, et al., "A very strong enhancer is located upstream of an immediate early gene of human cytomegalovirus", *Cell*, 41(2):521-30 (1985).

Carnemolla, et al., "A tumor-associated fibronectin isoform generated by alternative splicing of messenger RNA precursors", *J. Cell Biol.*, 108(3):1139-1148 (1989).

Carnemolla, et al., "The inclusion of the type III repeat ED-B in the fibronectin molecule generates conformational modifications that unmask a cryptic sequence", *J. Biol. Chem.*, 267(34):24689-92 (1992).

Chan, "Induction of interferon gamma production by natural killer cell stimulatory factor: characterization of the responder cells and synergy with other inducers", *J. Exp. Med.*, 173(4):869-79 (1991).

Chen, et al., "Eradication of murine bladder carcinoma by intratumor injection of a bicistronic adenoviral vector carrying cDNAs for the IL-12 heterodimer and its inhibition by the IL-12 p40 subunit homodimer", *J. Immunol.*, 159(1):351-9 (1997).

Cohen, et al., "Nonchromosomal antibiotic resistance in bacteria: genetic transformation of *Escherichia coli* by R-factor DNA", *Proc. Natl. Acad. Sci. U.S.A.*, 69(8):2110-4 (1972).

Colombo, et al., "Amount of interleukin 12 available at the tumor site is critical for tumor regression", *Cancer Res.*, 56(11):2531-4 (1996).

D'Andrea, et al., "Production of natural killer cell stimulatory factor (interleukin 12) by peripheral blood mononuclear cells", *J. Exp. Med.*, 176(5):1387-98 (1992).

Desai, et al., "IL-12 receptor. II. Distribution and regulation of receptor expression", *J. Immunol.*, 148(10):3125-32 (1992).

Dickerson, et al., Proceedings of the American Association for Cancer Research Annual Meeting No. 41, p. 798, abstract No. 5074 (2000).

Doran, et al., "Expression of ED-B fibronectin in renal carcinoma and metastatic melanoma and targeted therapy with AS1409, a potent immunocytokine", Abstract presentation $5^{th}$ *Int. Congress on Targeted Therapies in Cancer*, NY (2006).

Emtage, et al., "Generating potent Th1/Tc1 T cell adoptive immunotherapy doses using human IL-12: Harnessing the immunomodulatory potential of IL-12 without the in vivo-associated toxicity", *J. Immunother.*, 26(2):97-106 (2003).

Ffrench-Constant, et al., "Reappearance of an embryonic pattern of fibronectin splicing during wound healing in the adult rat", *J. Cell Biol.*, 109(2):903-14 (1989).

Gately, et al., "The interleukin-12/interleukin-12-receptor system: role in normal and pathologic immune responses", *Annu. Rev. Immunol.*, 16:495-521 (1998).

Gillessen, et al., Mouse interleukin-12 (IL-12) p40 homodimer: a potent IL-12 antagonist, *Eur. J. Immunol.*, 25(1):200-6 (1995).

Gillies, et al., "Antibody-IL-12 fusion proteins are effective in SCID mouse models of prostate and colon carcinoma metastases", *J. Immunol.*, 160(12):6195-203 (1998).

Gillies, et al., "Improved circulating half-life and efficacy of an antibody-interleukin 2 immunocytokine based on reduced intracellular proteolysis", *Clin. Cancer Res.*, 8(1):210-6 (2002).

Gollob, et al., "Phase I trial of twice-weekly intravenous interleukin 12 in patients with metastatic renal cell cancer or malignant melanoma: ability to maintain IFN-gamma induction is associated with clinical response", *Clin. Cancer Res.*, 6(5):1678-92 (2000).

Gubler and Presky, "Molecular biology of interleukin-12 receptors", *Ann. N.Y. Acad. Sci.*, 795:36-40 (1996).

Halin, et al., "Enhancement of the antitumor activity of interleukin-12 by targeted delivery to neovasculature", *Nat. Biotechnol.*, 20(3):264-9 (2002).

Halin, "Synergistic therapeutic effects of a tumor targeting antibody fragment, fused to interleukin 12 and to tumor necrosis factor alpha", *Cancer Res.*, 63(12):3202-10 (2003).

Hashimoto, et al., "Differential antitumor effects of administration of recombinant IL-18 or recombinant IL-12 are mediated primarily by Fas-Fas ligand- and perforin-induced tumor apoptosis, respectively", *J. Immunol.*, 163(2):583-9 (1999).

Heinzel, et al., "In vivo production and function of IL-12 p40 homodimers", *J. Immunol.*, 158(9):4381-8 (1997).

Heinzerling, et al., "Tumor regression of human and murine melanoma after intratumoral injection of IL-12-encoding plasmid DNA in mice", *Exp. Dermatol.*, 11(3):232-40 (2002).

Hoogenboom, et al, "Construction and expression of antibody-tumor necrosis factor fusion proteins", *Mol. Immunol.*, 28(9):1027-37 (1991).

Hoogenboom, et al., "Targeting of tumor necrosis factor to tumor cells: secretion by myeloma cells of a genetically engineered antibody-tumor necrosis factor hybrid molecule", *Biochim. Biophys. Acta.*, 1096(4):345-54 (1991).

Huang, et al., "Tumor infarction in mice by antibody-directed targeting of tissue factor to tumor vasculature", *Science*, 275(5299):547-50 (1997).

Huston, et al., "Protein engineering of antibody binding sites: recovery of specific activity in an anti-digoxin single-chain Fv analogue produced in Escherichia coli", *Proc. Natl. Acad. Sci. U.S.A.*, 85(16):5879-83 (1988).

Iwasaki, et al., "A critical role for IL-12 in CCR5 induction on T cell receptor-triggered mouse CD4(+) and CD8(+) T cells", *Eur. J. Immunol.*, 31(8):2411-20 (2001).

Jones, et al., "Replacing the complementarity-determining regions in a human antibody with those from a mouse", *Nature*, 321(6069):522-5 (1986).

Jones, et al., "The development of a modified human IFN-alpha2b linked to the Fc portion of human IgG1 as a novel potential therapeutic for the treatment of hepatitis C virus infection", *J. Interferon Cytokine Res.*, 24(9):560-72 (2004).

Jones, et al., "Production of an IgG1-IL12 fusion protein", presentation at *Optimizing Cell Culture Development* (2006).

Kang, et al., "Interleukin 12 gene therapy of cancer by peritumoral injection of transduced autologous fibroblasts: outcome of a phase I study", *Hum. Gene Ther.*, 12(6):671-84 (2001).

Kim, "An ovalbumin-IL-12 fusion protein is more effective than ovalbumin plus free recombinant IL-12 in inducing a T helper cell type 1-dominated immune response and inhibiting antigen-specific IgE production", *J. Immunol.*, 158(9):4137-44 (1997).

King, et al., "Phase I clinical trial of the immunocytokine EMD 273063 in melanoma patients", *J. Clin. Oncol.*, 22(22):4463-73 (2004).

Ko, et al., "Safety, pharmacokinetics, and biological pharmacodynamics of the immunocytokine EMD 273066 (huKS-IL2): results of a phase I trial in patients with prostate cancer", *J. Immunother.*, 27(3):232-9 (2004).

Kozak, "Point mutations close to the AUG initiator codon affect the efficiency of translation of rat preproinsulin in vivo", *Nature*, 308(5956):241-6 (1984).

Ladell, et al., "A combination of plasmid DNAs encoding murine fetal liver kinase 1 extracellular domain, murine interleukin-12, and murine interferon-gamma inducible protein-10 leads to tumor regression and survival in melanoma-bearing mice", *J. Mol. Med.*, 81(4):271-8 (2003).

Leberthon, et al., "Enhanced tumor uptake of macromolecules induced by a novel vasoactive interleukin 2 immunoconjugate", *Cancer Res.*, 51(10):2694-8 (1991).

Li, et al., "Regression of tumor growth and induction of long-term antitumor memory by interleukin 12 electro-gene therapy", *J. Natl. Cancer Inst.*, 94(10):762-8 (2002).

Li, et al. "Candidate genes associated with tumor regression mediated by intratumoral IL-12 electroporation gene therapy", *Mol. Ther.*, 9(3):347-54 (2004).

Lieschke, et al., "Bioactive murine and human interleukin-12 fusion proteins which retain antitumor activity in vivo", *Nat. Biotechnol.*, 15(1):35-40 (1997).

Linsley, et al., "CTLA-4 is a second receptor for the B cell activation antigen B7", *J. Exp. Med.*, 174(3):561-9 (1991).

Liu, et al., "Hormone conjugated with antibody to CD3 mediates cytotoxic T cell lysis of human melanoma cells", *Science*, 239(4838):395-8 (1988).

Lo, et al., "High level expression and secretion of Fc-X fusion proteins in mammalian cells", *Protein Eng.*, 11(6):495-500 (1998).

Lo, et al., "Engineering a pharmacologically superior form of leptin for the treatment of obesity", *Protein Eng. Des. Sel.*, 18(1):1-10 (2005).

Lo, et al., "Targeted delivery of IL12 via a pan-tumor-specific antibody" (2005).

Lo, et al., "huBC1-IL12, an immunocytokine which targets EDB-containing oncofetal fibronectin in tumors and tumor vasculature, shows potent anti-tumor activity in human tumor models", *Cancer Immunol. Immunother.*, 56(4):447-57 (2007).

Lode, et al., "Targeted interleukin-2 therapy for spontaneous neuroblastoma metastases to bone marrow", *J. Natl. Cancer Inst.*, 89(21):1586-94 (1997).

Lode, et al., "Immunocytokines: a promising approach to cancer immunotherapy", *Pharmacol. Ther.*, 80(3):277-92 (1998).

Lode, et al., "Natural killer cell-mediated eradication of neuroblastoma metastases to bone marrow by targeted interleukin-2 therapy", *Blood*, 91(5):1706-15 (1998).

Lode, et al., "Gene therapy with a single chain interleukin 12 fusion protein induces T cell-dependent protective immunity in a syngeneic model of murine neuroblastoma", *Proc. Natl. Acad. Sci. U.S.A.*, 95(5):2475-80 (1998).

Lode, et al., "Synergy between an antiangiogenic integrin alphav antagonist and an antibody-cytokine fusion protein eradicates spontaneous tumor metastases", *Proc. Natl. Acad. Sci. U.S.A.*, 96(4):1591-6 (1999).

Lode, et al., "Tumor-targeted IL-2 amplifies T cell-mediated immune response induced by gene therapy with single-chain IL-12", *Proc. Natl. Acad. Sci. U.S.A.*, 96(15):8591-6 (1999).

Lode, et al., "Amplification of T cell-mediated immune responses by antibody-cytokine fusion proteins", *Immunol. Invest.*, 29(2):117-20 (2000).

Lode, et al., "Melanoma immunotherapy by targeted IL-2 depends on CD4(+) T-cell help mediated by CD40/CD40L interaction", *J. Clin. Invest.*, 105(11):1623-30 (2000).

Lode, et al., "What to do with targeted IL-2", *Drugs Today (Barc)*, 36(5):321-36 (2000).

Lotze, et al., "Cytokine gene therapy of cancer using interleukin-12: murine and clinical trials", *Ann. N.Y. Acad. Sci.*, 795:440-54 (1996).

Maghazachi, et al., "Interferon-inducible protein-10 and lymphotactin induce the chemotaxis and mobilization of intracellular calcium in natural killer cells through pertussis toxin-sensitive and -insensitive heterotrimeric G-proteins", *FASEB J.*, 11(10):765-74 (1997).

Majewski, et al., "Interleukin-12 inhibits angiogenesis induced by human tumor cell lines in vivo", *J. Invest. Dermatol.*, 106(5):1114-8 (1996).

Mandpe, et al., "Cure of an established nonimmunogenic tumor, SCC VII, with a novel interleukin 12-based immunotherapy regimen in C3H mice", *Arch. Otolaryngol. Head Neck Surg.*, 129(7):786-92 (2003).

Mariani, et al., "Tumor targeting potential of the monoclonal antibody BC-1 against oncofetal fibronectin in nude mice bearing human tumor implants", *Cancer*, 80(12 Suppl):2378-84 (1997).

Mark, et al., "Expression and characterization of hepatocyte growth factor receptor-IgG fusion proteins. Effects of mutations in the potential proteolytic cleavage site on processing and ligand binding", *J. Biol. Chem.*, 267(36):26166-71 (1992).

Martinotti, et al., "CD4 T cells inhibit in vivo the CD8-mediated immune response against murine colon carcinoma cells transduced with interleukin-12 genes", *Eur. J. Immunol.*, 25(1):137-46 (1995).

Masiero, et al., "New anti-angiogenesis agents: review of the clinical experience with carboxyamido-triazole (CAI), thalidomide, TNP-470 and interleukin-12", *Angiogenesis*, 1(1):23-35 (1997).

Mazzolini, et al., "Regression of colon cancer and induction of antitumor immunity by intratumoral injection of adenovirus expressing interleukin-12", *Cancer Gene Ther.*, 6(6):514-22 (1999).

Mehrotra, et al., "Effects of IL-12 on the generation of cytotoxic activity in human CD8+ T lymphocytes", *J. Immunol.*, 151(5):2444-52 (1993).

Midulla, et al., "Source of oncofetal ED-B-containing fibronectin: implications of production by both tumor and endothelial cells", *Cancer Res.*, 60(1):164-9 (2000).

Morrison, et al., "Chimeric human antibody molecules: mouse antigen-binding domains with human constant region domains", *Proc. Natl. Acad. Sci. U.S.A.*, 81(21):6851-5 (1984).

Mosmann, et al., "TH1 and TH2 cells: different patterns of lymphokine secretion lead to different functional properties", *Annu. Rev. Immunol.*, 7:145-73 (1989).

Mullins, et al., "Interleukin-12 overcomes paclitaxel-mediated suppression of T-cell proliferation", *Immunopharmacol. Immunotoxicol.*, 20(4):473-92 (1998).

Naramura, et al., "Mechanisms of cellular cytotoxicity mediated by a recombinant antibody-IL2 fusion protein against human melanoma cells", *Immunol. Lett.*, 39(1):91-9 (1993).

Niethammer, et al., "Targeted interleukin 2 therapy enhances protective immunity induced by an autologous oral DNA vaccine against murine melanoma", *Cancer Res.*, 61(16):6178-84 (2001).

O'Sullivan, et al., "Comparison of two methods of preparing enzyme-antibody conjugates: application of these conjugates for enzyme immunoassay", *Anal. Biochem.*, 100(1):100-8 (1979).

Palucka, et al., "Dendritic cells as the terminal stage of monocyte differentiation", *J. Immunol.*, 160(9):4587-95 (1998).

Pancook, et al., "Eradication of established hepatic human neuroblastoma metastases in mice with severe combined immunodeficiency by antibody-targeted interleukin-2", *Cancer Immunol. Immunother.*, 42(2):88-92 (1996).

Parihar, et al., "IL-12 enhances the natural killer cell cytokine response to Ab-coated tumor cells", *J. Clin. Invest.*, 110(7):983-92 (2002).

Parihar, et al., "A phase I study of interleukin 12 with trastuzumab in patients with human epidermal growth factor receptor-2-overexpressing malignancies: analysis of sustained interferon gamma production in a subset of patients", *Clin. Cancer Res.*, 10(15):5027-37 (2004).

Park, et al., "CD28 costimulation is required not only to induce IL-12 receptor but also to render janus kinases/STAT4 responsive to IL-12 stimulation in TCR-triggered T cells", *Eur. J. Immunol.*, 31(5):1456-64 (2001).

Pedley, et al., "Enhancement of antibody-directed enzyme prodrug therapy in colorectal xenografts by an antivascular agent", *Cancer Res.*, 59(16):3998-4003 (1999).

Peng, et al., "Mechanism of antitumor activity of a single-chain interleukin-12 IgG3 antibody fusion protein (mscIL-12.her2.IgG3)", *J. Interferon Cytokine Res.*, 21(9):709-20 (2001).

Perez, et al., "Specific targeting of human peripheral blood T cells by heteroaggregates containing anti-T3 crosslinked to anti-target cell antibodies", *J. Exp. Med.*, 163(1):166-78 (1986).

Perussia, et al., "Natural killer (NK) cell stimulatory factor or IL-12 has differential effects on the proliferation of TCR-alpha beta+, TCR-gamma delta+ T lymphocytes, and NK cells", *J. Immunol.*, 149(11):3495-502 (1992).

Portielje, et al., "Subcutaneous injection of interleukin 12 induces systemic inflammatory responses in humans: implications for the use of IL-12 as vaccine adjuvant", *Cancer Immunol. Immunother.*, 54(1):37-43 (2005).

Putzer, et al., "Interleukin 12 and B7-1 costimulatory molecule expressed by an adenovirus vector act synergistically to facilitate tumor regression", *Proc. Natl. Acad. Sci. U.S.A.*, 94(20):10889-94 (1997).

Rakhmilevich, et al., "Treatment of experimental breast cancer using interleukin-12 gene therapy combined with anti-vascular endothelial growth factor receptor-2 antibody", *Mol. Cancer Ther.*, 3(8):969-76 (2004).

Reisfeld, et al., "Antibody-interleukin 2 fusion proteins: a new approach to cancer therapy", *J. Clin. Lab Anal.*, 10(3):160-6 (1996).

Reisfeld, et al., "Involvement of B lymphocytes in the growth inhibition of human pulmonary melanoma metastases in athymic nu/nu mice by an antibody-lymphotoxin fusion protein", *Cancer Res.*, 56(8):1707-12 (1996).

Reisfeld, et al., "Recombinant antibody fusion proteins for cancer immunotherapy", *Curr. Top. Microbiol. Immunol.*, 213 (Pt 3):27-53 (1996).

Reisfeld, et al., "Immunocytokines: a new approach to immunotherapy of melanoma", *Melanoma Res.*, 7 Suppl 2:S99-106 (1997).

Riechmann, et al., "Reshaping human antibodies for therapy", *Nature*, 332(6162):323-7 (1988).

Rosenberg, "Immunotherapy of cancer using interleukin 2: current status and future prospects", *Immunol. Today*, 9(2):58-62 (1988).

Ruehlmann, et al. "MIG (CXCL9) chemokine gene therapy combines with antibody-cytokine fusion protein to suppress growth and dissemination of murine colon carcinoma", *Cancer Res.*, 61(23):8498-503 (2001).

Sabzevari, et al., "A recombinant antibody-interleukin 2 fusion protein suppresses growth of hepatic human neuroblastoma metastases in severe combined immunodeficiency mice", *Proc. Natl. Acad. Sci. U.S.A.*, 91(20):9626-30 (1994).

Saiki, et al., "Primer-directed enzymatic amplification of DNA with a thermostable DNA polymerase", *Science*, 239(4839):487-91 (1988).

Sambrook, et al., Molecular Cloning, A Laboratory Manual, pp. 1.74-1.84 (1989).

Savage, et al., "A recombinant single chain antibody interleukin-2 fusion protein", *Br. J. Cancer*, 67(2):304-10 (1993).

Schnee, et al, "Construction and expression of a recombinant antibody-targeted plasminogen activator", *Proc. Natl. Acad. Sci. U.S.A.*, 84(19):6904-8 (1987).

Schoenhaut, et al., "Cloning and expression of murine IL-12", *J. Immunol.*, 148(11):3433-40 (1992).

Senter, et al., "Anti-tumor effects of antibody-alkaline phosphatase conjugates in combination with etoposide phosphate", *Proc. Natl. Acad. Sci. U.S.A.*, 85(13):4842-6 (1988).

Shin, et al., "Expression and characterization of an antibody binding specificity joined to insulin-like growth factor 1: potential applications for cellular targeting", *Proc. Natl. Acad. Sci. U.S.A.*, 87(14):5322-6 (1990).

Skerra, et al., "Assembly of a functional immunoglobulin Fv fragment in *Escherichia coli*", *Science*, 240(4855):1038-41 (1988).

Southern, "Detection of specific sequences among DNA fragments separated by gel electrophoresis", *J. Mol. Biol.*, 98(3):503-17 (1975).

Takahara, et al., "The ompA signal peptide directed secretion of *Staphylococcal* nuclease A by *Escherichia coli*", *J. Biol. Chem.*, 260(5):2670-4 (1985).

Thorpe, et al., "The first international conference on vascular targeting: meeting overview", *Cancer Res.*, 63(5):1144-7 (2003).

Thurner, et al., "Generation of large numbers of fully mature and stable dendritic cells from leukapheresis products for clinical application", *J. Immunol. Methods*, 223(1):1-15 (1999).

Till, et al., "An assay that predicts the ability of monoclonal antibodies to form potent ricin A chain-containing immunotoxins", *Cancer Res.*, 48(5):1119-23 (1988).

Till, et al., "HIV-infected cells are killed by rCD4-ricin A chain", *Science*, 242(4882):1166-8 (1988).

Trinchieri, "Interleukin-12: a cytokine produced by antigen-presenting cells with immunoregulatory functions in the generation of T-helper cells type 1 and cytotoxic lymphocytes", *Blood*, 84(12):4008-27 (1994).

Van Herpen, et al., "Intratumoral recombinant human interleukin-12 administration in head and neck squamous cell carcinoma patients modifies locoregional lymph node architecture and induces natural killer cell infiltration in the primary tumor", *Clin. Cancer Res.*, 11(5):1899-909 (2005).

Van Vliet, et al., "Distribution of fibronectin isoforms in human renal disease", *J. Pathol.*, 193(2):256-62 (2001).

Verhoeyen, et al., "Reshaping human antibodies: grafting an antilysozyme activity", *Science*, 239(4847):1534-6 (1988).

Verma, et al., "Targeted delivery of IL12 via an antibody for tumor and tmoral angiogenesis" (2006).

Viti, et al., "Increased binding affinity and valence of recombinant antibody fragments lead to improved targeting of tumoral angiogenesis", *Cancer Res.*, 59(2):347-52 (1999).

Vogel, et al., "Direct binding of IL-12 to human and murine B lymphocytes", *Int. Immunol.*, 8(12):1955-62 (1996).

Wadler, et al., "A phase II trial of interleukin-12 in patients with advanced cervical cancer: clinical and immunologic correlates. Eastern Cooperative Oncology Group study E1E96", *Gynecol. Oncol.*, 92(3):957-64 (2004).

Ward, et al., "Binding activities of a repertoire of single immunoglobulin variable domains secreted from *Escherichia coli*", *Nature*, 341(6242):544-6 (1989).

Wigginton, et al., Complete regression of established spontaneous mammary carcinoma and the therapeutic prevention of genetically programmed neoplastic transition by IL-12/pulse IL-2: induction of local T cell infiltration, Fas/Fas ligand gene expression, and mammary epithelial apoptosis, J. Immunol. Jan. 15, 2001;166(2):1156-68.

Williams, et al., "Production of antibody-tagged enzymes by myeloma cells: application to DNA polymerase I Klenow fragment", *Gene*, 43(3):319-24 (1986).

Winter and Milstein, "Man-made antibodies", *Nature*, 349(6307):293-9 (1991).

Wooley, et al., "Influence of a recombinant human soluble tumor necrosis factor receptor FC fusion protein on type II collagen-induced arthritis in mice", *J. Immunol.*, 151(11):6602-7 (1993).

Xiang, et al., "Elimination of established murine colon carcinoma metastases by antibody-interleukin 2 fusion protein therapy", *Cancer Res.*, 57(21):4948-55 (1997).

Yamazaki, et al., "Effective gene therapy for medullary thyroid carcinoma using recombinant adenovirus inducing tumor-specific expression of interleukin-12", *Gene Ther.*, 9(1):64-74 (2002).

Young, et al., "Thermal stabilization of a single-chain Fv antibody fragment by introduction of a disulphide bond", *FEBS Lett.*, 377(2):135-9 (1995).

Zagozdzon, et al., "Potentiation of antitumor effects of IL-12 in combination with paclitaxel in murine melanoma model in vivo", *Int. J. Mol. Med.*, 4(6):645-8 (1999).

Zheng, et al., "Administration of noncytolytic IL-10/Fc in murine models of lipopolysaccharide-induced septic shock and allogeneic islet transplantation", *J. Immunol.*, 154(10):5590-600 (1995).

Zhu, et al., "Inhibition of tumor growth and metastasis by targeting tumor-associated angiogenesis with antagonists to the receptors of vascular endothelial growth factor", *Invest. New Drugs*, 17(3):195-212 (1999).

\* cited by examiner

INTERLEUKIN-12 TARGETED TO ONCOFOETAL FIBRONECTIN

This application is a 371 application of PCT/GB2005/000007 filed on Jan. 5, 2005, which claims priority to U.S. Ser. No. 60/534,307 filed Jan. 5, 2004.

The present invention relates to compounds for use in the treatment of cancer. In particular, the invention provides fusion proteins that include an antibody portion directed against an antigen specific to tumour neovasculature fused to interleukin-12. Preferred fusion proteins of the invention bind particularly tightly to the target antigen and are useful for treating solid tumours.

BACKGROUND

Treatment of cancer with targeted fusion proteins has shown much promise, but many problems remain. For example, antibody-targeted cytokines have shown much promise in the treatment of cancer in animal models and in some human studies, but the optimal choice of antibody/antigen, cytokine, and antibody effector function remains to be determined. For example, Gillies (U.S. Pat. No. 5,650,150) described the general usefulness of cytokine fusions to complete antibodies, and the specific usefulness of antibody-IL2 fusion proteins.

Interleukin-12 (IL-12) is a particularly attractive cytokine for targeted immune therapy, because IL-12 stimulates a Th1 immune response, which is most effective in attacking tumour cells. IL-12 is quite toxic when administered systemically, consequently it is particularly important to direct its activity to a tumour site. Gillies et al. (WO 99/29732) described the usefulness of fusions of IL-12 to antibodies and also described particular techniques needed to express IL-12 fusion proteins, relating to the fact that IL-12 is a two-subunit cytokine in which one of the subunits can homodimerise. Halin et al., 2002, *Nature Biotechnology* 20:264-269 described a fusion protein consisting of a single-chain IL-12 moiety fused to a single-chain Fv (sFv) with the variable domains of L19, an antibody that binds to tumour-specific neovasculature. This latter molecule lacks the Fc region of the antibody and thus lacks all effector functions.

Even when IL-12 is fused to a targeting moiety, there is a period after the fusion protein is administered when the protein drug circulates systemically. During this period and before the drug accumulates in the tumour and disappears from the rest of the system, secondary cytokines are induced and damage results.

Hence, there is a need for improved means of delivering IL-12 to a tumour site within a patient.

SUMMARY OF THE INVENTION

A first aspect of the invention provides a compound comprising a target specific portion and an effector portion wherein the target specific portion comprises or consists of a monoclonal antibody having specificity for oncofoetal fibronectin, or a fragment or variant thereof which retains the binding specificity for oncofoetal fibronectin of the parent monoclonal antibody and the effector portion comprises or consists of interleukin-12, or a functional fragment or variant thereof.

A characterising feature of the compounds of the invention is that the monoclonal antibody having specificity for oncofoetal fibronectin binds to a region of oncofoetal fibronectin other than the extra-domain B (ED-B) region. The ED-B region of fibronectin is a domain which, by alternative splicing of the primary RNA transcript, is either present or omitted in fibronectin molecules of the extracellular matrix (see below). Thus, the monoclonal antibody having specificity for oncofoetal fibronectin does not bind to the ED-B region (ED-B domain), although it binds to a splice variant of fibronectin (termed 'oncofoetal fibronectin') which comprises such an ED-B region.

By "target specific" portion we mean the portion of the compound which comprises one or more binding sites which recognise and bind to oncofoetal fibronectin. Oncofoetal fibronectin is a protein that is expressed by tumour cells and is associated with tumour vasculature. This protein is also expressed in foetal tissue, but does not appear to be expressed at all in normal adult tissue except for regenerating endometrium and wound healing (Carnemolla et al., 1989, *J. Cell. Biol.* 108 p 1139-1148).

Oncofoetal fibronectin is generated by alternate splicing in tumour cells, through which an additional domain, termed the ED-B domain (complete type II repeat ED-B, also known as extratype III repeat B [EIIIB]), is inserted between fibronectin repeats 7 and 8. ED-B is a highly conserved domain with one hundred percent homology in the mammals studied to date (see Carnemolla et al., 1989, supra. and ffrench-Constant et al., 1989, *J. Cell. Biol.* 109 p 903-914).

Thus, the invention provides compounds for delivering IL12, or a functional fragment or variant thereof, to tumour cells by targeting oncofoetal fibronectin.

By "specificity for oncofoetal fibronectin" we mean that the target specific portion (i.e. the monoclonal antibody, or a fragment or variant thereof which retains the binding specificity for oncofoetal fibronectin of the parent monoclonal antibody) binds to oncofoetal fibronectin but does not bind substantially to fibronectin expressed by normal adult tissue.

Suitable monoclonal antibodies to target antigens (in this case, oncofoetal fibronectin) may be prepared by known techniques, for example those disclosed in *Monoclonal Antibodies: A manual of techniques*, H Zola (CRC Press, 1988) and in *Monoclonal Hybridoma Antibodies: Techniques and Applications*, J G R Hurrell (CRC Press, 1982) and *Antibody Engineering, A Practical Approach*, McCafferty, J. et al, ed. (IRL Press, 1996).

The target specific portion of the compounds of the invention are characterised by having specificity for a region of oncofoetal fibronectin other than the ED-B region. Rather, the target specific portion binds to a cryptic epitope which is exposed/accessible in oncofoetal fibronectin (which comprises the ED-B domain) but is not exposed/accessible in normal fibronectin (which lacks the ED-B domain). As a consequence, the target specific portion binds to the splice variant of fibronectin which comprises an ED-B domain, but does not bind to the ED-B domain itself.

Thus, targeting agents comprising the L19 antibody or antigen-binding fragments thereof (for example, as described in WO 03/076469) are excluded from the scope of the present invention, since the L19 antibody binds to the ED-B domain.

Preferably, the target specific portion binds to an amino acid sequence present in fibronectin expressed in both foetal and normal adult tissue. More preferably, the target specific portion binds to a fibronectin domain flanking, i.e. adjacent, the ED-B domain. Most preferably, the target specific portion binds to an amino acid sequence within the repeat 7 domain of fibronectin (see Example 3 below).

It will be appreciated by persons skilled in the art that the compounds of the invention may target oncofoetal fibronectin expressed by any species. Advantageously, the compounds are targeted to oncofoetal fibronectin from the species in which the compounds are to be used therapeutically. Thus, in a preferred embodiment, the target specific portion is specific for human oncofoetal fibronectin.

In a particularly preferred embodiment of the first aspect of the invention, the target specific portion comprises of consists of a murine BC1 antibody, or an antibody capable of competing with the binding of a BC1 antibody to oncofoetal fibronectin or a fragment or variant thereof which retains the antigen binding specificity of the parent monoclonal antibody. Production of the murine BC1 antibody is described in EP 0 344 134 B, and it is obtainable from the hybridoma deposited at the European Collection of Animal Cell Cultures, Porton Down, UK (Accession No. 88042101).

The BC1 antibody binds specifically to oncofoetal fibronectin via a site on repeat 7, outside the ED-B domain, that is masked in normal fibronectin but accessible when the ED-B domain is present (Carnemolla et al., 1989, *J. Cell Biol.* 109:1139-1148; Carnemolla et al., 1992, *J. Biol. Chem.* 267: 24689-24692; Mariani et al., 1997, *Cancer* 80:2378-2384; see also Example 1 below).

Methods for determining whether a test antibody is capable of competing with the binding of a BC1 antibody to oncofoetal fibronectin are well known in the art, such as competitive ELISA.

In a further preferred embodiment, the target-specific portion comprises a human antibody or a humanised antibody. By "humanised monoclonal antibody" we include monoclonal antibodies having at least one chain wherein the framework regions are predominantly derived from a first, acceptor monoclonal antibody of human origin and at least one complementarity-determining region (CDR) is derived from a second, donor monoclonal antibody having specificity for oncofoetal fibronectin. The donor monoclonal antibody may be of human or non-human origin, for example it may be a murine monoclonal antibody, such as BC1.

Preferably, both chains of the humanised monoclonal antibody comprise CDRs grafted from a donor monoclonal antibody having specificity for oncofoetal fibronectin.

Advantageously, the CDR-grafted (i.e. humanised) chain comprises two or all three CDRs derived from a donor antibody having specificity for oncofoetal fibronectin.

Conveniently, the humanised monoclonal antibody comprises only human framework residues and CDRs from a donor antibody having specificity for oncofoetal fibronectin.

However, it will be appreciated by those skilled in the art that in order to maintain and optimise the specificity of the humanised antibody it may be necessary to alter one or more residues in the framework regions such that they correspond to equivalent residues in the donor antibody.

Preferably, the framework regions of the humanised antibody are derived from a human IgG monoclonal antibody.

Methods of making humanised monoclonal antibodies are well-known in the art, for example see Jones et al. (1986) *Nature* 321:522-525, Riechmann et al. (1988) *Nature* 332: 323-327, Verhoeyen et al. (1988) *Science* 239:1534-1536 and EP 239 400.

In a further preferred embodiment, the compound of the first aspect of the invention binds to oncofoetal fibronectin with high avidity. By "high avidity" we mean that the target specific portion recognises oncofoetal fibronectin with a binding constant of at least $K_d=10^{-6}$ M, preferably at least $K_d=10^{-7}$ M, suitably $K_d=10^{-8}$ M, more suitably $K_d=10^{-9}$ M, yet more suitably still $K_d=10^{-10}$ M, and more preferably $K_d=10^{-11}$ M or even $K_d=10^{-12}$ M.

Preferably, the compound of the first aspect of the invention binds to oncofoetal fibronectin more tightly than the parent monoclonal antibody, e.g. BC1, used to produce the target specific portion. The tightness with which the compound and parent monoclonal antibody bind to oncofoetal fibronectin may be measured by determining a dissociation constant for binding to oncofoetal fibronectin (see Examples 2 and 3).

Advantageously, the compound binds to oncofoetal fibronectin at least 2-fold tighter than the parent monoclonal antibody, for example at least 2, 3, 4, 5, 6, 7, 8, 9, 10, 12, 15, 20-fold tighter. Conveniently, the compound binds to oncofoetal fibronectin at least 10-fold tighter than the parent monoclonal antibody binds to oncofoetal fibronectin.

In a preferred embodiment, the compound of the first aspect of the invention comprises a target specific portion comprising or consisting of a whole (i.e. intact) monoclonal antibody, preferably a BC1 antibody. Thus, the target specific portion may comprise two immunoglobulin heavy chains and two immunoglobulin light chains, which may be linked by disulphide bonds. One or more of the component chains may be conjugated, e.g. fused, to the effector portion. For example, the two immunoglobulin heavy chains may each be fused to an effector portion.

In an alternative preferred embodiment of the compounds of the invention, the target specific portion comprises or consists of an antigen-binding fragment of a monoclonal antibody having specificity for oncofoetal fibronectin (e.g. BC1).

The variable heavy ($V_H$) and variable light ($V_L$) domains of an antibody are involved in antigen recognition, a fact first recognised by early protease digestion experiments. Further confirmation was found by humanisation of rodent antibodies. Variable domains of rodent origin may be fused to constant domains of human origin such that the resultant antibody retains the antigenic specificity of the rodent parented antibody (Morrison et al (1984) *Proc. Natl. Acad. Sci. USA* 81, 6851-6855).

That antigenic specificity is conferred by variable domains and is independent of the constant domains is known from experiments involving the bacterial expression of antibody fragments, all containing one or more variable domains. These molecules include Fab-like molecules (Better et al (1988) *Science* 240, 1041); Fv molecules (Skerra et al (1988) *Science* 240, 1038); disulphide-linked Fv molecules (Young et al., 1995, *FEBS Lett.* 377:135-139); single-chain Fv (ScFv) molecules where the $V_H$ and $V_L$ partner domains are linked via a flexible oligopeptide (Bird et al (1988) *Science* 242, 423; Huston et al (1988) *Proc. Natl. Acad. Sci. USA* 85, 5879) and single domain antibodies (dAbs) comprising isolated V domains (Ward et al (1989) *Nature* 341, 544). A general review of the techniques involved in the synthesis of antibody fragments which retain their specific binding sites is to be found in Winter & Milstein (1991) *Nature* 349, 293-299.

The advantages of using antibody fragments, rather than whole antibodies, may be several-fold. The smaller size of the fragments allows for rapid clearance, and may lead to improved tumour to non-tumour ratios. Fab, Fv, ScFv, disulphide Fv and dAb antibody fragments can all be expressed in and secreted from bacteria, such as *E. coli*, or eukaryotic expression systems such as yeast or mammalian systems, thus allowing the facile production of large amounts of the said fragments.

Preferably, the target specific portion of the compounds of the invention comprises an antigen binding fragment of the humanised antibody selected from the group consisting of Fab-like molecules, such as Fab and F(ab')$_2$, Fv molecules, disulphide-linked Fv molecules, ScFv molecules and single domain antibodies (dAbs).

More preferably, the target specific portion comprises a Fab molecule or a F(ab')$_2$ molecule.

In a preferred embodiment, the compound of the first aspect of the invention comprises a target specific portion comprising a humanized BC1 heavy chain variable region of SEQ ID NO: 1.

[SEQ ID NO: 1]
EVQLVQSGADVKKPGASVKVSCKASGYTFTNYVMHWVRQAPGQGLEWLGY

INPYNDGTQYNERFKGRVTMTGDTSISTAYMELSRLTSDDTAVYYCAREV

YGNYIWGNWGQGTLVSVSS

Advantageously, the compound of the first aspect of the invention comprises a target specific portion comprising a humanized BC1 light chain variable region of EQ ID NO: 2.

[SEQ ID NO: 2]
EIVLTQSPGTLSLSPGERATLSCSASSSISSNYLHWYQQKPGQAPRLLIY

RTSNLASGIPDRFSGSGSGTDFTLTISRLEPEDFAVYYCQQGSSIPFTFG

QGTKLEIK

Conveniently, the compound of the first aspect of the invention comprises a target specific portion comprising a humanized BC1 heavy chain variable region of SEQ ID NO: 1 and a humanized BC1 light chain variable region of SEQ ID NO: 2.

In a further preferred embodiment, the target specific portion comprises one or more antibody constant regions, such as the CH1, CH2 and CH3 immunoglobulin constant domains. The one or more constant regions may be from same or different antibody to the variable regions of the target portion. Likewise, the compound of the invention may comprise an immunoglobulin heavy chain and an immunoglobulin light chain, each of which comprises a constant region (which constant regions may be from the same or different parent antibodies).

Preferably, the one or more antibody constant regions comprises or consists of a CH1 domain.

In a further preferred embodiment, the compound of the invention further comprises an immunoglobulin Fc moiety. Advantageously, the Fc moiety is derived from a human IgG1 antibody.

By "Fc moiety" we mean an antibody fragment comprising the CH2 and CH3 domains of an IgG heavy chain constant region, i.e. structurally equivalent to the fragment producible by papain cleavage of an IgG molecule, or a polypeptide which is functionally equivalent thereto.

As detailed above, the compounds of the first aspect of the invention comprise an effector portion which comprises or consists of IL-12 or a functional fragment or variant thereof (i.e. an 'IL-12 moiety'). By a "functional" fragment or variant we include the meaning of a fragment or variant capable of stimulating a Th1 immune response in a mammalian host, i.e. the differentiation of Th1 cells from naïve T cells.

Thus, the effector portion comprises or consists of polypeptide having IL-12 activity.

Preferably, the effector portion comprises or consists of human interleukin-12, or a functional fragment or variant thereof.

Conveniently, the effector portion comprises or consists of a single-chain interleukin-12, for example comprising or consisting of an IL-12p35 domain and an IL-12p40 domain. Preferably, the IL-12p35 domain is conjugated to IL-12p40 domain by a disulphide bond.

Preferably, the effector portion comprises an IL-12p35 domain of the following amino acid sequence:

[SEQ ID NO: 3]
NLPVATPDPGMFPCLHHSQNLLRAVSNMLQKARQTLEFYPCTSEEIDHED

ITKDKTSTVEACLPLELTKNESCLNSRETSFITNGSCLASRKTSFMMALC

LSSIYEDLKMYQVEFKTMNAKLLMDPKRQIFLDQNMLAVIDELMQALNFN

SETVPQKSSLEEPDFYKTKIKLCILLHAFRIRAVTIDRVMSYLNAS

Preferably, the effector portion comprises an IL-12p40 domain of the following amino acid sequence:

[SEQ ID NO: 4]
IWELKKDVYVVELDWYPDAPGEMVVLTCDTPEEDGITWTLDQSSEVLGSG

KTLTIQVKEFGDAGQYTCHKGGEVLSHSLLLLHKKEDGIWSTDILKDQKE

PKNKTFLRCEAKNYSGRFTCWWLTTISTDLTFSVKSSRGSSDPQGVTCGA

ATLSAERVRGDNKEYEYSVECQEDSACPAAEESLPIEVMVDAVHKLKYEN

YTSSFFIRDIIKPDPPKNLQLKPLKNSRQVEVSWEYPDTWSTPHSYFSLT

FCVQVQGKSKREKKDRVFTDKTSATVICRKNASISVRAQDRYYSSSWSEW

ASVPCS

In a particularly preferred embodiment of the first aspect of the invention, the compound is or comprises a fusion compound or fusion protein. By "fusion compound" we include a compound comprising one or more functionally distinct portions, wherein the distinct portions are contained within a single polypeptide chain produced by recombinant DNA techniques. For example, the compound may comprise a whole antibody wherein the heavy chain is fused to a single chain IL-12. Alternatively, the compound may comprise a Fab or F(ab')$_2$ fragment of an antibody wherein the truncated heavy chain (i.e. the Fd chain) is fused to a single chain IL-12.

Preferably, the target specific portion and the effector portion of the fusion compound are fused. These portions may be fused directly, or via a linker sequence (for example to allow greater flexibility of the portions relative to one another).

Suitably, the linker is a mutated linker sequence comprising or consisting of the amino acid sequence ATATPGAA [SEQ ID NO. 5].

Alternatively, the target specific portion and the effector portion of the compound of the invention are separate moieties linked together by any of the conventional ways of cross-linking polypeptides, such as those generally described in O'Sullivan et al Anal. Biochem. (1979) 100, 100-108. For example, the antibody portion may be enriched with thiol groups and the enzyme portion reacted with a bifunctional agent capable of reacting with those thiol groups, for example the N-hydroxysuccinimide ester of iodoacetic acid (NHIA) or N-succinimidyl-3-(2-pyridyldithio)propionate (SPDP). Amide and thioether bonds, for example achieved with m-maleimidobenzoyl-N-hydroxysuccinimide ester, are generally more stable in vivo than disulphide bonds.

In a preferred embodiment, the compound comprises a polypeptide of SEQ ID NO:6
BC1 Heavy Chain Fused to Human IL-12 p35

[SEQ ID NO: 6]
EVQLVQSGADVKKPGASVKVSCKASGYTFTNYVMHWVRQAPGQGLEWLGY

INPYNDGTQYNERFKGRVTMTGDTSISTAYMELSRLTSDDTAVYYCAREV

YGNYIWGNWGQGTLVSVSSASTKGPSVFPLAPSSKSTSGGTAALGCLVKD

```
YFPEPVTVSWNSGALTSGVHTFPAVLQSSGLYSLSSVVTVPSSSLGTQTY

ICNVNHKPSNTKVDKRVEPKSCDKTHTCPPCPAPELLGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSREEMTKNQVSLTCLVKGFYPSDIAVEWESNGQPENNYKTTPPVL

DSDGSFFLYSKLTVDKSRWQQGNVFSCSVMHEALHNHYTQKSATATPGAA

NLPVATPDPGMFPCLHHSQNLLRAVSNMLQKARQTLEFYPCTSEEIDHED

ITKDKTSTVEACLPLELTKNESCLNSRETSFITNGSCLASRKTSFMMALC

LSSIYEDLKMYQVEFKTMNAKLLMDPKRQIFLDQNMLAVIDELMQALNFN

SETVPQKSSLEEPDFYKTKIKLCILLHAFRIRAVTIDRVMSYLNAS
```

In a further preferred embodiment, the compound comprises a polypeptide of SEQ ID NO:7.
BC1 Light Chain

```
                                           [SEQ ID NO: 7]
EIVLTQSPGTLSLSPGERATLSCSASSSISSNYLHWYQQKLPGQAPRLLI

YRTSNLASGIPDRFSGSGSGTDFTLTISRLEPEDFAVYYCQQGSSIPFTF

GQGTKLEIKRTVAAPSVFIFPPSDEQLKSGTASVVCLLNNFYPREAKVQW

KVDNALQSGNSQESVTEQDSKDSTYSLSSTLTLSKADYEKHKVYACEVTH

QGLSSPVTKSFNRGEC
```

In a particularly preferred embodiment, the compound comprises a polypeptide of SEQ ID NO:6 and a polypeptide of SEQ ID NO:7.

Advantageously, the compound further comprises a polypeptide of SEQ ID 4 linked by disulphide bond to the polypeptide of SEQ ID NO:6.

Thus, the invention provides a fusion protein comprising antibody V regions directed against oncofoetal fibronectin, an Fc moiety, and an interleukin-12 moiety. Specifically, the invention provides an immunoglobulin (Ig) fusion protein comprising antibody V regions that bind to oncofetal fibronectin, fused to interleukin-12. In a preferred embodiment of this invention, the antibody V regions are from the BC1 antibody (Carnemolla et al. (1992), *J. Biol. Chem.* 267: 24689-24692; Mariani et al. (1997), *Cancer* 80:2378-2384). The Fc moiety is preferably derived from human IgG1.

In a preferred embodiment, the fusion protein comprises antibody V regions as shown in SEQ ID 6 and 7, and an interleukin-12 moiety. Preferably, IL-12 moiety is a single-chain interleukin-12.

An unexpected feature of this invention is that the fusion protein binds to oncofetal fibronectin much more tightly than does the corresponding BC1 antibody alone. Such tight binding is useful in treating cancer, as the tighter binding leads to better tumour targeting of IL-12 than would be expected on the basis of the affinity of the BC1 antibody for oncofetal fibronectin. Tighter binding is particularly advantageous for target antigens that do not turn over rapidly, such as components of the extracellular matrix.

In a preferred embodiment, antibody constant regions are also used, e.g. a CH1 domain. FIG. 1 illustrates some of the configurations of antibody variable regions (striped ovals), constant regions (white ovals), the IL-12 p35 subunit (small rectangles), the IL-12 p40 subunit (large rectangles), antibody hinges and linkers (thick lines) and disulfide bonds (thin lines). Particular preferred embodiments include intact IgG-type antibodies with p35 fused to the C-terminus of the heavy chain and p40 attached to p35 by a disulfide bond (FIG. 1A), a 'minibody' with the antibody V regions connected by a linker and attached through a hinge to a CH3 domain, and p35 fused to the C-terminus of the heavy chain and p40 attached to p35 by a disulfide bond (FIG. 1B), an sFv with p35 fused to a V region and p40 attached by a disulfide bond (FIG. 1C), and an Fab with p35 fused to a C region and p40 attached by a disulfide bond (FIG. 1D). The IL-12 p35 subunit may also be attached to the N-terminus of a V region. The IL-12 p40 subunit may be attached to p35 through a disulfide bond or through a linker, yielding a so-called 'single-chain IL-12' moiety (scIL-12).

In a more preferred embodiment, an intact BC1 antibody with constant regions of human IgG1 is used. A particular advantage of this molecule is that is has effector functions such as ADCC, which are lacking in minibody, Fab, and sFv fusion proteins.

A second aspect of the invention provides a nucleic acid molecule encoding a compound according to the first aspect of the invention, or a target specific portion, effector portion or one or more component polypeptides thereof (e.g. a BC1 heavy chain, a BC1 light chain, IL12 p35 and p40 subunits and/or an Fc moiety). By "nucleic acid molecule" we include DNA, cDNA and mRNA molecules.

In a preferred embodiment, the nucleic acid molecule of the invention comprises one or more of the nucleotide sequences selected from the groups consisting of SEQ ID NOS: 8, 9 and 10.

HuBC1 Heavy Chain Fused to huIL12 p35 Subunit (VH is Underlined; the p35 Sequence is in Bold; and the Upper and Lower Cases Represent the Coding and Non-Coding Sequences, Respectively):

```
                                           [SEQ ID NO: 8]
ATGGAGTTGCCTGTTAGGCTGTTGGTGCTGATGTTCTGGATTCCTGgtga ggagagagggaagtgagggaggagaatggacagggagcaggagcactgaa tcccattgctcattccatgtatctggcatgggtgagaagatgggtcttat cctccagcatggggcctctggggtgaatacttgttagagggaggttccag atgggaacatgtgctataatgaagattatgaaatggatgcctgggatggt ctaagtaatgccttagaagtgactagacacttgcaattcactttttttgg taagaagagatttttaggctataaaaaaatgttatgtaaaaataaacgat cacagttgaaataaaaaaaaatataaggatgttcatgaattttgtgtat aactatgtatttctctctcattgtttcagCTTCCTTAAGCGAGGTGCAGC

TGGTGCAGTCTGGGGCTGACGTGAAGAAGCCTGGGGCCTCAGTGAAGGTC

TCCTGCAAGGCTTCTGGATACACCTTCACCAACTACGTAATGCACTGGGT

GCGACAGGCCCCTGGACAAGGGCTTGAGTGGCTGGGATATATTAATCCTT

ACAATGATGGTACTCAGTACAATGAGAGGTTCAAAGGCAGGGTCACCATG

ACCGGGGACACGTCCATCAGTACAGCCTATATGGAGCTGAGCAGGCTGAC

TTCTGACGACACCGCGGTGTATTACTGTGCGAGAGAGGTCTATGGTAACT

ACATCTGGGGCAACTGGGGCCAGGGAACCCTGGTCTCCGTCTCCTCAGgt aagtaagctttctggggcaggccaggcctgaccttggctttggggcaggg aggggctaaggtgaggcaggtggcgccagccaggtgcacacccaatgcc catgagcccagacactggacgctgaacctcgcggacagttaagaacccag
```

-continued gggcctctgcgccctgggcccagctctgtcccacaccgcggtcacatggc accacctctcttgcagCCTCCACCAAGGGCCCATCGGTCTTCCCCCTGGC

ACCCTCCTCCAAGAGCACCTCTGGGGGCACAGCGGCCCTGGGCTGCCTGG

TCAAGGACTACTTCCCCGAACCGGTGACGGTGTCGTGGAACTCAGGCGCC

CTGACCAGCGGCGTGCACACCTTCCCGGCTGTCCTACAGTCCTCAGGACT

CTACTCCCTCAGCAGCGTGGTGACCGTGCCCTCCAGCAGCTTGGGCACCC

AGACCTACATCTGCAACGTGAATCACAAGCCCAGCAACACCAAGGTGGAC

AAGAGAGTTGgtgagaggccagcacagggagggagggtgtctgctggaag ccaggctcagcgctcctgcctggacgcatcccggctatgcagtcccagtc cagggcagcaaggcaggccccgtctgcctcttcaccggaggcctctgcc cgccccactcatgctcagggagagggtcttctggcttttttcccaggctc tgggcaggcacaggctaggtgccctaacccaggccctgcacacaaaggg gcaggtgctgggctcagacctgccaagagccatatccgggaggaccctgc ccctgacctaagcccacccaaaggccaaactctccactccctcagctcg gacaccttctctcctcccagattccagtaactcccaatcttctctctgca gAGCCCAAATCTTGTGACAAAACTCACACATGCCCACCGTGCCCAGgtaa gccagcccaggcctcgccctccagctcaaggcgggacaggtgccctagag tagcctgcatccagggacaggccccagccgggtgctgacacgtccacctc catctcttcctcagCACCTGAACTCCTGGGGGGACCGTCAGTCTTCCTCT

TCCCCCCAAAACCCAAGGACACCCTCATGATCTCCCGGACCCCTGAGGTC

ACATGCGTGGTGGTGGACGTGAGCCACGAAGACCCTGAGGTCAAGTTCAA

CTGGTACGTGGACGGCGTGGAGGTGCATAATGCCAAGACAAAGCCGCGGG

AGGAGCAGTACAACAGCACGTACCGTGTGGTCAGCGTCCTCACCGTCCTG

CACCAGGACTGGCTGAATGGCAAGGAGTACAAGTGCAAGGTCTCCAACAA

AGCCCTCCCAGCCCCCATCGAGAAAACCATCTCCAAAGCCAAAGtggga cccgtggggtgcgagggccacatggacagaggccggctcggcccaccctc tgccctgagagtgaccgctgtaccaacctctgtccctacagGGCAGCCCC

GAGAACCACAGGTGTACACCCTGCCCCCATCACGGGAGGAGATGACCAAG

AACCAGGTCAGCCTGACCTGCCTGGTCAAAGGCTTCTATCCCAGCGACAT

CGCCGTGGAGTGGGAGAGCAATGGGCAGCCGGAGAACAACTACAAGACCA

CGCCTCCCGTGCTGGACTCCGACGGCTCCTTCTTCCTCTATAGCAAGCTC

ACCGTGGACAAGAGCAGGTGGCAGCAGGGGAACGTCTTCTCATGCTCCGT

GATGCATGAGGCTCTGCACAACCACTACACGCAGAAGAGCGCCACCGCGA

CCCCGGGCGCCGCAAACCTCCCCGTGGCCACTCCAGACCCAGGAATGTTC

CCATGCCTTCACCACTCCCAAAACCTGCTGAGGGCCGTCAGCAACATGCT

CCAGAAGGCCAGACAAACTCTAGAATTTTACCCTTGCACTTCTGAAGAGA

TTGATCATGAAGATATCACAAAAGATAAAACCAGCACAGTGGAGGCCTGT

TTACCATTGGAATTAACCAAGAATGAGAGTTGCCTAAATTCCAGAGAGAC

CTCTTTCATAACTAATGGGAGTTGCCTGGCCTCCAGAAAGACCTCTTTTA

TGATGGCCCTGTGCCTTAGTAGTATTTATGAAGACTTGAAGATGTACCAG

GTGGAGTTCAAGACCATGAATGCAAAGCTTCTGATGGATCCTAAGAGGCA

GATCTTTCTAGATCAAAACATGCTGGCAGTTATTGATGAGCTGATGCAGG

CCCTGAATTTCAACAGTGAGACTGTGCCACAAAAATCCTCCCTTGAAGAA

CCGGATTTTTATAAAACTAAAATCAAGCTCTGCATACTTCTTCATGCTTT

CAGAATTCGGGCAGTGACTATTGACAGAGTGACGAGCTATCTGAATGCTT

CCTAA

HuBC1 Light Chain (VL is Underlined; the Upper and Lower Cases Represent the Coding and Non-Coding Sequences, Respectively)

[SEQ ID NO: 9]
ATGGAGTTGCCTGTTAGGCTGTTGGTGCTGATGTTCTGGATTCCTGgtga ggagagagggaagtgagggaggagaatggacagggagcaggagcactgaa tcccattgctcattccatgtatctggcatgggtgagaagatgggtcttat cctccagcatggggcctctggggtgaatacttgttagagggaggttccag atgggaacatgtgctataatgaagattatgaaatggatgcctgggatggt ctaagtaatgccttagaagtgactagacacttgcaattcactttttttgg taagaagagattttaggctataaaaaaatgttatgtaaaaataaacgat cacagttgaataaaaaaaaatataaggatgttcatgaattttgtgtat aactatgtatttctctctcattgtttcagCTTCCTTAAGC<u>GAAATTGTGT</u>

<u>TGACGCAGTCTCCAGGCACCCTGTCTTTGTCTCCAGGGGAAAGAGCCACC</u>

<u>CTCTCCTGCAGTGCCAGTTCAAGTATAAGTTCCAATTACTTGCATTGGTA</u>

<u>CCAGCAGAAACCTGGCCAGGCTCCCAGGCTCCTCATCTATAGGACGTCCA</u>

<u>ATCTGGCTTCTGGCATCCCAGACAGGTTCAGTGGCAGTGGGTCTGGGACA</u>

<u>GACTTCACTCTCACCATCAGCAGACTGGAGCCTGAAGATTTTGCAGTGTA</u>

<u>TTACTGTCAGCAGGGTAGTAGTATACCATTCACGTTTGGCCAGGGGACCA</u>

<u>AGCTGGAGATCAAAC</u>gtaagtggatcctatcagggttttacaagagggac taaagacatgtcagctatgtgtgactaatggtaatgtcactaagctgcgc gatcccgcaattctaaactctgaggggtcggatgacgtggccattcttt gcctaaagcattgagtttactgcaaggtcagaaaagcatgcaaagccctc agaatggctgcaaagagctccaacaaaacaatttagaactttattaagga ataggggaagctaggaagaaactcaaaacatcaagattttaaatacgct tcttggtctccttgctataattatctgggataagcatgctgttttctgtc tgtccctaacatgccctgtgattatccgcaaacaacacacccaagggcag aactttgttacttaaacaccatcctgtttgcttctttcctcagGAACTGT

GGCTGCACCATCTGTCTTCATCTTCCCGCCATCTGATGAGCAGTTGAAAT

CTGGAACTGCCTCTGTTGTGTGCCTGCTGAATAACTTCTATCCCAGAGAG

GCCAAAGTACAGTGGAAGGTGGATAACGCCCTCCAATCGGGTAACTCCCA

GGAGAGTGTCACAGAGCAGGACAGCAAGGACAGCACCTACAGCCTCAGCA

GCACCCTGACGCTGAGCAAAGCAGACTACGAGAAACACAAAGTCTACGCC

TGCGAAGTCACCCATCAGGGCCTGAGCTCGCCCGTCACAAAGAGCTTCAA

CAGGGGAGAGTGTTAG

HuIL12 p40 Subunit (This Construct is a cDNA of the p40 mRNA. The DNA Coding for Its Native Signal Peptide is in Italics, and this is Followed by DNA Coding for the Mature p40):

[SEQ ID NO: 10]
ATGTGTCACCAGCAGTTGGTCATCTCTTGGTTTTCCCTGGTTTTTCTGGC

ATCTCCCCTCGTGGCCATATGGGAACTGAAGAAAGATGTTTATGTCGTAG

AATTGGATTGGTATCCGGATGCCCCTGGAGAAATGGTGGTCCTCACCTGT

GACACCCCTGAAGAAGATGGTATCACCTGGACCTTGGACCAGAGCAGTGA

GGTCTTAGGCTCTGGCAAAACCCTGACCATCCAGTCAAAGAGTTTGGAGA

TGCTGGCCAGTACACCTGTCACAAAGGAGGCGAGGTTCTAAGCCATTCGC

TCCTGCTGCTTCACAAAAAGGAAGATGGAATTTGGTCCACTGATATTTTA

AAGGACCAGAAAGAACCCAAAAATAAGACCTTTCTAAGATGCGAGGCCAA

GAATTATTCTGGACGTTTCACCTGCTGGTGGCTGACGACAATCAGTACTG

ATTTGACATTCAGTGTCAAAAGCAGCAGAGGCTCTTCTGACCCCCAAGGG

GTGACGTGCGGAGCTGCTACACTCTCTGCAGAGAGAGTCAGAGGGGACAA

CAAGGAGTATGAGTACTCAGTGGAGTGCCAGGAGGACAGTGCCTGCCCAG

CTGCTGAGGAGAGTCTGCCCATTGAGGTCATGGTGGATGCCGTTCACAAG

CTCAAGTATGAAAACTACACCAGCAGCTTCTTCATCAGGGACATCATCAA

ACCTGACCCACCCAAGAACTTGCAGCTGAAGCCATTAAAGAATTCTCGGC

AGGTGGAGGTCAGCTGGGAGTACCCTGACACCTGGAGTACTCCACATTCC

TACTTCTCCCTGACATTCTGCGTTCAGGTCCAGGGCAAGAGCAAGAGAGA

AAAGAAAGATAGAGTCTTCACGGACAAGACCTCAGCCACGGTCATCTGCC

GCAAAAATGCCAGCATTAGCGTGCGGGCCCAGGACCGCTACTATAGCTCA

TCTTGGAGCGAATGGGCATCTGTGCCCTGCAGTTAG

Alternatively, the nucleic acid molecule comprises nucleotide sequences that are degenerate sequences of those nucleotide sequences identified above (i.e. which encode the same amino acid sequence).

Preferably, the nucleic acid molecule comprises the nucleotide sequence of SEQ ID NO: 8.

Advantageously, the nucleic acid molecule comprises the nucleotide sequence of SEQ ID NO: 9.

Conveniently, the nucleic acid molecule comprises the nucleotide sequence of SEQ ID NO: 8 and the nucleotide sequence of SEQ ID NO: 9.

Suitably, the nucleic acid molecule comprises the nucleotide sequence of SEQ ID NO: 10.

A further aspect of the present invention provides a method of making a compound according to the first aspect of the invention, said method comprising expressing one or more nucleic acid molecules according to the second aspect of the invention in a host cell and isolating the compound therefrom (see Example 1).

It is preferable that the two portions of the compound of the invention are produced as a fusion compound by recombinant DNA techniques, whereby a length of DNA comprises respective regions encoding the two portions of the compound of the invention either adjacent one another or separated by a region encoding a linker peptide which does not destroy the desired properties of the compound.

The nucleic acid may be expressed in a suitable host to produce a polypeptide comprising the compound of the invention. Thus, the nucleic acid encoding the compound of the invention or a portion thereof may be used in accordance with known techniques, appropriately modified in view of the teachings contained herein, to construct an expression vector, which is then used to transform an appropriate host cell for the expression and production of the compound of the invention. Such techniques include those disclosed in U.S. Pat. No. 4,440,859 issued 3 Apr. 1984 to Rutter et al, U.S. Pat. No. 4,530,901 issued 23 Jul. 1985 to Weissman, U.S. Pat. No. 4,582,800 issued 15 Apr. 1986 to Crowl, U.S. Pat. No. 4,677,063 issued 30 Jun. 1987 to Mark et al, U.S. Pat. No. 4,678,751 issued 7 Jul. 1987 to Goeddel, U.S. Pat. No. 4,704,362 issued 3 Nov. 1987 to Itakura et al, U.S. Pat. No. 4,710,463 issued 1 Dec. 1987 to Murray, U.S. Pat. No. 4,757,006 issued 12 Jul. 1988 to Toole, Jr. et al, U.S. Pat. No. 4,766,075 issued 23 Aug. 1988 to Goeddel et al and U.S. Pat. No. 4,810,648 issued 7 Mar. 1989 to Stalker, all of which are incorporated herein by reference.

Where the compound of the invention is multimeric, the constituent chains may be encoded by a single nucleic acid molecule or separate nucleic acid molecule (expressed in a common host cell or in different host cells and assembled in vitro).

The nucleic acid encoding the compound of the invention or a portion thereof may be joined to a wide variety of other nucleic acid sequences for introduction into an appropriate host. The companion nucleic acid will depend upon the nature of the host, the manner of the introduction of the nucleic acid into the host, and whether episomal maintenance or integration is desired.

It will be appreciated that in order to prevent expression of the cytotoxic portion of the compound of the invention from killing the host cells in which it is expressed, it may be necessary to link the nucleic acid of the second aspect of the invention to a signal sequence capable of directing secretion of the expressed compound (or portion) out of the host cell. Signal sequences will be selected according to the type of host cell used. Exemplary signal sequences include the ompA signal sequence (for example, see Takahara et al., 1985, *J. Biol. Chem.* 260(5):2670-2674).

Generally, the nucleic acid is inserted into an expression vector, such as a plasmid, in proper orientation and correct reading frame for expression. If necessary, the nucleic acid may be linked to the appropriate transcriptional and translational regulatory control nucleotide sequences recognised by the desired host, although such controls are generally available in the expression vector. For example, the nucleic acid molecule encoding a compound of the invention may be linked to or comprise a Kozak consensus ribosome binding sequence (such as GCCGCCACC) to enhance translation.

The vector is then introduced into the host through standard techniques. Generally, not all of the hosts will be transformed by the vector. Therefore, it will be necessary to select for transformed host cells. One selection technique involves incorporating into the expression vector a nucleic acid sequence, with any necessary control elements, that codes for a selectable trait in the transformed cell, such as antibiotic resistance. Alternatively, the gene for such selectable trait can be on another vector, which is used to co-transform the desired host cell.

Host cells that have been transformed by the recombinant nucleic acid of the invention are then cultured for a sufficient time and under appropriate conditions known to those skilled in the art in view of the teachings disclosed herein to permit the expression of the polypeptide, which can then be recovered.

Many expression systems are known, including bacteria (for example *E. coli* and *Bacillus subtilis*), yeasts (for example *Saccharomyces cerevisiae* and *Pichia pastoris*), filamentous fungi (for example *Aspergillus*), plant cells, animal cells (for example COS-1, COS-7, CHO, NIH 3T3, NS0 and BHK cells) and insect cells (for example *Drosophila*, SF9 cells).

Those vectors that include a replicon such as a procaryotic replicon can also include an appropriate promoter such as a procaryotic promoter capable of directing the expression (transcription and translation) of the genes in a bacterial host cell, such as *E. coli*, transformed therewith.

A promoter is an expression control element formed by a DNA sequence that permits binding of RNA polymerase and transcription to occur. Promoter sequences compatible with exemplary bacterial hosts are typically provided in plasmid vectors containing convenient restriction sites for insertion of a DNA segment of the present invention.

Typical procaryotic vector plasmids are pUC18, pUC19, pBR322 and pBR329 (available from Biorad Laboratories, Richmond, Calif., USA), pTrc99A and pKK223-3 (available from Pharmacia Piscataway, N.J., USA) and the pET system (T7 promoter, Novagen Ltd).

A typical mammalian cell vector plasmid is pSVL available from Pharmacia, Piscataway, N.J., USA. This vector uses the SV40 late promoter to drive expression of cloned genes, the highest level of expression being found in T antigen-producing cells, such as COS-1 cells.

An example of an inducible mammalian expression vector is pMSG, also available from Pharmacia. This vector uses the glucocorticoid-inducible promoter of the mouse mammary tumour virus long terminal repeat to drive expression of the cloned gene.

Useful yeast plasmid vectors are pRS403-406 and pRS413-416 and are generally available from Stratagene Cloning Systems, La Jolla, Calif. 92037, USA. Plasmids pRS403, pRS404, pRS405 and pRS406 are Yeast Integrating plasmids (YIps) and incorporate the yeast selectable markers his3, trp1, leu2 and ura3. Plasmids pRS413-416 are Yeast Centromere plasmids (YCps).

Further useful vectors for transformation of yeast cells, such as *Pichia*, include the 2μ plasmid pYX243 (available from R and D Systems Limited) and the integrating vector pPICZ series (available from Invitrogen).

A variety of methods have been developed to operatively link DNA to vectors via complementary cohesive termini. For instance, complementary homopolymer tracts can be added to the DNA segment to be inserted to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. The DNA segment, generated by endonuclease restriction digestion as described earlier, is treated with bacteriophage T4 DNA polymerase or *E. coli* DNA polymerase I, enzymes that remove protruding, 3'-single-stranded termini with their 3'-5'-exonucleolytic activities, and fill in recessed 3'-ends with their polymerizing activities.

The combination of these activities therefore generates blunt-ended DNA segments. The blunt-ended segments are then incubated with a large molar excess of linker molecules in the presence of an enzyme that is able to catalyze the ligation of blunt-ended DNA molecules, such as bacteriophage T4 DNA ligase. Thus, the products of the reaction are DNA segments carrying polymeric linker sequences at their ends. These DNA segments are then cleaved with the appropriate restriction enzyme and ligated to an expression vector that has been cleaved with an enzyme that produces termini compatible with those of the DNA segment.

Synthetic linkers containing a variety of restriction endonuclease sites are commercially available from a number of sources including International Biotechnologies Inc, New Haven, Conn., USA.

A desirable way to modify the nucleic acid encoding the compound of the invention or a portion thereof is to use the polymerase chain reaction as disclosed by Saiki et al (1988) *Science* 239, 487-491.

In this method the nucleic acid to be enzymatically amplified is flanked by two specific oligonucleotide primers which themselves become incorporated into the amplified nucleic acid. The said specific primers may contain restriction endonuclease recognition sites which can be used for cloning into expression vectors using methods known in the art.

Exemplary genera of yeast contemplated to be useful in the practice of the present invention are *Pichia, Saccharomyces, Kluyveromyces, Candida, Torulopsis, Hansenula, Schizosaccharomyces, Citeromyces, Pachysolen, Debaromyces, Metschunikowia, Rhodosporidium, Leucosporidium, Botryoascus, Sporidiobolus, Endomycopsis,* and the like. Preferred genera are those selected from the group consisting of *Pichia, Saccharomyces, Kluyveromyces, Yarrowia* and *Hansenula*. Examples of *Saccharomyces* are *Saccharomyces cerevisiae, Saccharomyces italicus* and *Saccharomyces rouxii*. Examples of *Kluyveromyces* are *Kluyveromyces fragilis* and *Kluyveromyces lactis*. Examples of *Hansenula* are *Hansenula polymorpha, Hansenula anomala* and *Hansenula capsulata*. *Yarrowia lipolytica* is an example of a suitable *Yarrowia* species.

Methods for the transformation of *S. cerevisiae* are taught generally in EP 251 744, EP 258 067 and WO 90/01063, all of which are incorporated herein by reference.

Suitable promoters for *S. cerevisiae* include those associated with the PGK1 gene, GAL1 or GAL10 genes, CYC1, PHO5, TRP1, ADH1, ADH2, the genes for glyceraldehyde-3-phosphate dehydrogenase, hexokinase, pyruvate decarboxylase, phosphofructokinase, triose phosphate isomerase, phosphoglucose isomerase, glucokinase, α-mating factor pheromone, a-mating factor pheromone, the PRB1 promoter, the GUT2 promoter, and hybrid promoters involving hybrids of parts of 5' regulatory regions with parts of 5' regulatory regions of other promoters or with upstream activation sites (e.g. the promoter of EP-A-258 067).

The transcription termination signal is preferably the 3' flanking sequence of a eukaryotic gene which contains proper signals for transcription termination and polyadenylation. Suitable 3' flanking sequences may, for example, be those of the gene naturally linked to the expression control sequence used, i.e. may correspond to the promoter. Alternatively, they may be different in which case the termination signal of the *S. cerevisiae* AHD1 gene is preferred.

The present invention also relates to a host cell transformed with a polynucleotide vector construct of the present invention. The host cell can be either procaryotic or eukaryotic. Bacterial cells are preferred procaryotic host cells and typically are a strain of *E. coli* such as, for example, the *E. Coli* strains DH5 available from Bethesda Research Laboratories Inc., Bethesda, Md., USA, and RR1 available from the American Type Culture Collection (ATCC) of Rockville, Md., USA (No ATCC 31343). Preferred eukaryotic host cells include yeast and mammalian cells, preferably vertebrate cells such as those from a mouse, rat, monkey or human fibroblastic cell line. Preferred eukaryotic host cells include NS0 cells, Chinese hamster ovary (CHO) cells available from the ATCC as CCL61, NIH Swiss mouse embryo cells NIH/

3T3 available from the ATCC as CRL 1658 and monkey kidney-derived COS-1 cells available from the ATCC as CRL 1650 or WSØ cells.

Transformation of appropriate cell hosts with a nucleic acid constructs of the present invention is accomplished by well known methods that typically depend on the type of vector used. With regard to transformation of procaryotic host cells, see, for example, Cohen et al, *Proc. Natl. Acad. Sci. USA,* 69: 2110 (1972); and Sambrook et al, *Molecular Cloning, A Laboratory Manual*, Cold Spring Harbor Laboratory, Cold Spring Harbor, N.Y. (1989). Transformation of yeast cells is described in Sherman et al, *Methods In Yeast Genetics, A Laboratory Manual*, Cold Spring Harbor, N.Y. (1986). The method of Beggs, *Nature,* 275: 104-109 (1978) is also useful. With regard to vertebrate cells, reagents useful in transfecting such cells, for example calcium phosphate and DEAE-dextran or liposome formulations, are available from Stratagene Cloning Systems, or Life Technologies Inc, Gaithersburg, Md. 20877, USA.

Successfully transformed cells, i.e. cells that contain a nucleic acid construct of the present invention, can be identified by well known techniques. For example, cells resulting from the introduction of an expression construct of the present invention can be grown to produce the polypeptide of the invention. Cells can be harvested and lysed and their DNA content examined for the presence of the DNA using a method such as that described by Southern, *J. Mol. Biol.,* 98: 503 (1975) or Berent et al, *Biotech.,* 3: 208 (1985). Alternatively, the presence of the protein in the supernatant can be detected using antibodies as described below.

In addition to directly assaying for the presence of recombinant nucleic acid, successful transformation can be confirmed by well known immunological methods when the recombinant nucleic acid is capable of directing the expression of the protein. For example, cells successfully transformed with an expression vector produce proteins displaying appropriate antigenicity. Samples of cells suspected of being transformed are harvested and assayed for the protein using suitable antibodies.

Thus, in addition to the transformed host cells themselves, the present invention also contemplates a culture of those cells, preferably a monoclonal (clonally homogeneous) culture, or a culture derived from a monoclonal culture, in a nutrient medium. Preferably, the culture also contains the protein.

Nutrient media useful for culturing transformed host cells are well known in the art and can be obtained from several commercial sources.

A third aspect of the invention provides a vector comprising a nucleic acid according to the second aspect of the invention.

A fourth aspect of the invention provides a host cell comprising a vector according to the third aspect of the invention.

Preferably, the host cell is a mammalian cell, such as an NS/0 or CHO cell.

The compound of the invention may be purified from the culture medium using, in sequence, some or all of the following steps: Abx Mixed Resin column chromatography, recombinant Protein A chromatography, and Q Sepharose column chromatography, followed by Pellicon 2 tangential flow diafiltration for buffer exchange into formulation buffer. Virus inactivation and removal steps may be interdigitated into these steps. The virus inactivation and removal steps are not necessary for purification per se, but are used to satisfy regulatory considerations Detailed methods suitable for producing compounds of the invention are described in Gillies et al. (WO 99/29732, incorporated herein by reference). Other suitable techniques are described in *Molecular Cloning: a Laboratory Manual:* 3rd edition, Sambrook and Russell, 2001, Cold Spring Harbor Laboratory Press.

A fifth aspect of the invention provides a pharmaceutical composition comprising a compound according to the first aspect of the invention and a pharmaceutically acceptable carrier.

Preferably, the compound, e.g. fusion protein, may be formulated in phosphate buffered saline (PBS), in buffers containing arginine, citrate, mannitol, and/or Tween, or other standard protein formulation agents.

Advantageously, the composition is suitable for parenteral administration.

Conveniently, the formulation is a unit dosage containing a daily dose or unit, daily sub-dose or an appropriate fraction thereof, of the active compound.

The compounds of the invention will normally be administered orally or by any parenteral route, in the form of a pharmaceutical formulation comprising the active ingredient, optionally in the form of a non-toxic organic, or inorganic, acid, or base, addition salt, in a pharmaceutically acceptable dosage form. Depending upon the disorder and patient to be treated, as well as the route of administration, the compositions may be administered at varying doses.

In human therapy, the compounds of the invention can be administered alone but will generally be administered in admixture with a suitable pharmaceutical excipient diluent or carrier selected with regard to the intended route of administration and standard pharmaceutical practice.

For example, the compounds of the invention can be administered orally, buccally or sublingually in the form of tablets, capsules, ovules, elixirs, solutions or suspensions, which may contain flavouring or colouring agents, for immediate-, delayed- or controlled-release applications. The compounds of invention may also be administered via intracavernosal injection.

Such tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the compounds of the invention may be combined with various sweetening or flavouring agents, colouring matter or dyes, with emulsifying and/or suspending agents and with diluents such as water, ethanol, propylene glycol and glycerin, and combinations thereof.

The compounds of the invention can also be administered parenterally, for example, intravenously, intra-arterially, intraperitoneally, intrathecally, intraventricularly, intrasternally, intracranially, intra-muscularly or subcutaneously, or they may be administered by infusion techniques. They are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

The physician will determine the actual dosage which will be most suitable for any individual patient and it will vary with the age, weight and response of the particular patient. The dosages described in Example 9 are exemplary of the average case. There can, of course, be individual instances where higher or lower dosage ranges are merited and such are within the scope of this invention.

A sixth aspect of the invention provides a compound according to the first aspect of the invention for use in medicine.

A seventh aspect of the invention provides the use of a compound according to the first aspect of the invention in the preparation of a medicament for treating a patient with cancer.

An eighth aspect of the invention provides a method of treating a patient with cancer, the method comprising administering a compound according to the first aspect of the invention to said patient.

In principle, the compounds and compositions of the invention may be used to treat any mammal, including pets such as dogs and cats and agriculturally important animals such as cows, horses, sheep and pigs.

Preferably, however, the patient is human.

The compounds of the invention are particularly suited to the treatment of solid tumours, such as glioblastomas. Other preferred indications include ovarian, gastric, colorectal and pancreatic cancers.

The invention will now be described in detail with reference to the following non-limiting examples:

FIG. 1 shows a schematic diagram of preferred configurations of antibody variable regions (striped ovals), constant regions (white ovals), the IL-12 p35 subunit (small rectangles), the IL-12 p40 subunit (large rectangles), antibody hinges and linkers (thick lines) and disulfide bonds (thin lines). Particular preferred embodiments include intact IgG-type antibodies with p35 fused to the C-terminus of the heavy chain and p40 attached to p35 by a disulfide bond (FIG. 1A), a 'minibody' with the antibody V regions connected by a linker and attached through a hinge to a CH3 domain, and p35 fused to the C-terminus of the heavy chain and p40 attached to p35 by a disulfide bond (FIG. 1B), an sFv with p35 fused to a V region and p40 attached by a disulfide bond (FIG. 1C), and an Fab with p35 fused to a C region and p40 attached by a disulfide bond (FIG. 1D). The IL-12 p35 subunit may also be attached to the N-terminus of a V region. The IL-12 p40 subunit may be attached to p35 through a disulfide bond or through a linker, yielding a so-called 'single-chain IL-12' moiety (scIL-12).

FIG. 2 shows construct pdHL11-huBC1-M1-hup35 (see Example 1). The following features are depicted:

| Nucleotide positions | Description |
| --- | --- |
| 1 (EcoRI) to 664 (XbaI) | CMV enhancer and promoter |
| 664 (XbaI) to 1114 | genomic leader of a mouse immunoglobulin L chain |
| 1115 to 1439 | VL |
| 1440 (BamHI at 1447) to 1867 | Intron between VL and CL |
| 1868 to 2190 | CL coding region and translation stop codon |
| 2191 to 3054 (SalI) | 3' untranslated region and polyadenylation signal of the human immunoglobulin kappa chain gene |
| 3054(SalI) to 3721 (XhoI) | CMV enhancer and promoter |
| 3721 (XhoI) to 4176 | genomic leader of a mouse immunoglobulin L chain |
| 4177 to 4534 | VH |
| 4535 (HindIII at 4542) to 6347 | genomic sequence of human immunoglobulin γ1 gene constant region with deImmunised M1 at the fusion junction |
| 6348 to 6941 | Hu p35 coding region and translation stop codon |
| 6942 (XhoI at 6944) to 7190 | 3'-untranslated region and polyadenylation signal of SV40 late region |
| 7191 to 9484 (EcoRI) | origin of replication and β-lactamase gene from pBR322 |
| 9484 (EcoRI) to 9713 | Crippled SV40 enhancer and promoter |
| 9714 to 10277 | DHFR cDNA |
| 10278 to 10362 | 3'-untranslated region of DHFR fused to polyadenylation signal of SV40 early region via ligation of BglII sticky end to BclI sticky end |
| 10363 to 10599 | polyadenylation signal of SV40 early region |

FIG. 3 shows construct pNeo-CMV-hu p40 (see Example 1). The following features are depicted:

| Nucleotide positions | Description |
| --- | --- |
| 218 to 871 | CMV enhancer and promoter |
| 888 to 953 | Native signal peptide of hu p40 |
| 954 to 1874 | Hu p40 mature sequence and translation stop codon |
| 1884 to 2292 | Murine kappa polyadenylation signal |
| 2299 to 4591 | Origin of replication and β-lactamase gene from pBR322 |
| 3526 to 4386 | β-lactamase gene |
| 5630 to 6424 | Neomycin-resistant gene |

Figure 10:
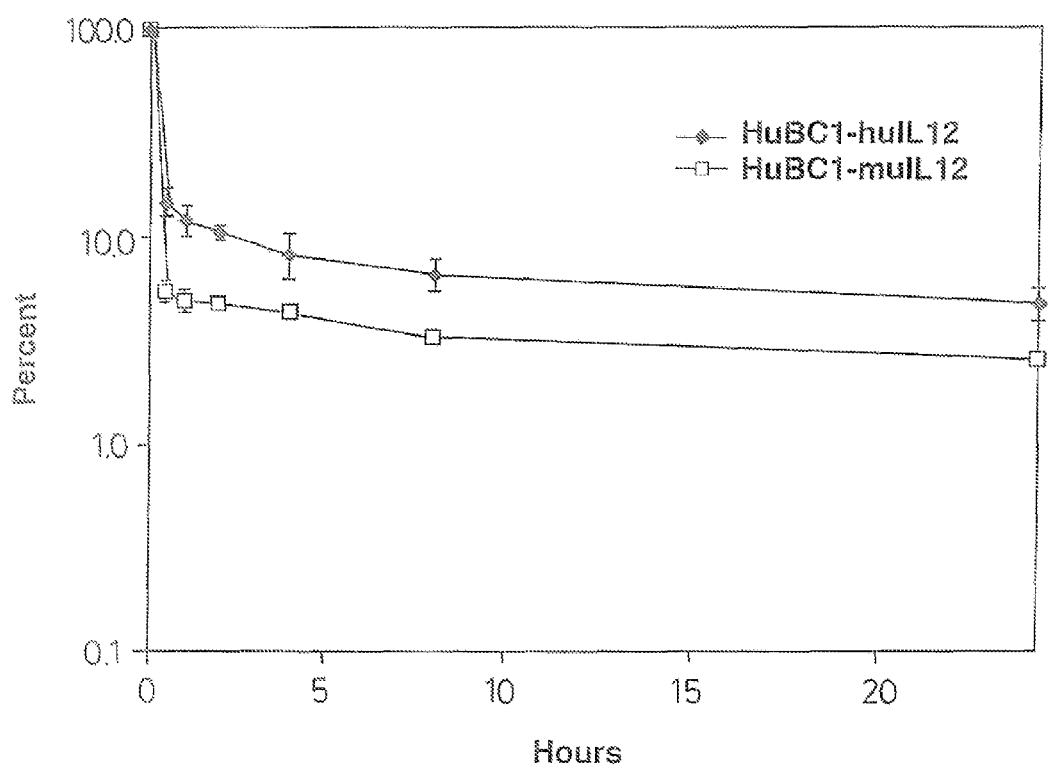

FIG. 10 shows a pharmacokinetic analysis of huBC1-muIL12 and huBC1-huIL12 in mice (see Example 5). BALB/c mice were injected with 25 mg of huBC1-IL12 in the tail vein. At various time points, small blood samples were taken by retro-orbital bleeding. The plasma was assayed by capture with anti-human IgG H&L antisera and detection with an anti-human or anti-murine IL12 antibody (R&D Systems). Results were normalised to the initial concentration in the serum of each mouse taken immediately after injection (t=0). The circulating half-life in mice is about 19 hr for both molecules.

EXAMPLES

Example 1

Production of huBC1-huIL12 Fusion Protein

I. Construction of the Expression Vectors for huBC1-huIL12
1. Variable Region of the Light Chain (VL)

The DNA encoding the variable region of the light chain (VL) of the humanised BC1 antibody was provided in the form of a plasmid, RKA.pMMR010. Polymerase chain reaction (PCR) was used to adapt the VL DNA for the expression vector pdHL11. The forward primer has the sequence 5'-C TTA AGC GAA ATT GTG TTG ACG CAG TC-3' [SEQ ID NO:11], where CTTAAG is an AflII restriction site and GAA is the N-terminal amino acid residue of the mature VL. The reverse primer has the sequence 5'-GGATCCACTTAC GTTTGATCTCCAGCTTGG-3' [SEQ ID NO:12], where the underlined sequence hybridised to the 3' end of the VL and GGATCC adds a BamHI restriction site downstream of the VL splice donor site.

A genomic signal peptide sequence from a mouse immunoglobulin light chain gene was used for secretion of the light and heavy chains of huBC1 fusion protein. A Kozak consensus sequence CCACCATGG was introduced for optimal ribosome binding for translation initiation at ATG [Kozak (1984) Nature 308:241]. This was achieved by mutating the first amino acid residue after the translation initiation codon from AAG to GAG to give the sequence TCTAGA CCACCATGGAG [SEQ ID NO:13], where the Kozak consensus sequence is underlined and an XbaI restriction site (TCTAGA) is placed at the 5' end.

At the 3' end of the signal peptide, the gene sequence encoding the –2 amino acid residue (the –1 amino acid being the C-terminal residue of the signal peptide) was mutagenised from a serine residue to a leucine residue (AGC to TTA) so that the DNA encoding the end of the signal peptide is CTTAAGC, where CTTAAG is a created AflII site [Lo et al. (1998) Protein Engineering 11:495]. Therefore, the signal peptide sequence contains a substitution at the first amino acid residue after the initiation codon and another substitution at the amino acid residue at the –2 position. Since the signal peptide is cleaved off by signal peptidase inside the cell and does not appear in the secreted protein, these mutations do not affect the composition of the antibody product. The 450-bp XbaI-AflII fragment containing the genomic signal peptide sequence was ligated to the AflII-BamHI fragment encoding the VL to give an XbaI-BamHI fragment, and this was in turn inserted into the pdHL11 expression vector, which already contains transcription regulatory elements and immunoglobulin constant region sequences (see below).

2. Variable Region of the Heavy Chain (VH)

The DNA encoding the variable region of the heavy chain (VH) of the humanised BC1 antibody was obtained in the form of a plasmid RHA.pGamma1. Polymerase chain reaction (PCR) was used to adapt the VH DNA for the expression vector pdHL11. The forward primer has the sequence 5'-C TTA AGC GAG GTG CAG CTG GTG CAG TC-3' [SEQ ID NO:14], where CTTAAG is an AflII restriction site and GAG is the N-terminal amino acid residue of the mature VH. The reverse primer has the sequence 5'-AAGCTTAC TTACCTGAGGAGACGGAGACC-3' [SEQ ID NO:15], where the underlined sequence hybridised to the 3' end of the VH and AAGCTT adds a HindIII restriction site downstream of the VH splice donor site.

Prior to ligation to the VH DNA, the XbaI site of the 450-bp XbaI-AflII fragment containing the genomic signal peptide sequence was converted to an XhoI site by linker ligation to give the sequence CCTCGAGGCTAGACCACCATGGAG [SEQ ID NO:16], where CCTCGAGG is the sequence of the XhoI linker, CTAGA is the XbaI sticky end made blunt by filling in with the Klenow fragment of DNA polymerase, and CCACCATGG is the Kozak consensus sequence. The XhoI-AflII restriction fragment containing the genomic leader was ligated to the AflII-HindIII fragment containing the VH gene, and the resultant XhoI-HindIII fragment was then inserted into the pdHL11 expression vector, which already contains transcription regulatory elements and immunoglobulin constant region sequences (see below).

3. Human Constant Regions

The light chain construct uses the constant region of the human kappa chain gene and the heavy chain construct uses the constant regions of the human gamma-1 chain. There is a SmaI restriction site located 280 bp upstream of the translation stop codon in the wild-type DNA sequence encoding the CH3 domain. This SmaI site was destroyed by the introduction of a silent mutation (TCC to TCA). Another silent mutation was introduced 10 bp upstream of the stop codon to create the sequence C CCG GGT AAA (STOP) [SEQ ID NO:17], which contains a new SmaI site [Lo et al. (1998) Protein Engineering 11:495]. This SmaI site is now unique in the pdHL11 expression vector and is used for as a fusion junction for creating antibody-cytokine fusion proteins.

4. cDNAs Encoding the p35 and p40 Subunits of Human IL-12

The cDNAs of p35 and p40 subunit of human IL12 were cloned from human peripheral blood monocytes (PBMC) using polymerase chain reactions (PCR). First strand cDNA was synthesised using an oligo dT primer and reverse transcriptase. The cDNA product was used as template for PCR. For the p35 subunit, the sense primer has the sequence 5'-CCAGAAAGCAAGA GACCAGAG-3' [SEQ ID NO:18], and the antisense primer has the sequence 5'-GGAGGGAC-CTCGAGTTTTAGGAAGCATTCAG-3' [SEQ ID NO:19]. The sense primer is derived from a sequence in the 5' untranslated region of the p35 message just upstream of a XmaI site, while the antisense primer encodes a translational stop codon followed shortly thereafter by a XhoI site for directional cloning. The primers for the p40 subunit cDNA were 5'-CTC-CGTCCTGTCT AGAGCAAGATGTGTC-3' [SEQ ID NO:20] for the sense and 5'-GCTTCTCGAGAACCTAACT-GCAGGGCACAG-3' [SEQ ID NO:21] for the antisense primer. The sense primer adds a unique XbaI site upstream of the translation start site while the antisense primer adds a XhoI site downstream of the translation stop codon.

5. Construction of huBC1-H Chain-Human p35 DNA

The cloned p35 cDNA, after sequence confirmation, was adapted for expression as a fusion protein as follows. At the fusion junction, the C-terminal amino acid residue of the CH3 is lysine and the N-terminal residue of the mature p35 is arginine. To minimise proteolysis at the fusion junction with these two basic residues, both of them were mutagenised to alanine, which, in the case of IL2 immunocytokine, has been shown to extend serum half-life [Gillies et al. (2002) *Clin. Cancer Res.* 8:210]. For reconstruction of the fusion junction, there is a convenient BalI site just 11 base-pairs (bp) downstream of the mature N-terminus of p35. Hence a XmaI-BalI oligonucleotide linker consisting of sense strand 5'-CCG GGC GCC GCA AAC CTC CCC GTG G-3' [SEQ ID NO:22] and anti-sense strand 5'-C CAC GGG GAG GTT TGC GGC GC-3' [SEQ ID NO:23], where the GCC GCA [SEQ ID NO: 24] denote the two alanine substitutions, was synthesised and ligated to a BalI-XhoI restriction fragment encoding the rest of the p35 subunit. The resultant XmaI-XhoI fragment in turn was ligated to the unique XmaI site in the pdHL11 expression vector, forming the CH3-p35 fusion junction. The peptide sequence at the junction, LSLSPGAANLPV [SEQ ID NO: 25], where AA are the two alanine substitutions, is novel and potentially immunogenic. Indeed it contained a potential T helper cell epitope, which could be removed by mutating the LSLS [SEQ ID NO: 26] residues to ATAT [SEQ ID NO: 27], based on Biovation's technology called deImmunization. The resultant deImmunised fusion junction sequence is called M1. Therefore, the huBC1-H chain-M1-hu p35 DNA consists of the XhoI-HindIII fragment encoding the signal peptide-VH, the HindIII-XmaI fragment encoding the genomic human IgG1 H chain constant regions with the deImmunised junction, and the XmaI-XhoI fragment encoding the p35 subunit.

6. Expression Vector pdHL11-huBC1-hu p³⁵

The expression vector pdHL11 is derived from pdHL7, which had been described previously (Gillies et al. (1998) *J. Immunol.* 160:6195). As in pdHL7, the two transcriptional units for the L and H chains in pdHL11 contain the CMV enhancer-promoter [Boshart et al. (1985) *Cell* 41:521-530]. The DNA for the CMV enhancer-promoter was obtained from an AflIII-HindIII fragment of the commercially available pcDNAI (Invitrogen Corp., San Diego, Calif.). At the 3' end, the L chain uses the 3' untranslated region and polyadenylation signal of the human immunoglobulin kappa chain gene and the H chain uses the 3'-untranslated region and polyadenylation signal of the SV40 late region.

The major difference between pdHL7 and pdHL11 is in the transcription unit for the dihydrofolate reductase (DHFR) selection marker. The SV40 enhancer for this transcription unit was destroyed in pdHL11 as follows. There are two 72 bp repeats in the SV40 enhancer/promoter, and within each 72 bp is a SphI restriction site. Ligation of the SalI site 5' of the enhancer to the distal SphI site through an oligonucleotide linker-adaptor resulted in the deletion of 120 bp from the two 72 bp repeats. Such an enhancerless promoter should give a much lower expression level of the DHFR selection marker. This, in theory, should result in fewer stably transfected cell clones, which, in order to survive the drug selection, might have the plasmid integrated into an active transcription region of a chromosome so that sufficient DHFR was expressed from the enhancerless promoter. The genes of interest, driven by fully functional enhancers and promoters, should be expressed at even higher levels in this active transcription region. In addition, the orientation of this attenuated transcription unit was reversed in pdHL11, so that the CMV enhancer for the L chain cannot exert a direct effect on the distal SV40 promoter for the expression of DHFR.

Figure 1:
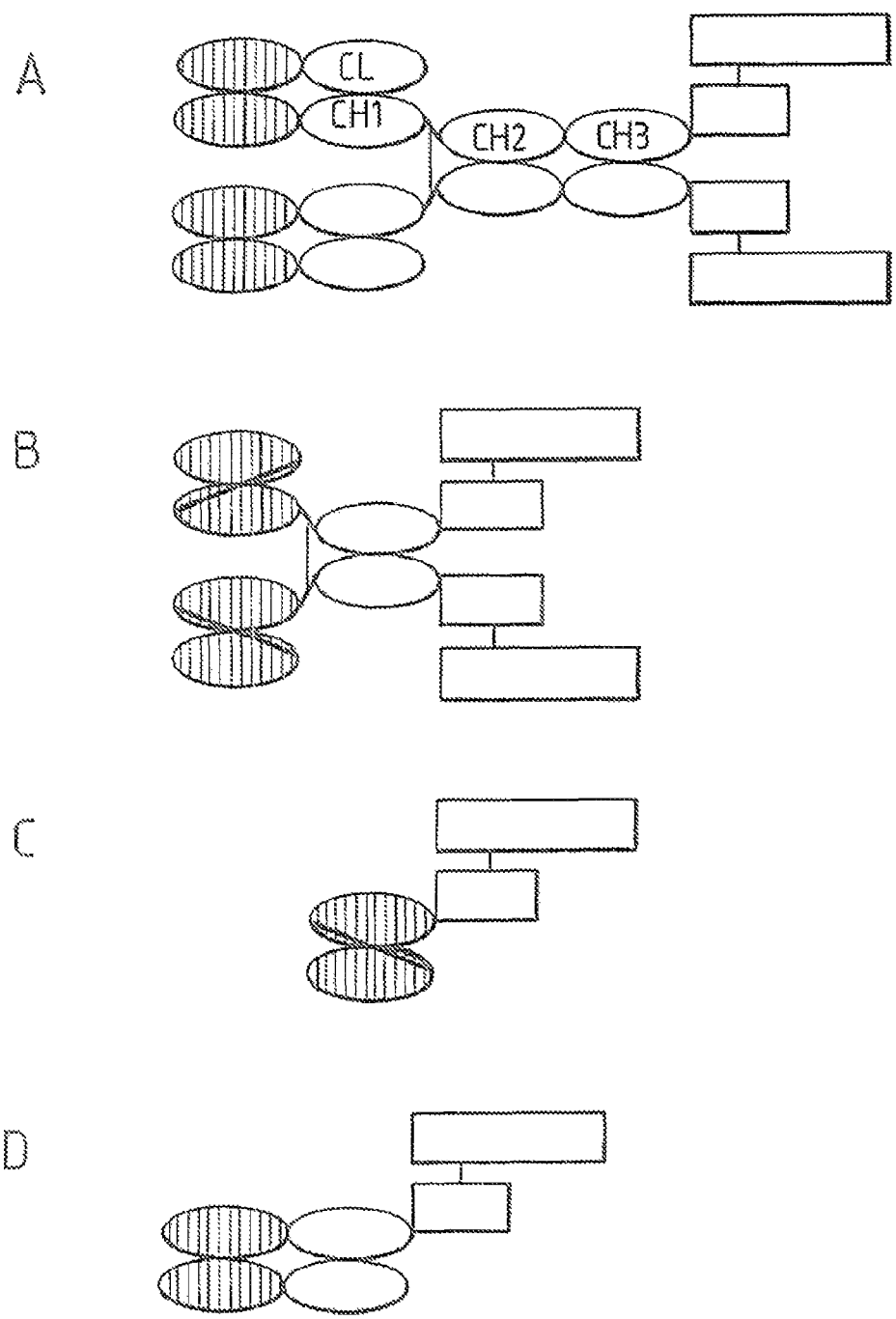
Figure 2:
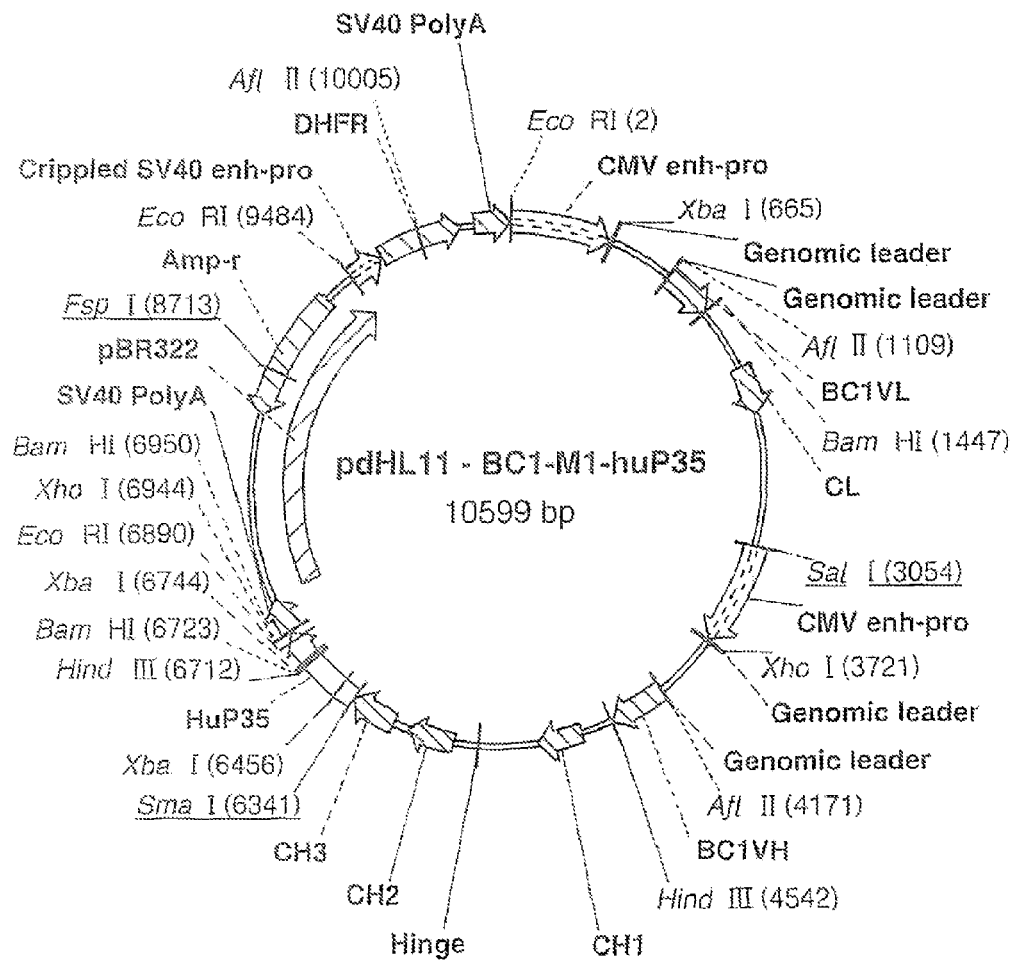

The construct pdHL11-huBC1-M1-hup35 was extensively mapped by restriction endonuclease digestions. The coding regions of the entire L and H chains were completely sequenced. Its salient features are depicted in FIG. 2.

7. Expression Vector for the hu p40 Subunit

The cloned p40 cDNA containing the complete open reading frame, after sequence confirmation, was ligated into a separate expression vector as an XbaI-XhoI fragment. This expression vector, pNeo-CMV-hu p40, contains a neomysin resistance gene for selection of transfected cells using the neomycin analog G418. The expression of the p40 is under the control of the CMV enhancer-promoter, and utilises the murine kappa polyadenylation signal.

Figure 3:
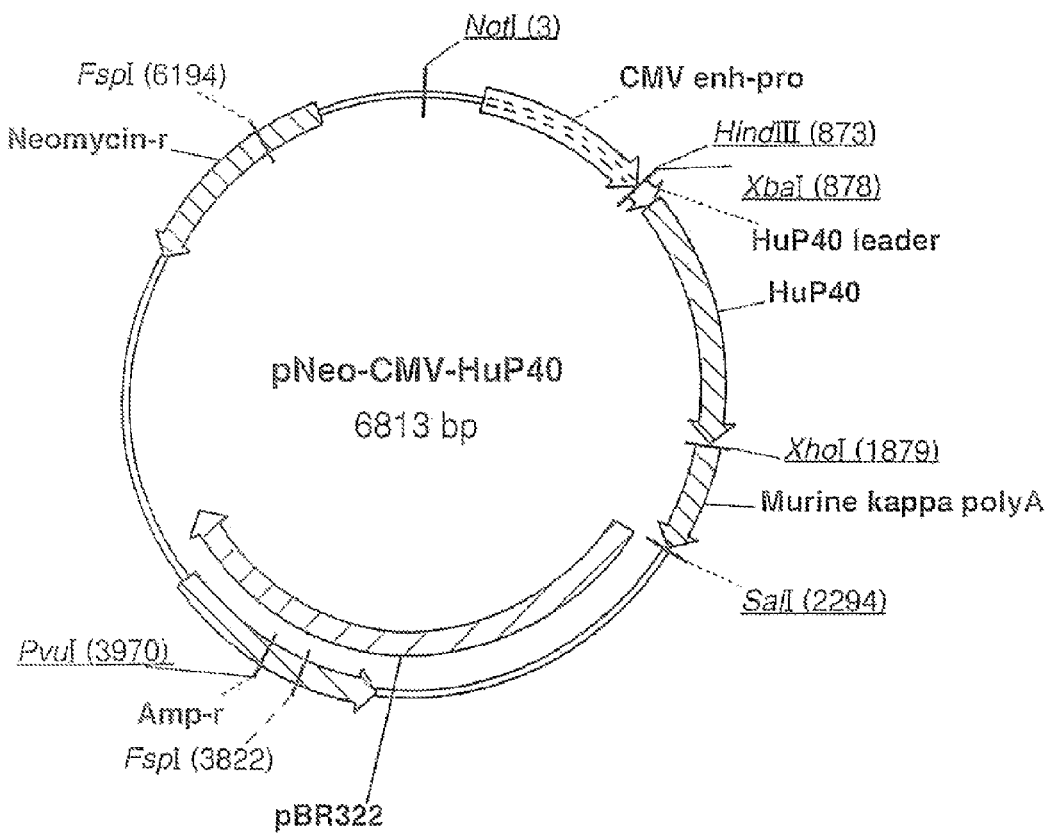

The construct pNeo-CMV-hu p40 was extensively mapped by restriction endonuclease digestions. Its salient features are depicted in FIG. 3.

II. DNA and Protein Sequences of huBC1-huIL12

1. Peptide and DNA Sequence of the Light Chain of huBC1-huIL12

The peptide sequence of the secreted light chain of the humanised BC1-huIL12 is as follows (VL is underlined):

[SEQ ID NO: 7]
EIVLTQSPGTLSLSPGERATLSCSASSSISSNYLHWYQQKPGQAPRLLIY

RTSNLASGIPDRFSGSGSGTDFTLTISRLEPEDFAVYYCQQGSSIPFTFG

QGTKLEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

The DNA sequences of the light chain construct, starting from the translation initiation codon ATG to the stop codon TAG, is given below. (VL is underlined; the upper and lower cases represent the coding and non-coding sequences, respectively):

[SEQ ID NO: 9]
ATGGAGTTGCCTGTTAGGCTGTTGGTGCTGATGTTCTGGATTCCTGgtga ggagagagggaagtgagggaggagaatggacagggagcaggagcactgaa tcccattgctcattccatgtatctggcatgggtgagaagatgggtcttat cctccagcatggggcctctggggtgaatacttgttagagggaggttccag atgggaacatgtgctataatgaagattatgaaatggatgcctgggatggt ctaagtaatgccttagaagtgactagacacttgcaattcactttttttgg taagaagagatttttaggctataaaaaaatgttatgtaaaaataaacgat cacagttgaaataaaaaaaaatataaggatgttcatgaatttttgtgtat aactatgtatttctctctcattgtttcagCTTCCTTAAGC<u>GAAATTGTGT</u>

<u>TGACGCAGTCTCCAGGCACCCTGTCTTTGTCTCCAGGGGAAAGAGCCACC</u>

<u>CTCTCCTGCAGTGCCAGTTCAAGTATAAGTTCCAATTACTTGCATTGGTA</u>

<u>CCAGCAGAAACCTGGCCAGGCTCCCAGGCTCCTCATCTATAGGACGTCCA</u>

<u>ATCTGGCTTCTGGCATCCCAGACAGGTTCAGTGGCAGTGGGTCTGGGACA</u>

<u>GACTTCACTCTCACCATCAGCAGACTGGAGCCTGAAGATTTTGCAGTGTA</u>

<u>TTACTGTCAGCAGGGTAGTAGTATACCATTCACGTTTGGCCAGGGGACCA</u>

<u>AGCTGGAGATCAAA</u>Cgtaagtggatcctatcagggttttacaagagggac taaagacatgtcagctatgtgtgactaatggtaatgtcactaagctgcgc gatcccgcaattctaaactctgaggggggtcggatgacgtggccattcttt gcctaaagcattgagtttactgcaaggtcagaaaagcatgcaaagccctc agaatggctgcaaagagctccaacaaaacaatttagaactttattaagga ataggggaagctaggaagaaactcaaaacatcaagattttaaatacgct tcttggtctccttgctataattatctgggataagcatgctgttttctgtc tgtccctaacatgccctgtgattatccgcaaacaacacacccaagggcag aactttgttacttaaacaccatcctgtttgcttctttcctcagGAACTGT

GGCTGCACCATCTGTCTTCATCTTCCCGCCATCTGATGAGCAGTTGAAAT

CTGGAACTGCCTCTGTTGTGTGCCTGCTGAATAACTTCTATCCCAGAGAG

GCCAAAGTACAGTGGAAGGTGGATAACGCCCTCCAATCGGGTAACTCCCA

GGAGAGTGTCACAGAGCAGGACAGCAAGGACAGCACCTACAGCCTCAGCA

GCACCCTGACGCTGAGCAAAGCAGACTACGAGAAACACAAAGTCTACGCC

TGCGAAGTCACCCATCAGGGCCTGAGCTCGCCCGTCACAAAGAGCTTCAA

CAGGGGAGAGTGTTAG

2. Peptide and DNA Sequence of the Heavy Chain of huBC1-huIL12

The peptide sequence of the secreted heavy chain huBC1-hup35 is as follows (VH is underlined, the deImmunised M1 junction in italics, and human p35 in bold):

[SEQ ID NO: 6]
<u>EVQLVQSGADVKKPGASVKVSCKASGYTFTNYVMHWVRQAPGQGLEWLGY</u>

<u>INPYNDGTQYNERFKGRVTMTGDTSISTAYMELSRLTSDDTAVYYCAREV</u>

<u>YGNYIWGNWGQGTLVSVSS</u>ASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKRVEPKSCDKTHTCPPCPAPELLGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSREEMTKNQVSLTCLVKGFYPSDIAVEWESNGQPENNYKTTPPVL

DSDGSFFLYSKLTVDKSRWQQGRVFSCSVMHEALHNHYTQKS*ATATPGAA*

NLPVATPDPGMFPCLHHSQNLLRAVSNMLQKARQTLEFYPCTSEEIDHED

ITKDKTSTVEACLPLELTKNESCLNSRETSFITNGSCLASRKTSFMMALC

LSSIYEDLKMYQVEFKTMNAKLLMDPKRQIFLDQNMLAVIDELMQALNFN

SETVPQKSSLEEPDFYKTKIKLCILLHAFRIRAVTIDRVMSYLNAS

The DNA sequences of the heavy chain huBC1-hu p35 construct, starting from the translation initiation codon ATG to the stop codon TAA, is given below (VH is underlined; the p35 sequence is in bold; and the upper and lower cases represent the coding and non-coding sequences, respectively):

[SEQ ID NO: 8]
ATGGAGTTGCCTGTTAGGCTGTTGGTGCTGATGTTCTGGATTCCTGgtga ggagagagggaagtgagggaggagaatggacagggagcaggagcactgaa tcccattgctcattccatgtatctggcatgggtgagaagatgggtcttat cctccagcatgggcctctggggtgaatacttgttagagggaggttccag atgggaacatgtgctataatgaagattatgaaatggatgcctgggatggt ctaagtaatgccttagaagtgactagacacttgcaattcactttttttgg taagaagagattttaggctataaaaaaatgttatgtaaaaataaacgat cacagttgaaataaaaaaaaaatataaggatgttcatgaattttgtgtat aactatgtatttctctctcattgtttcagCTTCCTTAAGC<u>GAGGTGCAGC</u>

<u>TGGTGCAGTCTGGGGCTGACGTGAAGAAGCCTGGGGCCTCAGTGAAGGTC</u>

<u>TCCTGCAAGGCTTCTGGATACACCTTCACCAACTACGTAATGCACTGGGT</u>

<u>GCGACAGGCCCCTGGACAAGGGCTTGAGTGGCTGGGATATATTAATCCTT</u>

<u>ACAATGATGGTACTCAGTACAATGAGAGGTTCAAAGGCAGGGTCACCATG</u>

<u>ACCGGGGACACGTCCATCAGTACAGCCTATATGGAGCTGAGCAGGCTGAC</u>

<u>TTCTGACGACACCGCGGTGTATTACTGTGCGAGAGAGGTCTATGGTAACT</u>

<u>ACATCTGGGGCAACTGGGGCCAGGGAACCCTGGTCTCCGTCTCCTCAG</u>gt aagtaagctttctggggcaggccaggcctgaccttggctttggggcaggg aggggggctaaggtgaggcaggtggcgccagccaggtgcacacccaatgcc catgagcccagacactggacgctgaacctcgcggacagttaagaacccag gggcctctgcgcctgggcccagctctgtcccacaccgcggtcacatggc accacctctcttgcagCCTCCACCAAGGGCCCATCGGTCTTCCCCCTGGC

ACCCTCCTCCAAGAGCACCTCTGGGGGCACAGCGGCCCTGGGCTGCCTGG

TCAAGGACTACTTCCCCGAACCGGTGACGGTGTCGTGGAACTCAGGCGCC

CTGACCAGCGGCGTGCACACCTTCCCGGCTGTCCTACAGTCCTCAGGACT

CTACTCCCTCAGCAGCGTGGTGACCGTGCCCTCCAGCAGCTTGGGCACCC

AGACCTACATCTGCAACGTGAATCACAAGCCCAGCAACACCAAGGTGGAC

AAGAGAGTTGgtgagaggccagcacagggagggagggtgtctgctggaag ccaggctcagcgctcctgcctggacgcatcccggctatgcagtcccagtc cagggcagcaaggcaggccccgtctgcctcttcacccggaggcctctgcc cgccccactcatgctcaggggagagggtcttctggcttttttccccaggctc tgggcaggcacaggctaggtgcccctaacccaggccctgcacacaaaggg gcaggtgctgggctcagacctgccaagagccatatccgggaggaccctgc ccctgacctaagcccaccccaaaggccaaactctccactccctcagctcg gacaccttctctcctcccagattccagtaactcccaatcttctctctgca gAGCCCAAATCTTGTGACAAAACTCACACATGCCCACCGTGCCCAGgtaa gccagcccaggcctcggcctccagctcaaggcgggacaggtgccctagag tagcctgcatccagggacaggccccagccgggtgctgacacgtccacctc catctcttcctcagCACCTGAACTCCTGGGGGACCGTCAGTCTTCCTCT

TCCCCCCAAAACCCAAGGACACCCTCATGATCTCCCGGACCCCTGAGGTC

ACATGCGTGGTGGTGGACGTGAGCCACGAAGACCCTGAGGTCAAGTTCAA

CTGGTACGTGGACGGCGTGGAGGTGCATAATGCCAAGACAAAGCCGCGGG

AGGAGCAGTACAACAGCACGTACCGTGTGGTCAGCGTCCTCACCGTCCTG

CACCAGGACTGGCTGAATGGCAAGGAGTACAAGTGCAAGGTCTCCAACAA

AGCCCTCCCAGCCCCCATCGAGAAACCATCTCCAAAGCCAAAGtggga cccgtggggtgcgagggccacatggacagaggccggctcggcccaccctc -continued
```
tgccctgagagtgaccgctgtaccaacctctgtccctacagGGCAGCCCC

GAGAACCACAGGTGTACACCCTGCCCCCATCACGGGAGGAGATGACCAAG

AACCAGGTCAGCCTGACCTGCCTGGTCAAAGGCTTCTATCCCAGCGACAT

CGCCGTGGAGTGGGAGAGCAATGGGCAGCCGGAGAACAACTACAAGACCA

CGCCTCCCGTGCTGGACTCCGACGGCTCCTTCTTCCTCTATAGCAAGCTC

ACCGTGGACAAGAGCAGGTGGCAGCAGGGGAACGTCTTCTCATGCTCCGT

GATGCATGAGGCTCTGCACAACCACTACACGCAGAAGAGCGCCACCGCGA

CCCCGGGCGCCGCAAACCTCCCCGTGGCCACTCCAGACCCAGGAATGTTC

CCATGCCTTCACCACTCCCAAAACCTGCTGAGGGCCGTCAGCAACATGCT

CCAGAAGGCCAGACAAACTCTAGAATTTTACCCTTGCACTTCTGAAGAGA

TTGATCATGAAGATATCACAAAAGATAAAACCAGCACAGTGGAGGCCTGT

TTACCATTGGAATTAACCAAGAATGAGAGTTGCCTAAATTCCAGAGAGAC

CTCTTTCATAACTAATGGGAGTTGCCTGGCCTCCAGAAAGACCTCTTTTA

TGATGGCCCTGTGCCTTAGTAGTATTTATGAAGACTTGAAGATGTACCAG

GTGGAGTTCAAGACCATGAATGCAAAGCTTCTGATGGATCCTAAGAGGCA

GATCTTTCTAGATCAAAACATGCTGGCAGTTATTGATGAGCTGATGCAGG

CCCTGAATTTCAACAGTGAGACTGTGCCACAAAAATCCTCCCTTGAAGAA

CCGGATTTTTATAAAACTAAAATCAAGCTCTGCATACTTCTTCATGCTTT

CAGAATTCGGGCAGTGACTATTGACAGAGTGACGAGCTATCTGAATGCTT

CCTAA
```

3. Peptide and DNA Sequence of the p40 Subunit

The peptide sequence of the secreted human p40 subunit is as follows:

```
[SEQ ID NO: 4]
IWELKKDVYVVELDWYPDAPGEMVVLTCDTPEEDGITWTLDQSSEVLGSG

KTLTIQVKEFGDAGQYTCHKGGEVLSHSLLLLHKKEDGIWSTDILKDQKE

PKNKTFLRCEAKNYSGRFTCWWLTTISTDLTFSVKSSRGSSDPQGVTCGA

ATLSAERVRGDNKEYEYSVECQEDSACPAAEESLPIEVMVDAVHKLKYEN

YTSSFFIRDIIKPDPPKNLQLKPLKNSRQVEVSWEYPDTWSTPHSYFSLT

FCVQVQGKSKREKKDRVFTDKTSATVICRKNASISVRAQDRYYSSSWSEW

ASVPCS
```

The DNA sequences of the p40 construct, starting from the translation initiation codon ATG to the stop codon TAG, is given below (The construct is a cDNA of the p40 mRNA. The DNA coding for its native signal peptide is in italics, and this is followed by DNA coding for the mature p40):

```
[SEQ ID NO: 10]
ATGTGTCACCAGCAGTTGGTCATCTCTTGGTTTTCCCTGGTTTTTCTGGC

ATCTCCCCTCGTGGCCATATGGGAACTGAAGAAAGATGTTTATGTCGTAG

AATTGGATTGGTATCCGGATGCCCCTGGAGAAATGGTGGTCCTCACCTGT

GACACCCCTGAAGAAGATGGTATCACCTGGACCTTGGACCAGAGCAGTGA

GGTCTTAGGCTCTGGCAAAACCCTGACCATCCAAGTCAAAGAGTTTGGAG

ATGCTGGCCAGTACACCTGTCACAAAGGAGGCGAGGTTCTAAGCCATTCG

CTCCTGCTGCTTCACAAAAAGGAAGATGGAATTTGGTCCACTGATATTTT

AAAGGACCAGAAAGAACCCAAAAATAAGACCTTTCTAAGATGCGAGGCCA

AGAATTATTCTGGACGTTTCACCTGCTGGTGGCTGACGACAATCAGTACT

GATTTGACATTCAGTGTCAAAAGCAGCAGAGGCTCTTCTGACCCCCAAGG

GGTGACGTGCGGAGCTGCTACACTCTCTGCAGAGAGAGTCAGAGGGGACA

ACAAGGAGTATGAGTACTCAGTGGAGTGCCAGGAGGACAGTGCCTGCCCA

GCTGCTGAGGAGAGTCTGCCCATTGAGGTCATGGTGGATGCCGTTCACAA

GCTCAAGTATGAAAACTACACCAGCAGCTTCTTCATCAGGGACATCATCA

AACCTGACCCACCCAAGAACTTGCAGCTGAAGCCATTAAAGAATTCTCGG

CAGGTGGAGGTCAGCTGGGAGTACCCTGACACCTGGAGTACTCCACATTC

CTACTTCTCCCTGACATTCTGCGTTCAGGTCCAGGGCAAGAGCAAGAGAG

AAAAGAAAGATAGAGTCTTCACGGACAAGACCTCAGCCACGGTCATCTGC

CGCAAAAATGCCAGCATTAGCGTGCGGGCCCAGGACCGCTACTATAGCTC

ATCTTGGAGCGAATGGGCATCTGTGCCCTGCAGTTAG
```

Example 2

Binding Characterisation (Study I)

Surface plasmon resonance and immunostaining experiments were performed to characterise the binding of an exemplary BC1-IL12 fusion protein of the invention to oncofoetal fibronectin.

In the course of characterising the binding of the BC1-IL12 fusion protein to its target antigen, it was found that this fusion protein bound more tightly to its target than did the corresponding BC1 antibody itself. For example, the binding of BC1 and BC1-IL12 to a polypeptide including human fibronectin domains 7, ED-B, 8, and 9 was measured using surface plasmon resonance. Table 1 summarises the results of two experiments.

TABLE 1

| | muBC1 (murine constant regions) | HuBC1 (human constant regions) | huBC1-IL12 |
|---|---|---|---|
| On-rate (1/mole/sec) | 1.65 × 10³ (exp. 2) | 6.2 × 10⁴ (exp. 1) 7.3 × 10⁴ (exp. 2) | 1.7 × 10⁴ (exp. 1) 1.9 × 10⁴ (exp. 2) |
| Off-rate | | 7.8 × 10⁻³ (exp. 1) | 1.3 × 10⁻³ (exp. 1) |

TABLE 1-continued

|  | muBC1 (murine constant regions) | HuBC1 (human constant regions) | huBC1-IL12 |
|---|---|---|---|
| (1/sec) | $1.1 \times 10^{-3}$ (exp. 2) | $1.0 \times 10^{-2}$ (exp. 2) | $1.6 \times 10^{-3}$ (exp. 2) |
| Dissociation constant (nM) | 686 | 125 (exp. 1)<br>138 (exp. 2) | 7.6 (exp. 1)<br>8.3 (exp. 2) |

The results indicate that the binding of huBC1-IL12 to its target antigen is at least 10-fold tighter, and most likely about 16-fold tighter, than the corresponding huBC1 antibody alone.

To confirm the results of the surface plasmon resonance study, U87 MG subcutaneous tumours were generated in immuno-compromised SCID CB17mice according to standard procedures, and tumour sections were immunostained with the huBC1 antibody and the huBC1-IL12 fusion protein. It was found that the intensity of staining with the huBC1-IL12 fusion protein was much greater than with the huBC1 antibody (data not shown).

Example 3

Binding Characterisation (Study II)

Introduction

Surface plasmon resonance (SPR) technology was used to demonstrate specificity of antigen binding (i.e. recognition of only the recombinant oncofoetal ibronectin, FN7B 89) and to determine/compare the kinetic rate constants/affinity values for both murine and humanized BC1 antibodies and BC1-IL12 Immunocytokines. All measurements reagents and software provided by Biocore.

Assay

ED-B negative (FN789) and ED-B positive (FN7B89) recombinant fibronectins (see 'Sequence information' below) were coupled on two different flow cells of a CM5 sensor chip using a standard amine coupling protocol and coupling reagents provided by Biacore. The other two flow cells were left blank and used a negative control surfaces. In order to demonstrate antigen specificity, the various BC1 antibodies and Immunocytokines were diluted to 500 nM in running buffer, HEPES Buffered Saline (HBS-EP). The samples were injected over the fibronectin-coupled surfaces for 5 min and the binding curves were compared. Running buffer (HBS-EP) was injected over each surface as a negative control to demonstrate baseline signal. The chip surfaces were regenerated with a 1 minute pulse of 0.1M HCl pH 1.5 followed by a second 1 minute pulse of $0.1M\ H_3PO_4$.

For kinetic analysis, only the ED-B positive fibronectin (FN7B89) was coupled to the chip. Three difference densities were coupled on three different flow cells. The fourth flow cell was left uncoupled and used as a negative control. Four to five concentrations of each molecule were prepared by performing twofold serial dilutions ranging from 1000 nM to 125 nM (muBC1), 200 nM to 25 nM (huBC1) and 100 nM to 6.25 nM (murine and humanized BC1-IL12). The serial dilutions were made in triplicate in the running buffer (HBS-EP). Each dilution was injected for 5 min (association) followed by 5 min of running buffer (dissociation) at a flow rate of 10 TL/min. The flow cells were regenerated as was done in the antigen specificity experiments described above. Curve fitting was done using software provided by Biacore.

Results

Figure 4:
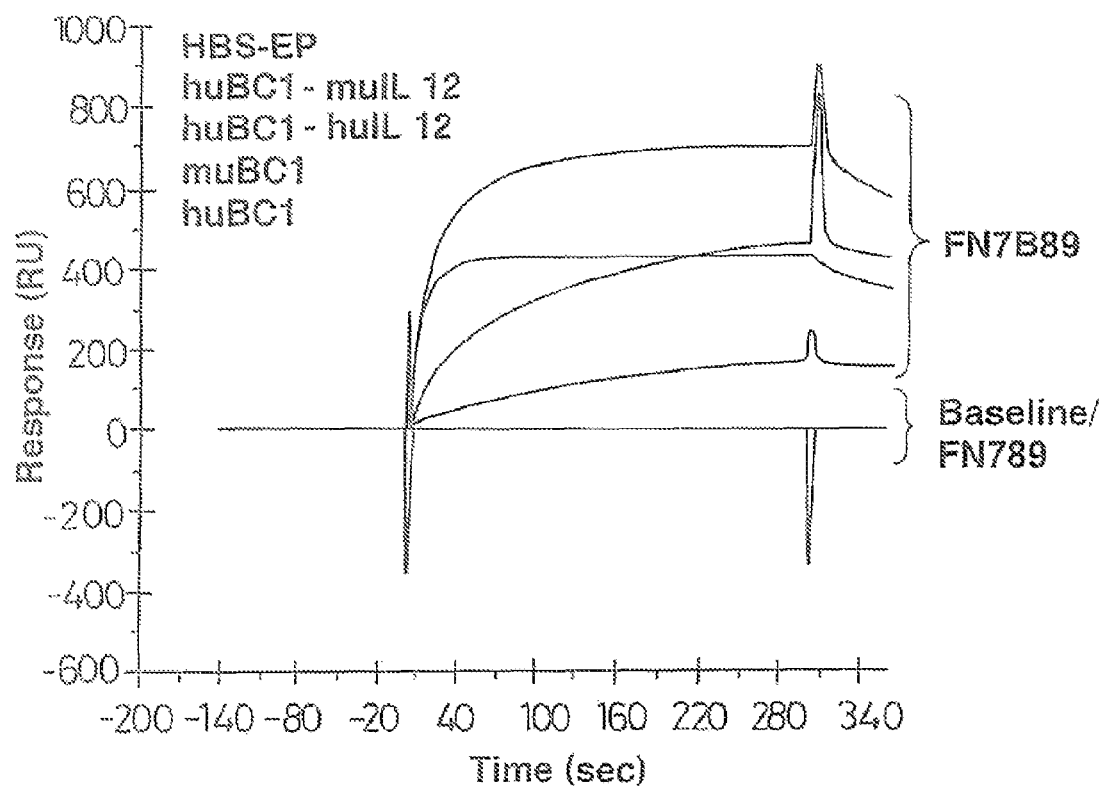
FIG. 4 shows the binding of four constructs (huBC1-muIL12, huBC1-huIL12, muBC1 and huBC1) to recombinant oncofoetal fibronectin fragments FN789 and FN7B89 (see Example 3).

While the various BC1 molecules bind with differing intensities to the recombinant oncofoetal fibronectin, FN7B89, they do not bind at all to the recombinant "normal" fibronectin, FN789 (see FIG. 4). This indicates that in all BC1 molecules tested, both antibodies and immunocytokines, have retained their antigen specificity (as compared to the original muBC1). These data also demonstrate that the kinetics of the antigen binding vary from molecule to molecule.

The kinetic analysis demonstrates that the rate constants do differ considerably between molecules (see Table 2).

TABLE 2

| Molecule | On-rate<br>$k_a$ ($\times 10^4\ M^{-1}s^{-1}$) | Off-rate<br>$k_d$ ($\times 10^{-3}\ s^{-1}$) | Affinity<br>$K_D$ (nm) |
|---|---|---|---|
| muBC1 | 0.17 | 0.65 | 377 |
| huBC1 | 5.76 | 3.12 | 54 |
| HuBC1-muIL12 | 7.95 | 1.09 | 13.9 |
| HuBC1-huIL12 | 5.09 | 0.87 | 17.3 |

Also, the BC1-IL12 immunocytokines have much higher affinity for FN7B89 than either the murine or human antibodies. Despite differences in the rate constants, huBC-1muIL12 and huBC1-huIL12 have essentially the same binding affinity for their antigen. These data indicate that the humanization of the BC1 antibody, as well as the subsequent generation of the BC1-IL12 immunocytokine, resulted in a molecule with increased affinity for the recombinant oncofoetal fibronectin.

Conclusions

All of the BC1 molecules specifically bind to the recombinant oncofoetal fibronectin, FN7B89, indicating that the constructions of the hyBC-huIL12 immunocytokine has not resulted in the loss of antigen specificity. Humanization of the BC1 murine antibody resulted in a molecule with increased binding affinity. This increase in the affinity is due to a significantly fast on-rate. The humanised antibody binds its antigen almost 34 times faster than its murine counterpart. However, humanization does have a negative impact as well. The off-rate for huBC1 is approximately 5 times faster than the muBC1. The addition of IL12 to the antibody, to create the BC1-IL12 immunocytokine, helps to off-set this, resulting in an off-rate similar to that seen from muBC1. In vitro, huBC1-huIL12 is a high affinity immunocytokine with the potential to be a potent tumour-targeting molecule in vivo.

Sequence Information (a) Fibronectin 789 fragment
```
LOCUS       FN789.DNA 1126 bp mRNA PRI 01-OCT-1999
DEFINITION  Human mRNA for fibronectin domains 789 (no ED-B) in pQE12 (pAS32)
NID         Derived from g31396 and pQE12 (Qiagen).
VERSION     X02761.1 GI:31396
KEYWORDS    alternate splicing; fibronectin.
SOURCE      human.
ORGANISM    Homo sapiens
            Eukaryota; Metazoa; Chordata; Craniata; Vertebrata; Mammalia;
            Eutheria; Primates; Catarrhini; Hominidae; Homo.

CDS         <208..1068
            /product = "Fn MRGS-789-HHHHHH"
            /translation = "
```
[SEQ ID NO: 28]

MRGSVVTPLSPPTNLHLEANPDTGVLTVSWERSTTPDI
TGYRITTTPTNGQQGNSLEEVVHADQSSCTFDNLSPGL
EYNVSVYTVKDDKESVPISDTIIPAVPPPTDLRFTNIG
PDTMRVTWAPPPSIDLTNFLVRYSPVKNEEDVAELSIS
PSDNAVVLTNLLPGTEYVVSVSSVYEQHESTPLRGRQK
TGLDSPTGIDFSDITANSFTVHWIAPRATITGYRIRHH
PEHFSGRPREDRVPHSRNSITLTNLTPGTEYVVSIVAL
NGREESPLLIGRSRSHHHHHH"

Note 1: Residue 1 to 207 is pQE sequence from and including Qiagen promoter
primer (CCCGAAAAGTGCCACCTG)[SEQ ID NO: 29]. Residue 1069 to 1126 is pQE12
sequence from the end of the hexa-histdine tag to the Qiagen reverse primer
sequence (GTTCTGAGGTCATTACTGG)[SEQ ID NO: 30]. Fibronectin- derived sequence
(i.e. without MRGS and hexa-histidine tag is in lower case).

Note 2: Please note that the coding sequence has mutations CC(230)A >
CA(230)A leading to a P8Q change; A(286)CA > G(286)CA leading to a T27A
change; and TCA(657) > TCG(657) leading to a silent S150S change.

BASE COUNT  319 a 297 c 226 g 284 t
ORIGIN

[SEQ ID NO: 31]
```
   1 CCCCGAAAAG TGCCACCTGA CGTCTAAGAA ACCATTATTA TCATGACATT AACCTATAAA
  61 AATAGGCGTA TCACGAGGCC CTTTCGTCTT CACCTCGAGA AATCATAAAA AATTTATTTG
 121 CTTTGTGAGC GGATAACAAT TATAATAGAT TCAATTGTGA GCGGATAACA ATTTCACACA
 181 GAATTCATTA AAGAGGAGAA ATTAACTATG AGAGGATCtg tggtgacacc attgtctcca
 241 ccaacaaact tgcatctgga ggcaaaccct gacactggag tgctcacagt ctcctgggag
 301 aggagcacca cccagacat tactggttat agaattacca caacccctac aaacggccag
 361 cagggaaatt cttttgaaga agtggtccat gctgatcaga gctcctgcac ttttgataac
 421 ctgagtcccg gcctggagta caatgtcagt gtttacactg tcaaggatga caaggaaagt
 481 gtccctatct ctgataccat catcccagct gttcctcctc ccactgacct gcgattcacc
 541 aacattggtc cagacaccat gcgtgtcacc tgggctccac cccatccat tgatttaacc
 601 aacttcctgg tgcgttactc acctgtgaaa aatgaggaag atgttgcaga gttgtcaatt
 661 tctccttcag acaatgcagt ggtcftaaca aatctcctgc ctggtacaga atatgtagtg
 721 agtgtctcca gtgtctacga acaacatgag agcacacctc ttagaggaag acagaaaaca
 781 ggtcttgatt cccaactgg cattgacttt tctgatatta ctgccaactc ttttactgtg
 841 cactggattg ctcctcgagc caccatcact ggctacagga tccgccatca tcccgagcac
 901 ttcagtggga gacctcgaga agatcgggtg ccccactctc ggaattccat caccctcacc
 961 aacctcactc caggcacaga gtatgtggtc agcatcgttg ctcttaatgg cagagaggaa
1021 agtcccttat tgattggcaG ATCCAGATCT CATCACCATC ACCATCACTA AGCTTAATTA
1081 GCTGAGCTTG GACTCCTGTT GATAGATCCA GTAATGACCT CAGAAC
//
```

(b) Fibronectin 7B89 fragment
```
LOCUS       FN7B89.DNA 1399 bp mRNA PRI 01-OCT-1999
DEFINITION  Human mRNA for fibronectin domains 7B89 in pQE12 (pAS33)
NID         Derived from g31396 and pQE12 (Qiagen).
VERSION     X02761.1 GI:31396
KEYWORDS    alternate splicing; fibronectin.
SOURCE      human.
ORGANISM    Homo sapiens
            Eukaryota; Metazoa; Chordata; Craniata; Vertebrata; Mammalia;
            Eutheria; Primates; Catarrhini; Hominidae; Homo.

CDS         <208..1341
            /product = "Fn MRGS-7B89-HHHHHH"
            /translation = "
```
[SEQ ID NO: 32]

MRGSVVTPLSPPTNLHLEANPDTGVLTVSWERSTTPDI
TGYRITTTPTNGQQGNSLEEVVHADQSSCTFDNLSPGL
EYNVSVYTVKDDKESVPISDTIIPEVPQLTDLSFVDIT

-continued

```
DSSIGLRWTPLNSSTIIGYRITVVAAGEGIPIFEDFVD
SSVGYYTVTGLEPGIDYDISVITLINGGESAPTTLTQQ
TAVPPPTDLRFTNIGPDTMRVTWAPPPSIDLTNFLVRY
SPVKNEEDVAELSISPSDNAVVLTNLLPGTEYVVSVSS
VYEQHESTPLRGRQKTGLDSPTGIDFSDITANSFTVHW
IAPRATITGYRIRHHPEHFSGRPREDRVPHSRNSITLT
NLTPGTEYVVSIVALNGREESPLLIGRSRSHHHHHH"
```

Note 1: Residue 1 to 207 is pQE sequence from and including Qiagen promoter primer (CCCGAAAAGTGCCACCTG)[SEQ ID NO: 29]. Residue 1342 to 1399 is pQE12 sequence from the end of the hexa-histidine tag to the Qiagen reverse primer sequence (GTTCTGAGGTCATTACTGG)[SEQ ID NO: 30]. Fibronectin-derived sequence (i.e. without MRGS and hexa-histidine tag is in lower case).

Note 2: Please note that the coding sequence has mutations CC(230)A > CA(230)A leading to a P8Q change; A(286)CA > G(286)CA leading to a T27A change; and TCA(930) > TCG(930) leading to a silent S241S change.

BASE COUNT 390 a 368 c 290 g 351 t
ORIGIN

[SEQ ID NO: 33]

```
   1 CCCCGAAAAG TGCCACCTGA CGTCTAAGAA ACCATTATTA TCATGACATT AACCTATAAA
  61 AATAGGCGTA TCACGAGGCC CTTTCGTCTT CACCTCGAGA AATCATAAAA AATTTATTTG
 121 CTTTGTGAGC GGATAACAAT TATAATAGAT TCAATTGTGA GCGGATAACA ATTTCACACA
 181 GAATTCATTA AAGAGGAGAA ATTAACTATG AGAGGATCtg tggtgacacc attgtctcca
 241 ccaacaaact tgcatctgga ggcaaaccct gacactggag tgctcacagt ctcctgggag
 301 aggagcacca ccccagacat tactggttat agaattacca caaccsctac aaacggccag
 361 cagggaaatt ctttggaaga agtggtccat gctgatcaga gctcctgcac ttttgataac
 421 ctgagtcccg gcctggagta caatgtcagt gtttacactg tcaaggatga caaggaaagt
 481 gtccctatct ctgataccat catcccagag gtgcccaac tcactgacct aagctttgtt
 541 gatataaccg attcaagcat cggcctgagg tggaccccgc taaactcttc caccattatt
 601 gggtaccgca tcacagtagt tgcggcagga gaaggtatcc ctattttga agattttgtg
 661 gactcctcag taggatacta cacagtcaca gggctggagc cgggcattga ctatgatatc
 721 agcgttatca tctccattaa tggcggcgag agtgcccta ctacactgac acaacaaacg
 781 gctgttcctc ctcccactga cctgcgattc accaacattg gtccagacac catgcgtgtc
 841 acctgggctc caccccatc cattgattta accaacttcc tggtgcgtta ctcacctgtg
 901 aaaaatgagg aagatgttgc agagttgtca atttctcctt cagacaatgc agtggtctta
 961 acaaatctcc tgcctggtac agaatatgta gtgagtgtct ccagtgtcta cgaacaacat
1021 gagagcacac ctcttagagg aagacagaaa acaggtcttg attccccaac tggcattgac
1081 ttttctgata ttactgccaa ctcttttact gtgcactgga ttgctcctcg agccaccatc
1141 actggctaca ggatccgcca tcatcccgag cacttcagtg ggagacctcg agaagatcgg
1201 gtgcccact ctcggaattc catcaccctc accaactca ctccaggcac agagtatgtg
1261 gtcagcatcg ttgctcftaa tggcagagag gaaagtccct tattgattgg caGATCCAGA
1321 TCTCATCACC ATCACCATCA CTAAGCTTAA TTAGCTGAGC TTGGACTCCT GTTGATAGAT
1381 CCAGTAATGA CCTCAGAAC
//
```

Materials and Methods

1. Materials: Biacore AB, Uppsala
catalog numbers and contact info available on website: www.biacore.com
Biacore 2000
BIAControl software (operates instrument)
BIAEvaluation software (data analysis)
Senior Chip CM5 (certified grade)
HBS-EP
Amine Coupling Kit 2. Kinetics Parameters: fit parameters selected in BIAEvaluation
curve Fit=bivalent (analyte is the antibody)
Start Injection=0 sec
Association=30-270 secs (4 min)
Stop Injection=300 sec
Dissociation=330-600 (4.5 min)

Example 4

In Vitro Testing of Efficacy in Cancer Therapy

To verify the utility of BC1-IL12 fusion proteins in treatment of cancer, an huBC1-muIL12 fusion protein was constructed and expressed according to standard procedures (see Example 1 and Gillies et al., WO99/29732, incorporated herein by reference). This protein used murine IL-12 because human IL-12 is not recognised by murine IL-12 receptors.

SCID CB17 mice bearing U87MG glioblastoma tumours with a volume of about 140 cubic millimetres were treated with either huBC1 or huBC1-IL12 as shown in Table 3.

TABLE 3

| Protein | Dose regimen | Tumour volume at day 8 | Tumour volume at day 13 |
|---|---|---|---|
| huBC1-IL12 | 20 mcg, day 0-7 | 85 | 60 |
| huBC1-IL12 | 5 mcg, day 0-7 | 130 | 120 |
| huBC1-IL12 | 5 mcg, day 0, 2, 4, 6, 10, 12 | 115 | 70 |
| huBC1 | 400 mcg, day 0, 4 | 170 | 175 |
| - (PBS) | Day 0-7 | 180 | 195 |

Example 5

Efficacy of huBC1-g1-muIL12 in Tumour Models in Mice

1. Introduction

The objective is to determine the efficacy of huBC1-IL12 in different tumour models in mice. HuBC1 (humanised BC1 antibody) targets the human fibronectin isoform, B-FN, that is present in the subendothelial extracellular matrix (ECM) of the neovasculature in vascularised tumours. B-FN is a good tumour marker because it is oncofoetal and angiogenesis-associated, and is undetectable in normal adult tissues. Since huBC-1 recognises only the human B-FN and does not cross-react with the murine B-FN, xenogeneic tumour models involving human tumour cells in severe combined immuno-deficient (SCID) mice and nude mice were used for preclinical studies. Furthermore, since IL12 is species-specific, the huBC1-huIL12 (humanised BC1 antibody-human IL12 fusion protein) intended for; humans does not work in mice. Therefore, we produced huBC1-murine IL12 as a surrogate drug candidate for evaluation in murine models.

2. Materials and Methods
2.1 Mouse Strains

SCID CB17 and Nude mice were purchased from Taconic, Charles River, and Jackson Lab.

2.2 Tumour Cell Lines

The human prostate adenocarcinoma PC3mm2 was a gift from Dr. Ralph Reisfeld at Scripps Research Institute. The human astrocytoma U-87 MG, the human epidermoid carcinoma A431 and the human colon carcinoma HT29 were obtained from American Type Culture Collection.

2.3 Proteins

HuBC1-g1-muIL12 is the same as huBC1-g1-M1-muIL12. It is a fusion protein of the humanised BC1 antibody with the human g1 constant regions and murine IL-12, and M1 is a deImmunised fusion junction (see Example 1 above).

HuBC1-g1-muIL12 was produced in a similar manner as huBC1-huIL12 (see Example 1 above), except that the mup40 and mup35 replaced the hup40 and hup35, respectively.

3. Experimental Design, Dosing Schedule and Evaluation
3.1 U-87MG Subcutaneous Model in SCID CB17 Mice
02-23 Effect of HuBC1-g1-M1-muIL12 Human U-87MG Astrocytoma Cells on Subcutaneous Model in SCID CB17 Mice Mice:
7-week-old SCID CB17 mice, male
Tumour Injection:
Inject the subcutaneous dorsa of SCID CB17 mice in the proximal midline with $4\times10^6$ viable U-87MG tumour cells in 0.1 ml PBS following the protocol.
Groups and Treatment:
Treatment starts when tumour size reaches ~100 mm$^3$. Mice are sorted into 5 groups (n=8) of mice with tumour volumes of equal mean and range:

| | | |
|---|---|---|
| 1. PBS | 0.2 ml | i.v. Day 0-8 |
| 2. HuBC1-g1-M1-MuIL12 | 20 µg | i.v. Day 0-8 |
| 3. HuBC1-g1-M1-MuIL12 | 5 µg | i.v. Day 0-8 |
| 4. HuBC1-g1-M1-MuIL12 | 20 µg | i.v. Every other day, for a total 12 doses |
| 5. HuBC1 Ab | 0.5 mg | i.p. Day 0 and 4 (3 mice only) |

Treat Evaluation:
Measure tumour size twice a week.
Determine tumour volume using formula width×length×height×0.5236.
Sacrifice any mice having tumour size over 5000 mm$^3$.
Calculate T/C ratio (the ratio of treated to control tumour volumes) at the appropriate time points.

3.2 A431 Subcutaneous Model in SCID CB17 Mice
02-37 Effect of BC1-g1-M1-muIL12 on A431 Subcutaneous Model in SCID CB17 Mice Mice:
8 week old SCID CB17 mice, male
Tumour Injection:
Inject the subcutaneous dorsa in the proximal midline of SCID CB17 mice with $1\times10^6$ viable A431 tumour cells in 0.1 ml PBS following the protocol.
Groups and Treatment:
Treatment starts when tumour size reaches ~100 mm$^3$. Mice are sorted into 2 groups (n=8) of mice with tumour volumes of equal mean and range:

| | | |
|---|---|---|
| 1. PBS | 0.2 ml | i.v. Day 0-7 |
| 2. HuBC1-muIL12 | 20 µg | i.v. Day 0-7 |

Evaluation:
Measure tumour size twice a week.
Determine tumour volume using formula width×length×height×0.5236.
Sacrifice any mice having tumour size over 5000 mm$^3$.
Calculate T/C ratio (the ratio of treated to control tumour volumes) at the appropriate time points.

3.3 PC3mm2 Subcutaneous Model in SCID CB17 Mice
02-44 Effect of BC1-g1-M1-muIL12 on PC3 mm2 Subcutaneous Model in SCID CB17 Mice Mice:
8 week old SCID CB17 mice, male
Tumour Injection:
Inject the subcutaneous dorsa in the proximal midline of SCID CB 17 mice with $2\times10^6$ viable PC3mm2 cells in 0.1 ml PBS following the protocol.
Groups and Treatment:
Treatment starts when tumour size reaches ~100 mm$^3$. Mice are sorted into 2 groups (n=7) of mice with tumour volumes of equal mean and range:

| | | |
|---|---|---|
| 1. PBS | 0.2 ml | i.v. day 0-6 |
| 2. BC1-g1-muIL12 | 20 µg | i.v. day 0-6 |

Evaluation:
Measure tumour size twice a week.
Determine tumour volume using formula width×length×height×0.5236.
Sacrifice any mice having tumour size over 5000 mm$^3$.
Calculate T/C ratio (the ratio of treated to control tumour volumes) at the appropriate time points.

3.4 HT-29 Subcutaneous Model in Nude Mice
02-70 Effect of HuBC1-g1-M1-muIL12 on HT-29 Subcutaneous Model in Nude Mice Mice:
6-7 week old nude mice (nu/nu), male
Tumour Injection:
Inject the subcutaneous dorsa of nude mice in the proximal midline with $1\times10^6$ viable HT-29 tumour cells in 0.1 ml PBS following the protocol.
Groups and Treatment:
Treatment starts when tumour size reaches ~100 mm$^3$. Mice are sorted into 2 groups (n=5) of mice with tumour volumes of equal mean and range:

| | | |
|---|---|---|
| 1. PBS | 0.2 ml | i.v. day 0-4 |
| 2. HuBC1-g1-muIL12 | 20 µg | i.v. day 0-4 |

Evaluation:
Measure tumour size twice a week.
Determine tumour volume using formula width$^2$×length× 0.5236.
Sacrifice any mice having tumour size over 5000 mm$^3$.
Calculate T/C ratio (the ratio of treated to control tumour volumes) at the appropriate time points.

3.5 PC3mm2 Lung Metastasis Model in SCID CB17 Mice
03-11 Effect of BC1-g1-M1-muIL12 on PC3mm2 Lung Metastasis Model in SCID CB17 Mice
Mice:
8-week-old SCID CB17 mice, male
Tumour Injection:
Inject mice with 2×10$^6$ viable single cells of PC3mm2 in 0.3 ml PBS i.v. on day 0.
Groups (n=8) and Treatment:

| 1. PBS | 0.2 ml | i.v. day 11-15 |
| 2. BC1-g1-M1-muIL12 | 16 μg | i.v. day 11-15 |
| 3. BC1-g1-M1-muIL12 | 8 μg | i.v. day 11-15 |

Termination:
Sacrifice mice on day 28 or when control mice become sick.
Remove lungs and fix them in Bouin's solution.
Measure lung weight and body weight.
Score lung metastases.
Check and record metastases on other organs and lymph nodes.

4. Results
4.1 U-87MG Subcutaneous Model in Immune Deficient SCID CB17 Mice

Figure 5A:
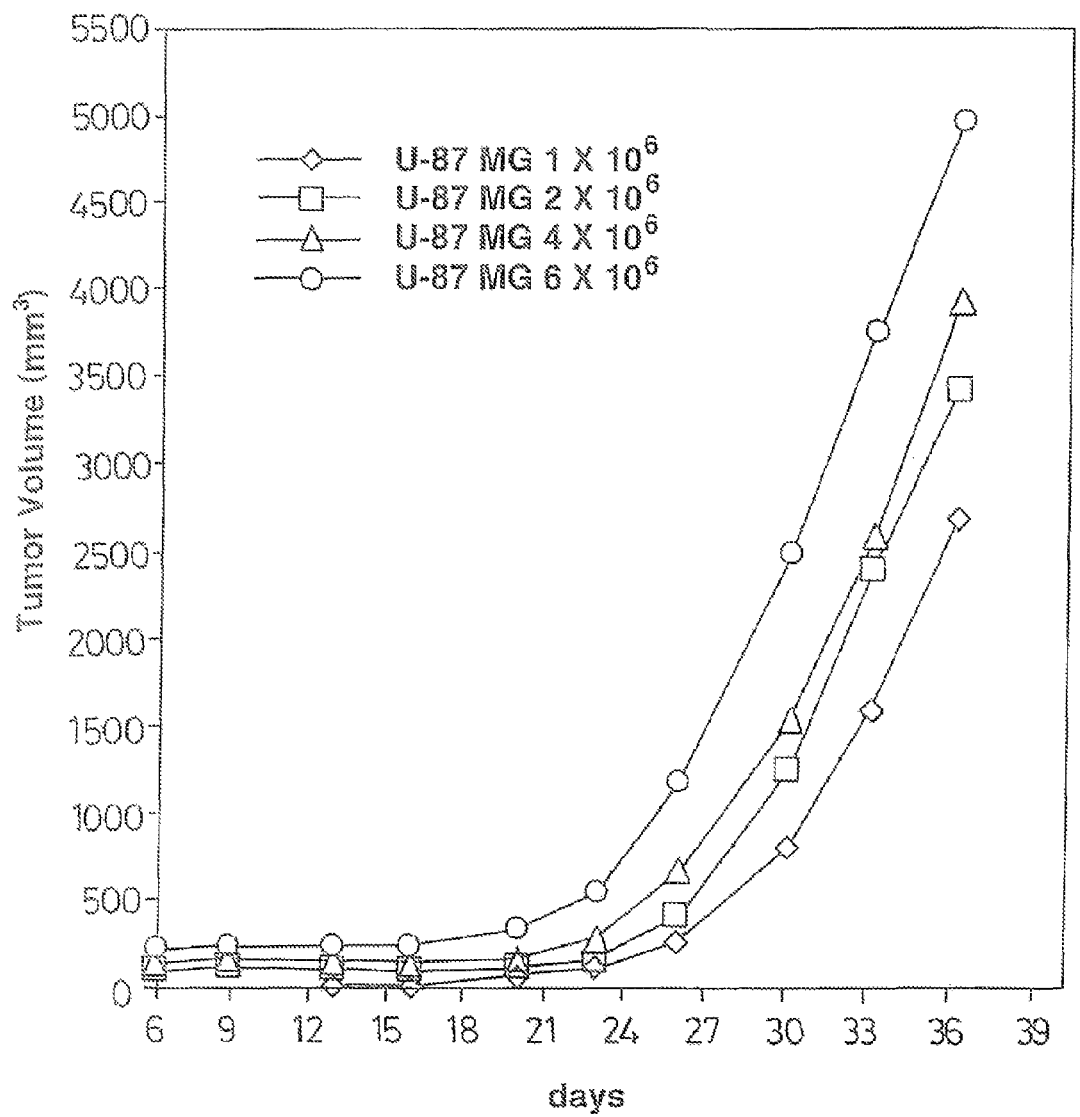
FIG. 5A shows a titration of number of U-87MG cells injected versus rate of growth of subcutaneous tumours (see Example 5).

First we had to establish a subcutaneous tumour model using the human astrocytoma U-87MG, chosen because of the high level of B-FN expression on this tumour cell line (Mariane et al., 1997, Cancer 80:2378). A titration was done to determine the number of cells to be injected for optimal tumour growth. Different numbers of viable cells (1 to 6×10$^6$) were injected into the back of each mouse to form skin tumours and their rates of growth were monitored (FIG. 5a). Interestingly, regardless of the number of cells injected, the rates of growth of the tumours remained flat for about 3 weeks, after which they all increased rapidly.

Figure 5B:
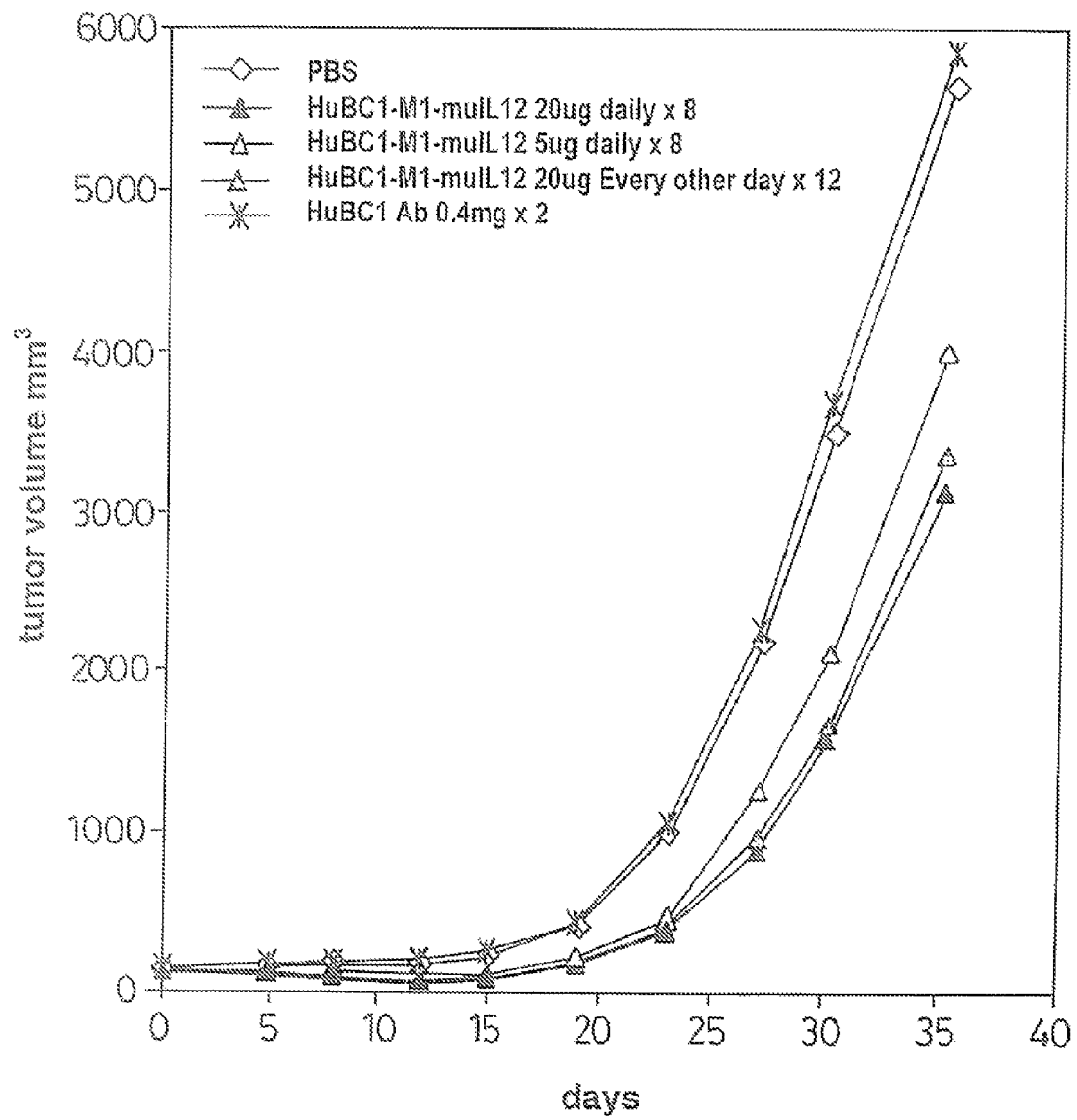
FIG. 5B shows the anti-tumour efficacy of huBC1-muIL12 in U87-MG subcutaneous model in SCID mice.

For the subsequent experiments, 4×10$^6$ viable cells were injected into the back of each mouse. Six days later, the average tumour size was about 135 mm$^3$, when treatment was initiated (Day 0). Two groups of mice were treated with 8 consecutive daily i.v. doses of either 5 or 20 μg of huBC1-muIL12. A third group received 20 μg of huBC1-muIL12. i.v. every other day, for a total 12 doses. For comparison, a fourth group of mice received 0.5 mg of huBC1 antibody i.p. on Day 0 and Day 4. Results of these 4 treatment groups and the control group receiving PBS are shown in FIG. 5b. The tumours in the PBS control group grew slowly to 430 mm$^3$ by Day 19, by which time the tumours switched to exponential growth, reaching an average size of 5627 mm$^3$ by Day 35. Treatment by the antibody had no effect on the tumour growth. Treatment by the different regimens of huBC1-muIL12 was effective for about 3 weeks in this immune deficient mouse model. By Day 23, the average tumour size of the group treated with 8 daily doses of 20 μg was about 446 mm$^3$, and the average tumour size of the two groups receiving the 80 μg doses was about 380 mm$^3$, as compared to over 1000 mm$^3$ for the PBS control group. However, the treatment only delayed the exponential growth phase by about 4 days, as from Day 23 to Day 35, the tumours in all three groups grew exponentially with a growth rate similar to the PBS treated group.

Table 4 shows average tumour volumes (in mm$^3$) of each group on different days.

TABLE 4

| Days | PBS | HuBC1-M1-muIL12 (20 μg daily × 8) | HuBC1-M1-muIL12 (5 μg daily × 8) | HuBC1-M1-muIL12 (20 μg every other day × 12) | HuBC1 Ab (0.4 mg daily × 2) |
|---|---|---|---|---|---|
| 0 | 133.6 | 134.3 | 134.8 | 135.6 | 144.4 |
| 5 | 163.7 | 123 | 135.5 | 133.4 | 169.9 |
| 8 | 175.7 | 91.1 | 125 | 113.8 | 184.2 |
| 12 | 180.3 | 66.3 | 115.6 | 75.9 | 194.9 |
| 15 | 232 | 88.8 | 100 | 91.9 | 255.4 |
| 19 | 429.8 | 215.1 | 191.9 | 178.2 | 425.8 |
| 23 | 1005.5 | 377.9 | 446.1 | 389.3 | 1059.9 |
| 27 | 2166.6 | 893.5 | 1263 | 976.4 | 2275.6 |
| 30 | 3474.7 | 1577.8 | 2106.2 | 1658.3 | 3664.5 |
| 35 | 5626.5 | 3122.2 | 3989 | 3347.4 | 5847.6 |

4.2 A431 Subcutaneous Model in SCID Mice

Figure 6:
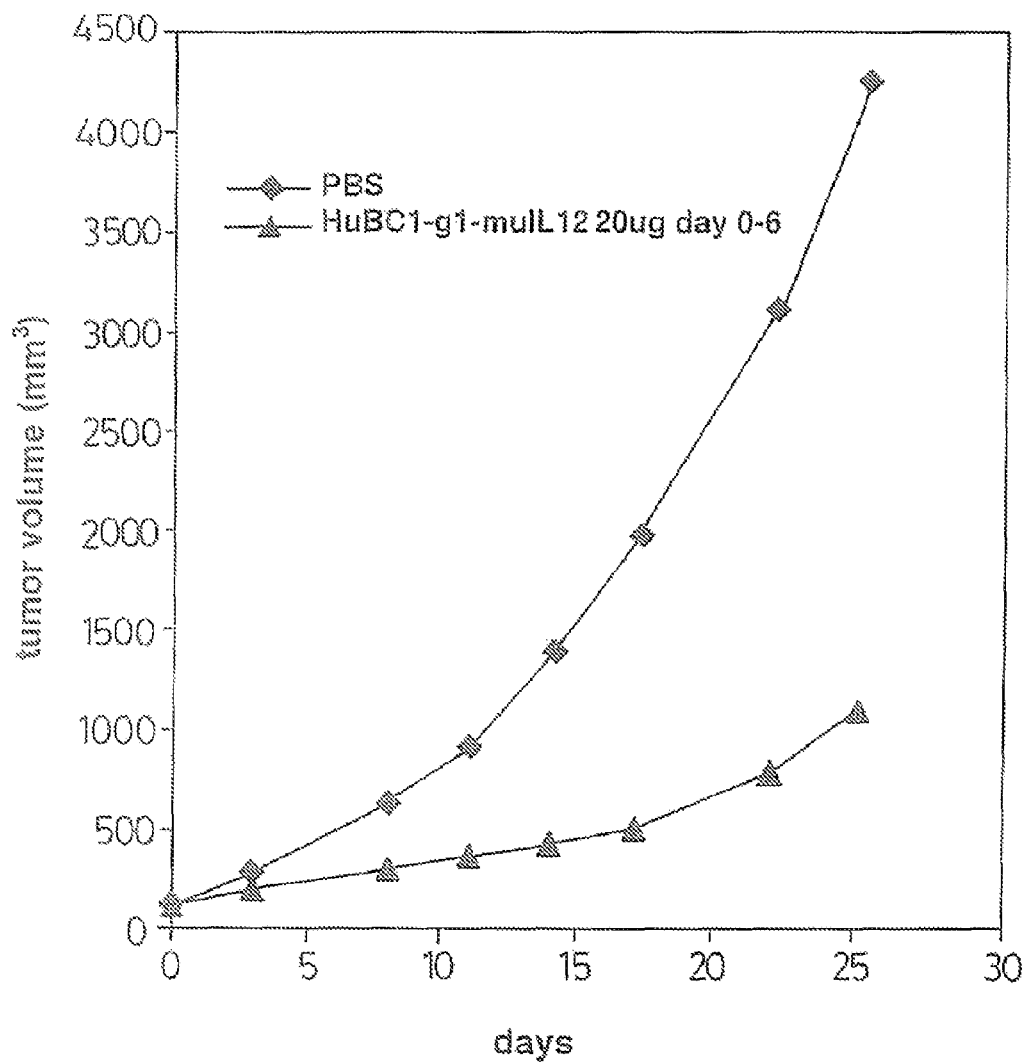
FIG. 6 shows the anti-tumour efficacy of huBC1-muIL12 in A431 subcutaneous model in SCID mice (see Example 5).

A single-cycle treatment of 7 consecutive daily i.v. doses of 20 μg of huBC1-muIL12 each was effective in the human melanoma A431 subcutaneous model in SCID mice, achieving a T/C ratio of 0.31 by Day 14 and 0.26 by Day 25 (see FIG. 6).

Table 5 shows average tumour volumes (in mm$^3$) of each group on different days.

TABLE 5

| Day | PBS | HuBC1-g1-MuIL12 (20 μg day 0-6) |
|---|---|---|
| 0 | 117.8 | 117.8 |
| 3 | 279.8 | 205.1 |
| 8 | 632.1 | 298.7 |
| 11 | 917.3 | 369.1 |
| 14 | 1390.9 | 425.0 |
| 17 | 1974.8 | 506.3 |
| 22 | 3108.1 | 780.3 |
| 25 | 4238.9 | 1093.3 |

4.3 PC3mm2 Subcutaneous Model in SCID Mice

Figure 7:
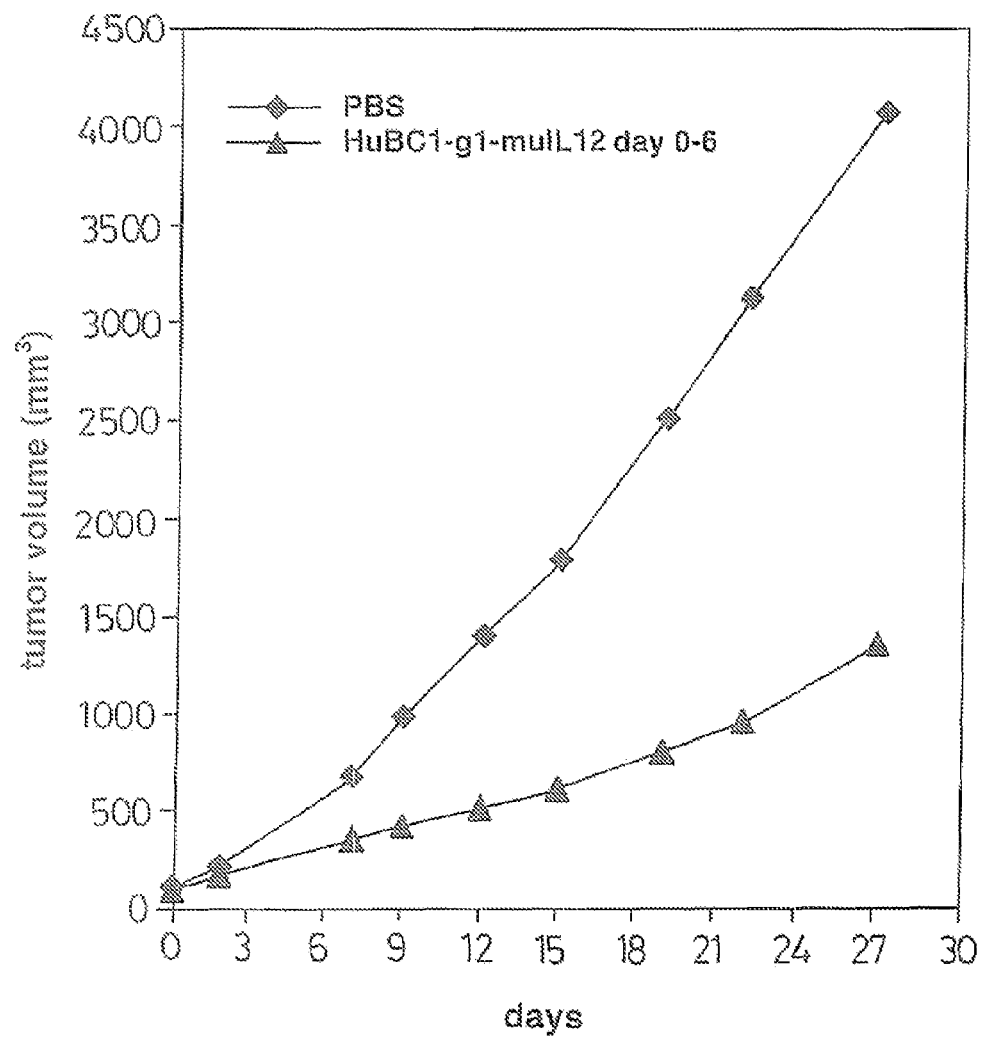
FIG. 7 shows the anti-tumour efficacy of huBC1-muIL12 in PC3mm2 subcutaneous model in SCID mice (see Example 5).

A single-cycle treatment of 7 consecutive daily i.v. doses of 20 μg of huBC1-muIL12 each was effective in the human prostate carcinoma PC3mm2 subcutaneous model in SCID mice, achieving a T/C ratio of 0.34 by Day 15 and 0.33 by Day 25 (see FIG. 7).

Table 6 shows average tumour volumes (in mm³) of each group on different days.

TABLE 6

| Day | PBS | HuBC1-g1-MuIL12 (20 µg day 0-6) |
|---|---|---|
| 0 | 109.9 | 109.7 |
| 2 | 224.3 | 184.7 |
| 7 | 678.8 | 363.7 |
| 9 | 988.7 | 435.8 |
| 12 | 1396.0 | 512.7 |
| 15 | 1777.8 | 608.3 |
| 19 | 2504.9 | 805.1 |
| 22 | 3115.8 | 963.4 |
| 27 | 4058.1 | 1351.3 |

4.4 HT-29 Subcutaneous Model in Nude Mice

Figure 8:
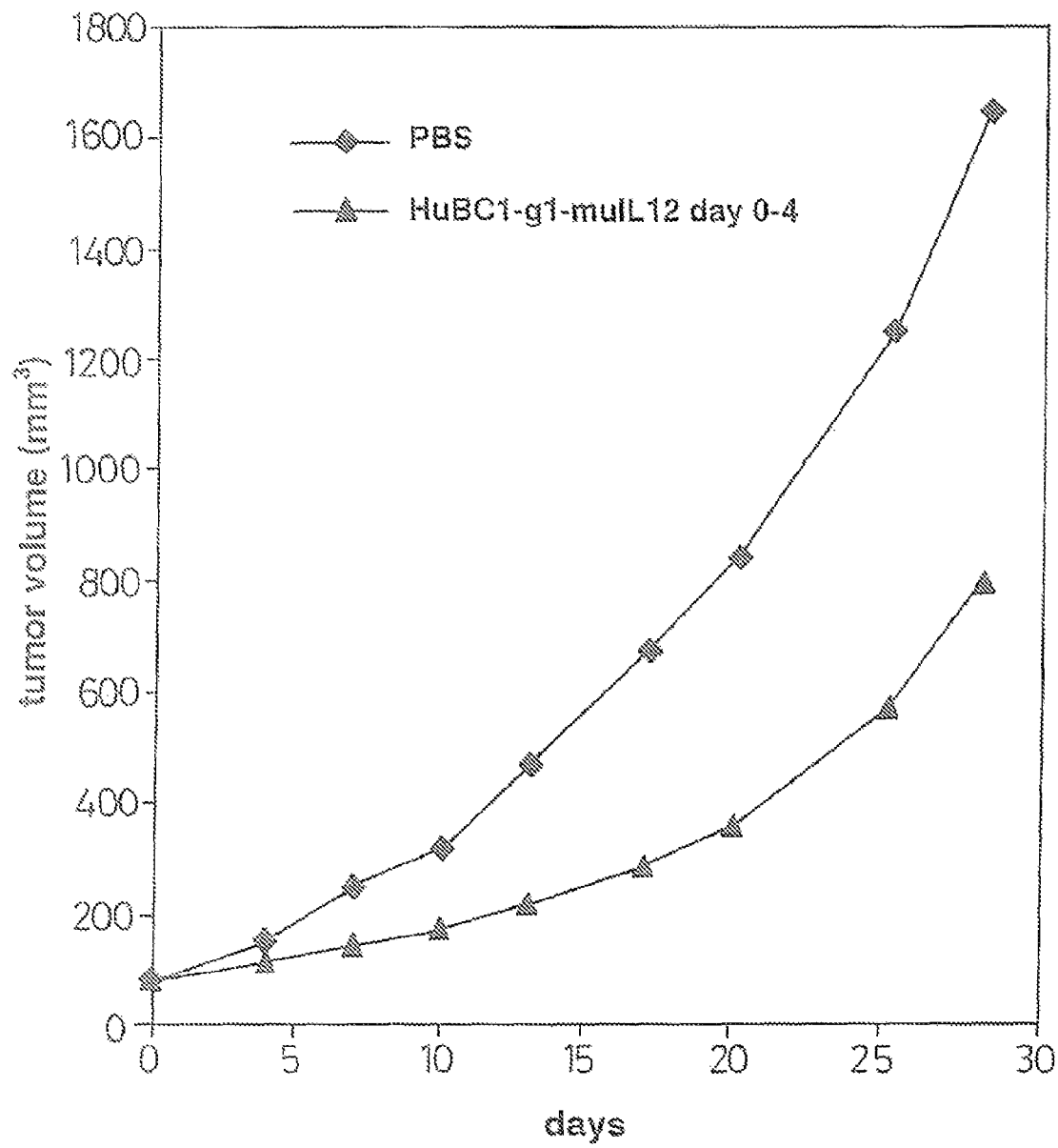
FIG. 8 shows the anti-tumour efficacy of huBC1-muIL12 in HT-29 subcutaneous model in SCID mice (see Example 5).

A single-cycle treatment of 5 consecutive daily i.v. doses of 20 µg of huBC1-muIL12 each was effective in the human prostate carcinoma PC3mm2 subcutaneous model in SCID mice, achieving a T/C ratio of 0.46 by Day 13 and 0.43 by Day 20 (see FIG. 8). Since it was only a single-cycle treatment and the nude mice lacked functional T cells, it was not too surprising that after Day 20, the rate of growth of the tumours in the treated group started to increase. It will be interesting to evaluate the benefits of a second cycle of treatment at this time.

Table 7 shows average tumour volumes (in mm³) of each group on different days.

TABLE 7

| Day | PBS | HuBC1-g1-MuIL12 (20 µg day 0-4) |
|---|---|---|
| 0 | 81.4 | 82.5 |
| 4 | 152.1 | 113.2 |
| 7 | 250.0 | 143.7 |
| 10 | 317.3 | 172.9 |
| 13 | 468.1 | 216.8 |
| 17 | 672.8 | 286.0 |
| 20 | 837.0 | 356.9 |
| 25 | 1248.3 | 570.2 |
| 28 | 1646.8 | 793.9 |

4.5 PC3mm2 Lung Metastasis Model in SCID Mice

Figure 9A:
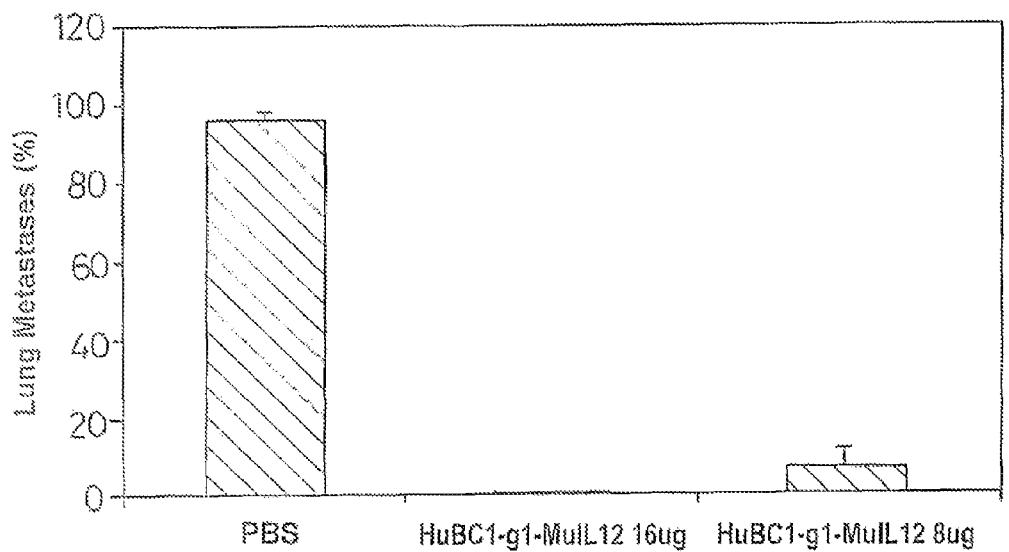
FIG. 9 shows the effect of huBC1-muIL12 administration on (A) lung surface covered by metastases and (B) lung weight human following injection of prostate carcinoma PC3mm2 cells into severe combined immunodeficient (SCID) mice (see Example 5).
Figure 9A:
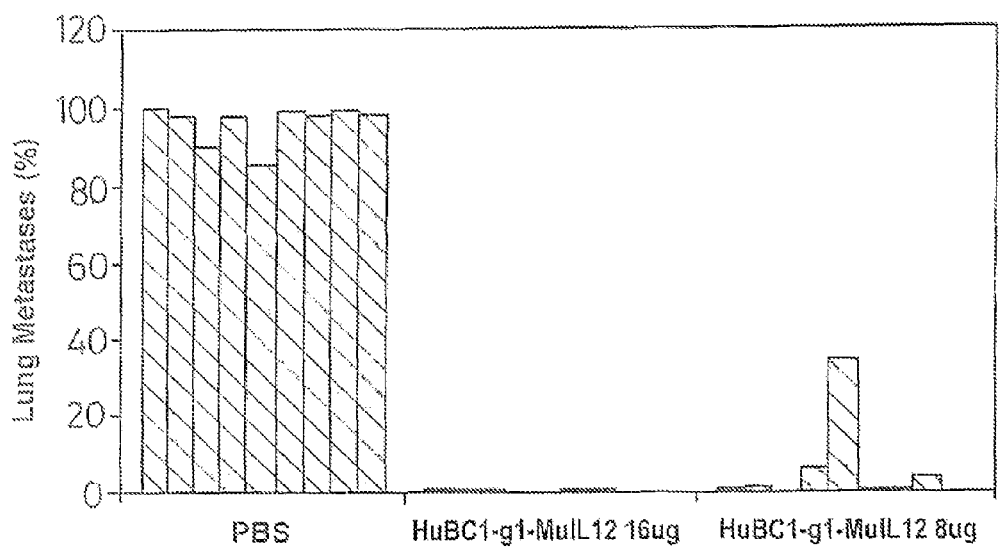
Figure 9B:
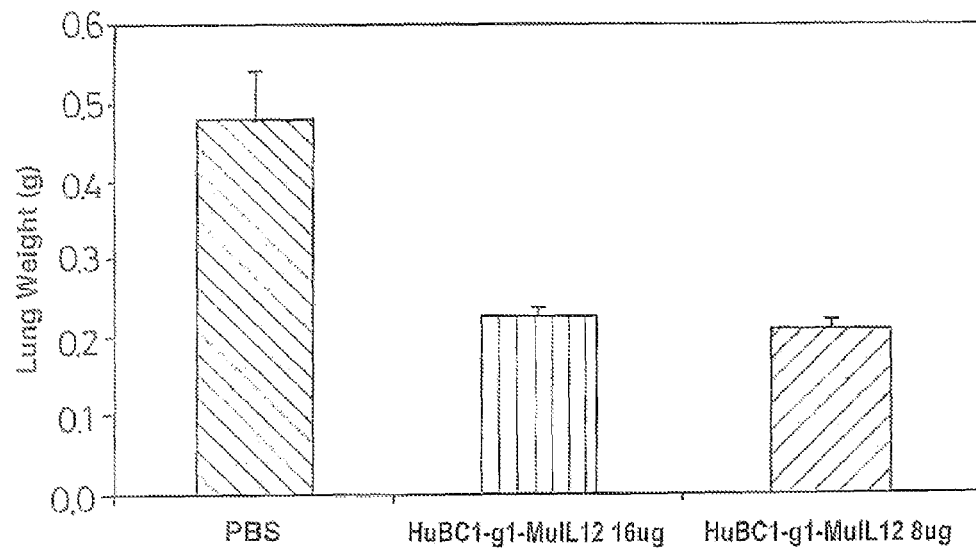
Figure 9B:
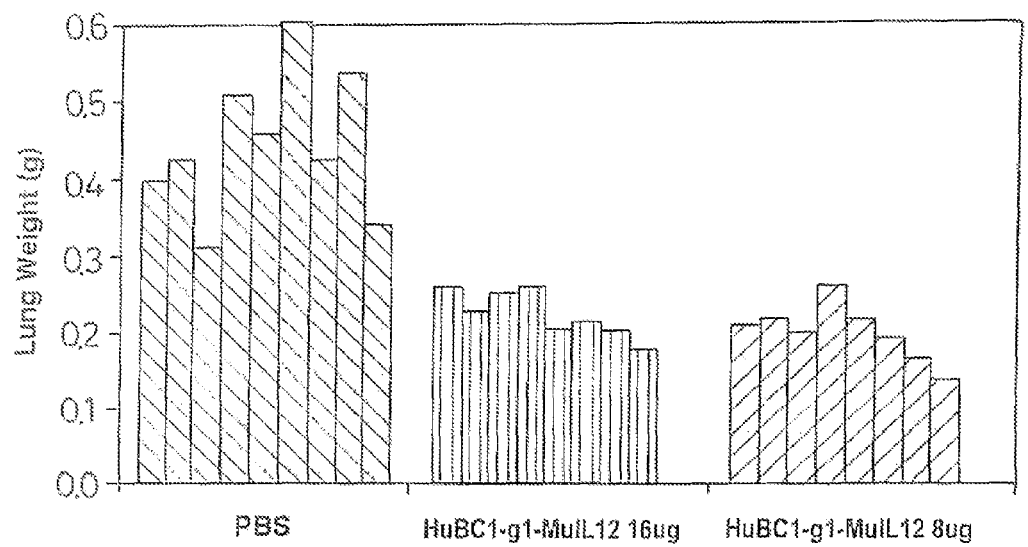

In this xenogeneic model, human prostate carcinoma PC3mm2 cells were injected into severe combined immunodeficient (SCID) mice 11 days before treatment began, allowing ample time for metastases to establish. Despite the lack of functional T and B cells in the SCID mice, 5 daily i.v. injections of huBC1-muIL12 at 16 µg almost completely eradicated the established metastases in all the mice and prevented their outgrowth, as measured by the lung surface covered by metastasis (FIG. 9A) and tumour burden (FIG. 9B). Even the 8 µg dosage was very effective, reducing the lung metastases by about 85%, relative to the PBS control.

Table 8 shows a summary of efficacy data of huBC1-muIL12 in mouse tumour models. The T/C for the subcutaneous (s.c.) tumours is the ratio of average tumour volume of the treated group over that of the PBS control group. For the lung metastasis model, the T/C is the average tumour burden of the treated group over that of the PBS control group.

TABLE 8

| Tumor | Model | Treatment | Dosage | T/C | P-Value (vs. ctr) |
|---|---|---|---|---|---|
| A431 Epidermoid Carcinoma | s.c. | BC1-γ1-MuIL12 | 20 µg; day 0-6 | 0.26 | 0.00038 on day 35 |
| HT-29 Colon Carcinoma | s.c. | BC1-γ1-MuIL12 | 20 µg; day 0-4 | 0.43 | 0.076 on day 28 |
| PC3mm2 Prostate adenocarcinoma | s.c. | BC1-γ1-MuIL12 | 20 µg; day 0-6 | 0.33 | 0.000039 on day 27 |
|  | lung met | BC1-γ1-MuIL12 | 16 µg; day 11-15 | 0.01/0.266 | 0.0028 on day 27 |
|  |  | BC1-γ1-MuIL12 | 8 µg; day 11-15 | 0 | 0.0016 |
|  |  | NHS-γ2h-MuIL12 | 8 µg; day 11-15 | 0.126/0.266 | 0.0084 |
| U87-MG Asreocytoma | s.c. | BC1-γ1-MuIL12 | 20 µg; day 0-7, 16-23 | 0.55 | 0.0027 on day 35 |
|  |  | BC1-γ1-MuIL12 | 5 µg; day 0-7, 16-23 | 0.71 | 0.022 |
|  |  | BC1-γ1-MuIL12 | 20 µg; q2d till day 22 | 0.59 | 0.012 |
|  |  | HuBC1 Ab | 0.4 mg; day 0, 4 | N/A | 0.89 |

5. Discussion

The drug candidate huBC1-huIL12 cannot be evaluated in current murine tumour models because human IL-12 is species-specific. Therefore, we produced huBC1-murine IL12 and showed that this surrogate molecule was efficacious in various xenogeneic metastasis and subcutaneous tumour models, as summarised in Table 8. In spite of the fact that SCID mice lacked functional T and B cells, a single cycle of treatment with 7 daily injections inhibited tumour growth by 74 and 67% respectively, in the A431 and PC3 models. Such results are impressive, especially in view of the fact that the huBC1-muIL12 had a very fast clearance rate in the α phase in mice, relative to huBC1-huIL12 (see FIG. 10 and Appendix below). A single cycle of treatment with 5 daily injections was also effective in the HT-29 model in nude mice, inhibiting tumour growth by 57%. Efficacy should improve with multiple-cycles of treatment with huBC1-huIL12 in the clinic, where patients undergoing or post-chemotherapy may have a more functional immune system than the SCID mice. In the PC3mm2 experimental lung metastasis model in SCID mice, 5 daily i.v. injections of huBC1-muIL12 at 16 µg nearly completely eradicated metastases which were allowed to establish for 11 days before treatment began.

6. Appendix: Pharmacokinetics of huBC1-muIL12 and huBC1-huIL12

Pharmacokinetics of huBC1-muIL12 and huBC1-huIL12 were measured in Balb/c mice. It was found that huBC1-huIL12 has a longer serum half-life than huBC1-muIL12 in mice, especially in the a phase (FIG. 10).

Example 9

Methods of Treatment

A compound, e.g. fusion protein, of the invention may be used as follows.

A patient suffering from a cancer, such as glioblastoma, is treated. The preferred route of administration is intravenous or subcutaneous injection, but intramuscular, intraperitoneal, intradermal, or other routes of injection are also possible. Administration by inhalation, orally, or by suppositories is also possible, as are other routes of administration. Administration is preferably in a four-week cycle of three times per week, followed by no treatment for the next three weeks, but may be more or less frequent depending on the pharmacokinetic behavior of the BC1-IL12 protein in a given individual. Dosing for an adult of about 70 kilograms is in the range of about 1 to 100 milligrams per dose, with a preferred range of about 4 to 20 milligrams per dose. The most preferred dose is about 10 milligrams for a 70 kg adult treated once per month. Patients are monitored for a response according to standard procedures.

---

The invention claimed is:

1. A compound comprising a target specific portion and an effector portion wherein:

(i) the target specific portion comprises a monoclonal antibody having specificity for oncofoetal fibronectin, or a fragment or variant thereof which retains the binding specificity for oncofoetal fibronectin of the parent monoclonal antibody; and (ii) the effector portion comprises interleukin-12, or a functional fragment or variant thereof;

wherein the target specific portion is capable of binding an amino acid sequence within the repeat 7 domain of fibronectin, wherein the compound comprises one or more polypeptides selected from the group consisting of the polypeptide of SEQ ID NO: 6 and the polypeptide of SEQ ID NO: 7, and wherein SEQ ID NO: 6 includes SEQ ID NO: 1 and SEQ ID NO: 3; and SEQ ID NO: 7 includes SEQ ID NO: 2.

2. A compound according to claim 1 wherein the compound comprises the polypeptide of SEQ ID NO:6 and the polypeptide of SEQ ID NO:7.

3. A compound according to claim 1 further comprising the polypeptide of SEQ ID NO:4 linked by at least one disulphide bond to the polypeptide of SEQ ID NO:6.

4. A pharmaceutical composition comprising a compound according to claim 1 and a pharmaceutically acceptable carrier.

5. A pharmaceutical composition according to claim 4 wherein the composition is suitable for parenteral administration.

6. A compound according to claim 1,
wherein the compound comprises the polypeptide of SEQ ID NO: 6, and further wherein:
the target specific portion further includes the polypeptide of SEQ ID NO: 2; and
the effector portion further includes the polypeptide of SEQ ID NO: 4 conjugated to SEQ ID NO: 3 by at least one disulphide bond;
and wherein the target specific portion is fused to the effector portion via the linker sequence that comprises the amino acid sequence ATATPGAA (SEQ ID NO: 5).

7. A compound according to claim 1, comprising:
the polypeptide of SEQ ID NO: 6;
the polypeptide of SEQ ID NO: 7 conjugated to the polypeptide SEQ ID NO: 6 by at least one disulphide bond; and
the polypeptide of SEQ ID NO: 4 conjugated to the polypeptide SEQ ID NO: 6 by a disulphide bond.

8. A compound comprising a target specific portion and an effector portion wherein:
(i) the target specific portion comprises a monoclonal antibody having specificity for oncofoetal fibronectin, or a fragment or variant thereof which retains the binding specificity for oncofoetal fibronectin of the parent monoclonal antibody; and
(ii) the effector portion comprises interleukin-12, or a functional fragment or variant thereof;
wherein the target specific portion is capable of binding an amino acid sequence within the repeat 7 domain of fibronectin, wherein:
the target specific portion comprises:
the polypeptide of SEQ ID NO: 1; and;
the polypeptide of SEQ ID NO: 2; and
the effector portion comprises:
an IL12p35 domain; and
an IL12p40 domain conjugated to the IL12p35 domain by at least one disulphide bond;
and wherein the target specific portion is fused to the effector portion via the linker sequence that comprises the amino acid sequence ATATPGAA (SEQ ID NO: 5).

9. The compound of claim 8, wherein the compound comprises a polypeptide selected from the group consisting of the polypeptide of SEQ ID NO: 6 and the polypeptide of SEQ ID NO: 7.

10. The compound of claim 1, wherein the compound comprises the polypeptide of SEQ ID NO: 7, and further wherein:
the target specific portion further includes includes:
the polypeptide of SEQ ID NO: 1; and
the effector portion comprises:
the polypeptide of SEQ ID NO: 3; and
the polypeptide of SEQ ID NO: 4 conjugated to SEQ ID NO: 3 by at least one disulphide bond;
and wherein the target specific portion is fused to the effector portion via the linker sequence that comprises the amino acid sequence ATATPGAA (SEQ ID NO: 5).

* * * * *

SEQUENCE LISTING

<160> NUMBER OF SEQ ID NOS: 33

<210> SEQ ID NO 1
<211> LENGTH: 119
<212> TYPE: PRT
<213> ORGANISM: Artificial Sequence
<220> FEATURE:
<223> OTHER INFORMATION: BC1 heavy chain variable region

<400> SEQUENCE: 1

Glu Val Gln Leu Val Gln Ser Gly Ala Asp Val Lys Lys Pro Gly Ala
1               5                   10                  15

Ser Val Lys Val Ser Cys Lys Ala Ser Gly Tyr Thr Phe Thr Asn Tyr
            20                  25                  30

Val Met His Trp Val Arg Gln Ala Pro Gly Gln Gly Leu Glu Trp Leu
        35                  40                  45

Gly Tyr Ile Asn Pro Tyr Asn Asp Gly Thr Gln Tyr Asn Glu Arg Phe
    50                  55                  60

Lys Gly Arg Val Thr Met Thr Gly Asp Thr Ser Ile Ser Thr Ala Tyr
65                  70                  75                  80

Met Glu Leu Ser Arg Leu Thr Ser Asp Asp Thr Ala Val Tyr Tyr Cys
                85                  90                  95

Ala Arg Glu Val Tyr Gly Asn Tyr Ile Trp Gly Asn Trp Gly Gln Gly
            100                 105                 110

Thr Leu Val Ser Val Ser Ser
        115

<210> SEQ ID NO 2
<211> LENGTH: 108
<212> TYPE: PRT
<213> ORGANISM: Artificial Sequence
<220> FEATURE:
<223> OTHER INFORMATION: BC1 light chain variable region

<400> SEQUENCE: 2

Glu Ile Val Leu Thr Gln Ser Pro Gly Thr Leu Ser Leu Ser Pro Gly
1               5                   10                  15

Glu Arg Ala Thr Leu Ser Cys Ser Ala Ser Ser Ser Ile Ser Ser Asn
            20                  25                  30

Tyr Leu His Trp Tyr Gln Gln Lys Pro Gly Gln Ala Pro Arg Leu Leu
        35                  40                  45

Ile Tyr Arg Thr Ser Asn Leu Ala Ser Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ser Ser Ile Pro
                85                  90                  95

Phe Thr Phe Gly Gln Gly Thr Lys Leu Glu Ile Lys
            100                 105

<210> SEQ ID NO 3
<211> LENGTH: 196
<212> TYPE: PRT
<213> ORGANISM: Artificial Sequence
<220> FEATURE:
<223> OTHER INFORMATION: IL-12p35 domain

<400> SEQUENCE: 3

Asn Leu Pro Val Ala Thr Pro Asp Pro Gly Met Phe Pro Cys Leu His
1               5                   10                  15

His Ser Gln Asn Leu Leu Arg Ala Val Ser Asn Met Leu Gln Lys Ala
            20                  25                  30

Arg Gln Thr Leu Glu Phe Tyr Pro Cys Thr Ser Glu Glu Ile Asp His
        35                  40                  45

Glu Asp Ile Thr Lys Asp Lys Thr Ser Thr Val Glu Ala Cys Leu Pro
    50                  55                  60

Leu Glu Leu Thr Lys Asn Glu Ser Cys Leu Asn Ser Arg Glu Thr Ser
65                  70                  75                  80

Phe Ile Thr Asn Gly Ser Cys Leu Ala Ser Arg Lys Thr Ser Phe Met
                85                  90                  95

Met Ala Leu Cys Leu Ser Ser Ile Tyr Glu Asp Leu Lys Met Tyr Gln
            100                 105                 110

Val Glu Phe Lys Thr Met Asn Ala Lys Leu Leu Met Asp Pro Lys Arg
        115                 120                 125

Gln Ile Phe Leu Asp Gln Asn Met Leu Ala Val Ile Asp Glu Leu Met
    130                 135                 140

Gln Ala Leu Asn Phe Asn Ser Glu Thr Val Pro Gln Lys Ser Ser Leu
145                 150                 155                 160

Glu Glu Pro Asp Phe Tyr Lys Thr Lys Ile Lys Leu Cys Ile Leu Leu
                165                 170                 175

His Ala Phe Arg Ile Arg Ala Val Thr Ile Asp Arg Val Met Ser Tyr
            180                 185                 190

Leu Asn Ala Ser
        195

<210> SEQ ID NO 4
<211> LENGTH: 306
<212> TYPE: PRT
<213> ORGANISM: Homo sapiens

<400> SEQUENCE: 4

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys

```
                    100                 105                 110
Asn Tyr Ser Gly Arg Phe Thr Cys Trp Trp Leu Thr Thr Ile Ser Thr
                115                 120                 125

Asp Leu Thr Phe Ser Val Lys Ser Ser Arg Gly Ser Ser Asp Pro Gln
            130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
            195                 200                 205

Asp Ile Ile Lys Pro Asp Pro Pro Lys Asn Leu Gln Leu Lys Pro Leu
            210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
            275                 280                 285

Gln Asp Arg Tyr Tyr Ser Ser Ser Trp Ser Glu Trp Ala Ser Val Pro
            290                 295                 300

Cys Ser
305

<210> SEQ ID NO 5
<211> LENGTH: 8
<212> TYPE: PRT
<213> ORGANISM: Artificial Sequence
<220> FEATURE:
<223> OTHER INFORMATION: Mutated Linker Sequence

<400> SEQUENCE: 5

Ala Thr Ala Thr Pro Gly Ala Ala
1               5

<210> SEQ ID NO 6
<211> LENGTH: 646
<212> TYPE: PRT
<213> ORGANISM: Artificial Sequence
<220> FEATURE:
<223> OTHER INFORMATION: BC1 heavy chain fused to IL-12p35

<400> SEQUENCE: 6

Glu Val Gln Leu Val Gln Ser Gly Ala Asp Val Lys Lys Pro Gly Ala
1               5                   10                  15

Ser Val Lys Val Ser Cys Lys Ala Ser Gly Tyr Thr Phe Thr Asn Tyr
            20

```
            85                  90                  95
Ala Arg Glu Val Tyr Gly Asn Tyr Ile Trp Gly Asn Trp Gln Gly
            100                 105                 110

Thr Leu Val Ser Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Arg Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
                355                 360                 365

Cys Leu Val Lys Gly Phe Tyr Pro Ser Asp Ile Ala Val Glu Trp Glu
                370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Ala Thr Ala Thr Pro Gly
                435                 440                 445

Ala Ala Asn Leu Pro Val Ala Thr Pro Asp Pro Gly Met Phe Pro Cys
450                 455                 460

Leu His His Ser Gln Asn Leu Leu Arg Ala Val Ser Asn Met Leu Gln
465                 470                 475                 480

Lys Ala Arg Gln Thr Leu Glu Phe Tyr Pro Cys Thr Ser Glu Glu Ile
                485                 490                 495

Asp His Glu Asp Ile Thr Lys Asp Lys Thr Ser Thr Val Glu Ala Cys
                500                 505                 510
```

```
Leu Pro Leu Glu Leu Thr Lys Asn Glu Ser Cys Leu Asn Ser Arg Glu
        515                 520                 525

Thr Ser Phe Ile Thr Asn Gly Ser Cys Leu Ala Ser Arg Lys Thr Ser
    530                 535                 540

Phe Met Met Ala Leu Cys Leu Ser Ser Ile Tyr Glu Asp Leu Lys Met
545                 550                 555                 560

Tyr Gln Val Glu Phe Lys Thr Met Asn Ala Lys Leu Leu Met Asp Pro
                565                 570                 575

Lys Arg Gln Ile Phe Leu Asp Gln Asn Met Leu Ala Val Ile Asp Glu
                580                 585                 590

Leu Met Gln Ala Leu Asn Phe Asn Ser Glu Thr Val Pro Gln Lys Ser
        595                 600                 605

Ser Leu Glu Glu Pro Asp Phe Tyr Lys Thr Lys Ile Lys Leu Cys Ile
    610                 615                 620

Leu Leu His Ala Phe Arg Ile Arg Ala Val Thr Ile Asp Arg Val Met
625                 630                 635                 640

Ser Tyr Leu Asn Ala Ser
                645

<210> SEQ ID NO 7
<211> LENGTH: 215
<212> TYPE: PRT
<213> ORGANISM: Artificial Sequence
<220> FEATURE:
<223> OTHER INFORMATION: BC1 light chain

<400> SEQUENCE: 7

Glu Ile Val Leu Thr Gln Ser Pro Gly Thr Leu Ser Leu Ser Pro Gly
1               5                   10                  15

Glu Arg Ala Thr Leu Ser Cys Ser Ala Ser Ser Ser Ile Ser Ser Asn
            20                  25                  30

Tyr Leu His Trp Tyr Gln Gln Lys Pro Gly Gln Ala Pro Arg Leu Leu
        35                  40                  45

Ile Tyr Arg Thr Ser Asn Leu Ala Ser Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ser Ser Ile Pro
                85                  90                  95

Phe Thr Phe Gly Gln Gly Thr Lys Leu Glu Ile Lys Arg Thr Val Ala
                100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 8
<211> LENGTH: 3205
<212> TYPE: DNA
<213> ORGANISM: Artificial Sequence
<220> FEATURE:
<223> OTHER INFORMATION: HuBC1 heavy chain fused to huIL12 p35 subunit

<400> SEQUENCE: 8

```
atggagttgc ctgttaggct gttggtgctg atgttctgga ttcctggtga ggagagaggg      60
aagtgaggga ggagaatgga cagggagcag gagcactgaa tcccattgct cattccatgt     120
atctggcatg ggtgagaaga tgggtcttat cctccagcat ggggcctctg ggtgaatac      180 ttgttagagg gaggttccag atgggaacat gtgctataat gaagattatg aaatggatgc     240
ctgggatggt ctaagtaatg ccttagaagt gactagacac ttgcaattca ctttttttgg     300
taagaagaga ttttaggct ataaaaaaat gttatgtaaa aataaacgat cacagttgaa      360
ataaaaaaaa aatataagga tgttcatgaa ttttgtgtat aactatgtat ttctctctca     420
ttgtttcagc ttccttaagc gaggtgcagc tggtgcagtc tggggctgac gtgaagaagc     480
ctggggcctc agtgaaggtc tcctgcaagg cttctggata caccttcacc aactacgtaa     540
tgcactgggt gcgacaggcc cctggacaag gcttgagtg ctgggatat attaatcctt       600 acaatgatgg tactcagtac aatgagaggt tcaaaggcag ggtcaccatg accggggaca     660
cgtccatcag tacagcctat atggagctga gcaggctgac ttctgacgac accgcggtgt     720
attactgtgc gagagaggtc tatggtaact acatctgggg caactggggc cagggaaccc     780
tggtctccgt ctcctcaggt aagtaagctt tctggggcag gccaggcctg accttggctt     840
tggggcaggg aggggctaa ggtgaggcag gtggcgccag ccaggtgcac acccaatgcc     900
catgagccca gacactggac gctgaacctc gcggacagtt aagaaccag ggcctctgc      960 gccctgggcc cagctctgtc ccacaccgcg gtcacatggc accacctctc ttgcagcctc    1020
caccaagggc ccatcggtct tccccctggc accctcctcc aagagcacct ctgggggcac    1080
agcggccctg ggctgcctgg tcaaggacta cttccccgaa ccggtgacgg tgtcgtggaa    1140
ctcaggcgcc ctgaccagcg gcgtgcacac cttcccggct gtcctacagt cctcaggact    1200
ctactccctc agcagcgtgg tgaccgtgcc ctccagcagc ttgggcaccc agacctacat    1260
ctgcaacgtg aatcacaagc ccagcaacac caaggtggac aagagagttg gtgagaggcc    1320
agcacaggga gggagggtgt ctgctggaag ccaggctcag cgctcctgcc tggacgcatc    1380
ccggctatgc agtcccagtc cagggcagca aggcaggccc cgtctgcctc ttcacccgga    1440
ggcctctgcc cgccccactc atgctcaggg agagggtctt ctggcttttt ccccaggctc    1500
tgggcaggca caggctaggt gcccctaacc caggccctgc acacaaaggg gcaggtgctg    1560
ggctcagacc tgccaagagc catatccggg aggaccctgc cctgaccta agcccaccc     1620 aaaggccaaa ctctccactc cctcagctcg gacaccttct ctcctcccag attccagtaa    1680
ctcccaatct tctctctgca gagcccaaat cttgtgacaa aactcacaca tgcccaccgt    1740
gcccaggtaa gccagcccag gcctcgccct ccagctcaag cgggacagg tgccctagag     1800 tagcctgcat ccagggacag gccccagccg ggtgctgaca cgtccacctc catctcttcc    1860
tcagcacctg aactcctggg ggaccgtca gtcttcctct tccccccaaa acccaaggac     1920
accctcatga tctcccggac ccctgaggtc acatgcgtgg tggtggacgt gagccacgaa    1980
gaccctgagg tcaagttcaa ctggtacgtg gacggcgtgg aggtgcataa tgccaagaca    2040
aagccgcggg aggagcagta caacagcacg taccgtgtgg tcagcgtcct caccgtcctg    2100
caccaggact ggctgaatgg caaggagtac aagtgcaagg tctccaacaa agccctccca    2160
```

-continued

```
gcccccatcg agaaaaccat ctccaaagcc aaaggtggga cccgtggggt gcgagggcca    2220
catggacaga ggccggctcg gcccacccte tgccctgaga gtgaccgctg taccaacctc    2280
tgtccctaca gggcagcccc gagaaccaca ggtgtacacc ctgcccccat acgggagga    2340 gatgaccaag aaccaggtca gcctgacctg cctggtcaaa ggcttctatc ccagcgacat    2400
cgccgtggag tgggagagca atgggcagcc ggagaacaac tacaagacca cgcctcccgt    2460
gctggactcc gacggctcct tcttcctcta tagcaagctc accgtggaca gagcaggtg     2520 gcagcagggg aacgtcttct catgctccgt gatgcatgag gctctgcaca accactacac    2580
gcagaagagc gccaccgcga ccccgggcgc cgcaaacctc cccgtggcca ctccagaccc    2640
aggaatgttc ccatgccttc accactccca aaacctgctg agggccgtca gcaacatgct    2700
ccagaaggcc agacaaactc tagaatttta cccttgcact tctgaagaga ttgatcatga    2760
agatatcaca aaagataaaa ccagcacagt ggaggcctgt ttaccattgg aattaaccaa    2820
gaatgagagt tgcctaaatt ccagagagac ctctttcata actaatggga gttgcctggc    2880
ctccagaaag acctctttta tgatggccct gtgccttagt agtatttatg aagacttgaa    2940
gatgtaccag gtggagttca agaccatgaa tgcaaagctt ctgatggatc ctaagaggca    3000
gatctttcta gatcaaaaca tgctggcagt tattgatgag ctgatgcagg ccctgaattt    3060
caacagtgag actgtgccac aaaaatcctc ccttgaagaa ccggatttt ataaaactaa    3120 aatcaagctc tgcatacttc ttcatgcttt cagaattcgg gcagtgacta ttgacagagt    3180
gacgagctat ctgaatgctt cctaa                                         3205
```

<210> SEQ ID NO 9
<211> LENGTH: 1516
<212> TYPE: DNA
<213> ORGANISM: Artificial Sequence
<220> FEATURE:
<223> OTHER INFORMATION: HuBC1 Light chain

<400> SEQUENCE: 9

```
atggagttgc ctgttaggct gttggtgctg atgttctgga ttcctggtga ggagagaggg     60
aagtgaggga ggagaatgga cagggagcag gagcactgaa tcccattgct cattccatgt    120
atctggcatg ggtgagaaga tgggtcttat cctccagcat ggggcctctg ggtgaatac     180 ttgttagagg gaggttccag atgggaacat gtgctataat gaagattatg aaatggatgc    240
ctgggatggt ctaagtaatg ccttagaagt gactagacac ttgcaattca ctttttttgg    300
taagaagaga tttttaggct ataaaaaat gttatgtaaa aataaacgat cacagttgaa     360
ataaaaaaaa aatataagga tgttcatgaa ttttgtgtat aactatgtat ttctctctca    420
ttgtttcagc ttccttaagc gaaattgtgt tgacgcagtc tccaggcacc ctgtctttgt    480
ctccagggga aagagccacc ctctcctgca gtgccagttc aagtataagt tccaattact    540
tgcattggta ccagcagaaa cctggccagg ctcccaggct cctcatctat aggacgtcca    600
atctggcttc tggcatccca gacaggttca gtggcagtgg gtctgggaca gacttcactc    660
tcaccatcag cagactggag cctgaagatt ttgcagtgta ttactgtcag cagggtagta    720
gtataccatt cacgtttggc caggggacca agctggagat caaacgtaag tggatcctat    780 cagggttta aagagggac taaagacatg tcagctatgt gtgactaatg gtaatgtcac     840
taagctgcgc gatcccgcaa ttctaaactc tgaggggtc ggatgacgtg gccattcttt    900
gcctaaagca ttgagtttac tgcaaggtca gaaaagcatg caaagccctc agaatggctg    960
caaagagctc caacaaaaca atttagaact ttattaagga atagggggaa gctaggaaga    1020
```

```
aactcaaaac atcaagattt taaatacgct tcttggtctc cttgctataa ttatctggga    1080
taagcatgct gttttctgtc tgtccctaac atgccctgtg attatccgca acaacacac     1140 ccaagggcag aactttgtta cttaaacacc atcctgtttg cttctttcct caggaactgt    1200
ggctgcacca tctgtcttca tcttcccgcc atctgatgag cagttgaaat ctggaactgc    1260
ctctgttgtg tgcctgctga ataacttcta tcccagagag gccaaagtac agtggaaggt    1320
ggataacgcc ctccaatcgg gtaactccca ggagagtgtc acagagcagg acagcaagga    1380
cagcacctac agcctcagca gcaccctgac gctgagcaaa gcagactacg agaaacacaa    1440
agtctacgcc tgcgaagtca cccatcaggg cctgagctcg cccgtcacaa agagcttcaa    1500
caggggagag tgttag                                                   1516

<210> SEQ ID NO 10
<211> LENGTH: 987
<212> TYPE: DNA
<213> ORGANISM: Artificial Sequence
<220> FEATURE:
<223> OTHER INFORMATION: HuIL12 p40 subunit

<400> SEQUENCE: 10
atgtgtcacc agcagttggt catctcttgg ttttcctgg ttttctggc atctcccctc       60 gtggccatat gggaactgaa gaaagatgtt tatgtcgtag aattggattg gtatccggat    120 gccctggag aaatggtggt cctcacctgt gacaccctg aagaagatgg tatcacctgg      180
accttggacc agagcagtga ggtcttaggc tctggcaaaa ccctgaccat ccaagtcaaa    240
gagtttggag atgctggcca gtacacctgt cacaaaggag gcgaggttct aagccattcg    300
ctcctgctgc ttcacaaaaa ggaagatgga atttggtcca ctgatatttt aaaggaccag    360
aaagaaccca aaaataagac cttttctaaga tgcgaggcca agaattattc tggacgtttc    420
acctgctggt ggctgacgac aatcagtact gatttgacat tcagtgtcaa agcagcaga    480 ggctcttctg accccccaagg ggtgacgtgc ggagctgcta cactctctgc agagagagtc    540
agaggggaca caaggagta tgagtactca gtggagtgcc aggaggacag tgcctgccca    600
gctgctgagg agagtctgcc cattgaggtc atggtggatg ccgttcacaa gctcaagtat    660
gaaaactaca ccagcagctt cttcatcagg gacatcatca acctgaccc acccaagaac    720 ttgcagctga agccattaaa gaattctcgg caggtggagg tcagctggga gtaccctgac    780
acctggagta ctccacattc ctacttctcc ctgacattct gcgttcaggt ccagggcaag    840
agcaagagag aaaagaaaga tagagtcttc acggacaaga cctcagccac ggtcatctgc    900
cgcaaaaatg ccagcattag cgtgcgggcc caggaccgct actatagctc atcttggagc    960
gaatgggcat ctgtgccctg cagttag                                       987

<210> SEQ ID NO 11
<211> LENGTH: 27
<212> TYPE: DNA
<213> ORGANISM: Artificial Sequence
<220> FEATURE:
<223> OTHER INFORMATION: Forward oligonucleotide primer for BC1 VL and
      vector pdH11

<400> SEQUENCE: 11
cttaagcgaa attgtgttga cgcagtc                                        27

<210> SEQ ID NO 12
<211> LENGTH: 30
<212> TYPE: DNA
```

```
<213> ORGANISM: Artificial Sequence
<220> FEATURE:
<223> OTHER INFORMATION: Reverse oligonucleotide primer for BC1 VL and
      vector pdH11

<400> SEQUENCE: 12
ggatccactt acgtttgatc tccagcttgg                                   30

<210> SEQ ID NO 13
<211> LENGTH: 17
<212> TYPE: DNA
<213> ORGANISM: Artificial Sequence
<220> FEATURE:
<223> OTHER INFORMATION: Mutated genomic signal peptide with Kozak
      Sequence

<400> SEQUENCE: 13
tctagaccac catggag                                                 17

<210> SEQ ID NO 14
<211> LENGTH: 27
<212> TYPE: DNA
<213> ORGANISM: Artificial Sequence
<220> FEATURE:
<223> OTHER INFORMATION: Forward oligonucleotide primer for VH of BC1
      and vector pdH11

<400> SEQUENCE: 14
cttaagcgag gtgcagctgg tgcagtc                                      27

<210> SEQ ID NO 15
<211> LENGTH: 29
<212> TYPE: DNA
<213> ORGANISM: Artificial Sequence
<220> FEATURE:
<223> OTHER INFORMATION: Reverse oligonucleotide primer for BC1 VH and
      pdH11

<400> SEQUENCE: 15
aagcttactt acctgaggag acggagacc                                    29

<210> SEQ ID NO 16
<211> LENGTH: 24
<212> TYPE: DNA
<213> ORGANISM: Artificial Sequence
<220> FEATURE:
<223> OTHER INFORMATION: XhoI-AflII fragment leader sequence

<400> SEQUENCE: 16
cctcgaggct agaccaccat ggag                                         24

<210> SEQ ID NO 17
<211> LENGTH: 10
<212> TYPE: DNA
<213> ORGANISM: Artificial Sequence
<220> FEATURE:
<223> OTHER INFORMATION: Mutated SmaI restriction site on DNA sequence
      encoding CH3 domain

<400> SEQUENCE: 17
cccgggtaaa                                                         10

<210> SEQ ID NO 18
<211> LENGTH: 21
<212> TYPE: DNA
<213> ORGANISM: Artificial Sequence
<220> FEATURE:
<223> OTHER INFORMATION: Sense oligonucleotide primer for p35 subunit
```

```
<400> SEQUENCE: 18
ccagaaagca agagaccaga g                                              21

<210> SEQ ID NO 19
<211> LENGTH: 31
<212> TYPE: DNA
<213> ORGANISM: Artificial Sequence
<220> FEATURE:
<223> OTHER INFORMATION: Antisense oligonucleotide primer for p35
      subunit

<400> SEQUENCE: 19
ggagggacct cgagttttag gaagcattca g                                   31

<210> SEQ ID NO 20
<211> LENGTH: 28
<212> TYPE: DNA
<213> ORGANISM: Artificial Sequence
<220> FEATURE:
<223> OTHER INFORMATION: Sense oligonucleotide primer for the p40
      subunit

<400> SEQUENCE: 20
ctccgtcctg tctagagcaa gatgtgtc                                       28

<210> SEQ ID NO 21
<211> LENGTH: 30
<212> TYPE: DNA
<213> ORGANISM: Artificial Sequence
<220> FEATURE:
<223> OTHER INFORMATION: Antisense oligonucleotide primer for the p40
      subunit

<400> SEQUENCE: 21
gcttctcgag aacctaactg cagggcacag                                     30

<210> SEQ ID NO 22
<211> LENGTH: 25
<212> TYPE: DNA
<213> ORGANISM: Artificial Sequence
<220> FEATURE:
<223> OTHER INFORMATION: Sense XmaI-BalI oligonucleotide linker

<400> SEQUENCE: 22
ccgggcgccg caaacctccc cgtgg                                          25

<210> SEQ ID NO 23
<211> LENGTH: 21
<212> TYPE: DNA
<213> ORGANISM: Artificial Sequence
<220> FEATURE:
<223> OTHER INFORMATION: Antisense XmaI-BalI oligonucleotide linker

<400> SEQUENCE: 23
ccacggggag gtttgcggcg c                                              21

<210> SEQ ID NO 24
<211> LENGTH: 6
<212> TYPE: DNA
<213> ORGANISM: Artificial Sequence
<220> FEATURE:
<223> OTHER INFORMATION: Alanine substitutions in sense XmaI-BalI
      oligonucloetide liker

<400> SEQUENCE: 24 gccgca                                                                6
```

```
<210> SEQ ID NO 25
<211> LENGTH: 12
<212> TYPE: PRT
<213> ORGANISM: Artificial Sequence
<220> FEATURE:
<223> OTHER INFORMATION: peptide sequence at CH3-p35 fusion junction

<400> SEQUENCE: 25

Leu Ser Leu Ser Pro Gly Ala Ala Asn Leu Pro Val
1               5                   10

<210> SEQ ID NO 26
<211> LENGTH: 4
<212> TYPE: PRT
<213> ORGANISM: Artificial Sequence
<220> FEATURE:
<223> OTHER INFORMATION: potential T helper cell epitope on peptide
      sequence at CH3-p35 fusion junction

<400> SEQUENCE: 26

Leu Ser Leu Ser
1

<210> SEQ ID NO 27
<211> LENGTH: 4
<212> TYPE: PRT
<213> ORGANISM: Artificial Sequence
<220> FEATURE:
<223> OTHER INFORMATION: Mutated potential T helper cell epitope on
      peptide sequence at CH3-p53 fusion junction

<400> SEQUENCE: 27

Ala Thr Ala Thr
1

<210> SEQ ID NO 28
<211> LENGTH: 287
<212> TYPE: PRT
<213> ORGANISM: Homo sapiens

<400> SEQUENCE: 28

Met Arg Gly Ser Val Val Thr Pro Leu Ser Pro Pro Thr Asn Leu His
1               5                   10                  15

Leu Glu Ala Asn Pro Asp Thr Gly Val Leu Thr Val Ser Trp Glu Arg
                20                  25                  30

Ser Thr Thr Pro Asp Ile Thr Gly Tyr Arg Ile Thr Thr Thr Pro Thr
            35                  40                  45

Asn Gly Gln Gln Gly Asn Ser Leu Glu Glu Val Val His Ala Asp Gln
        50                  55                  60

Ser Ser Cys Thr Phe Asp Asn Leu Ser Pro Gly Leu Glu Tyr Asn Val
65                  70                  75                  80

Ser Val Tyr Thr Val Lys Asp Asp Lys Glu Ser Val Pro Ile Ser Asp
                85                  90                  95

Thr Ile Ile Pro Ala Val Pro Pro Thr Asp Leu Arg Phe Thr Asn
            100                 105                 110

Ile Gly Pro Asp Thr Met Arg Val Thr Trp Ala Pro Pro Pro Ser Ile
        115                 120                 125

Asp Leu Thr Asn Phe Leu Val Arg Tyr Ser Pro Val Lys Asn Glu Glu
    130                 135                 140

Asp Val Ala Glu Leu Ser Ile Ser Pro Ser Asp Asn Ala Val Val Leu
145                 150                 155                 160
```

```
Thr Asn Leu Leu Pro Gly Thr Glu Tyr Val Val Ser Val Ser Ser Val
            165                 170                 175

Tyr Glu Gln His Glu Ser Thr Pro Leu Arg Gly Arg Gln Lys Thr Gly
        180                 185                 190

Leu Asp Ser Pro Thr Gly Ile Asp Phe Ser Asp Ile Thr Ala Asn Ser
        195                 200                 205

Phe Thr Val His Trp Ile Ala Pro Arg Ala Thr Ile Thr Gly Tyr Arg
210                 215                 220

Ile Arg His His Pro Glu His Phe Ser Gly Arg Pro Arg Glu Asp Arg
225                 230                 235                 240

Val Pro His Ser Arg Asn Ser Ile Thr Leu Thr Asn Leu Thr Pro Gly
                245                 250                 255

Thr Glu Tyr Val Val Ser Ile Val Ala Leu Asn Gly Arg Glu Glu Ser
            260                 265                 270

Pro Leu Leu Ile Gly Arg Ser Arg Ser His His His His His
            275                 280                 285
```

<210> SEQ ID NO 29
<211> LENGTH: 18
<212> TYPE: DNA
<213> ORGANISM: Artificial Sequence
<220> FEATURE:
<223> OTHER INFORMATION: Qiagen promoter primer

<400> SEQUENCE: 29
cccgaaaagt gccacctg                                                18

<210> SEQ ID NO 30
<211> LENGTH: 19
<212> TYPE: DNA
<213> ORGANISM: Artificial Sequence
<220> FEATURE:
<223> OTHER INFORMATION: Qiagen reverse primer sequence

<400> SEQUENCE: 30
gttctgaggt cattactgg                                               19

<210> SEQ ID NO 31
<211> LENGTH: 1126
<212> TYPE: DNA
<213> ORGANISM: Homo sapiens

<400> SEQUENCE: 31
ccccgaaaag tgccacctga cgtctaagaa accattatta tcatgacatt aacctataaa    60
aataggcgta tcacgaggcc ctttcgtctt cacctcgaga aatcataaaa aatttatttg   120
ctttgtgagc ggataacaat tataatagat tcaattgtga gcggataaca atttcacaca   180
gaattcatta aagaggagaa attaactatg agaggatctg tggtgacacc attgtctcca   240
ccaacaaact tgcatctgga ggcaaaccct gacactggag tgctcacagt ctcctgggag   300
aggagcacca ccccagacat tactggttat agaattacca caaccctac aaacggccag   360 cagggaaatt ctttggaaga agtggtccat gctgatcaga gctcctgcac ttttgataac   420
ctgagtcccg gcctggagta caatgtcagt gtttacactg tcaaggatga caaggaaagt   480
gtccctatct ctgataccat catcccagct gttcctcctc ccactgacct gcgattcacc   540
aacattggtc cagacaccat gcgtgtcacc tgggctccac cccatccat tgatttaacc   600 aacttcctgg tgcgttactc acctgtgaaa aatgaggaag atgttgcaga ttgtcaatt   660 tctccttcag acaatgcagt ggtcttaaca aatctcctgc ctggtacaga atatgtagtg   720

```
agtgtctcca gtgtctacga acaacatgag agcacacctc ttagaggaag acagaaaaca   780
ggtcttgatt ccccaactgg cattgacttt tctgatatta ctgccaactc ttttactgtg   840
cactggattg ctcctcgagc caccatcact ggctacagga tccgccatca tcccgagcac   900
ttcagtggga gacctcgaga agatcgggtg ccccactctc ggaattccat caccctcacc   960
aacctcactc caggcacaga gtatgtggtc agcatcgttg ctcttaatgg cagagaggaa  1020
agtcccttat tgattggcag atccagatct catcaccatc accatcacta agcttaatta  1080
gctgagcttg gactcctgtt gatagatcca gtaatgacct cagaac                 1126
```

<210> SEQ ID NO 32
<211> LENGTH: 378
<212> TYPE: PRT
<213> ORGANISM: Homo sapiens

<400> SEQUENCE: 32

```
Met Arg Gly Ser Val Val Thr Pro Leu Ser Pro Thr Asn Leu His
1               5                   10                  15

Leu Glu Ala Asn Pro Asp Thr Gly Val Leu Thr Val Ser Trp Glu Arg
                20                  25                  30

Ser Thr Thr Pro Asp Ile Thr Gly Tyr Arg Ile Thr Thr Pro Thr
            35                  40                  45

Asn Gly Gln Gln Gly Asn Ser Leu Glu Glu Val Val His Ala Asp Gln
 50                  55                  60

Ser Ser Cys Thr Phe Asp Asn Leu Ser Pro Gly Leu Glu Tyr Asn Val
65                  70                  75                  80

Ser Val Tyr Thr Val Lys Asp Asp Lys Glu Ser Val Pro Ile Ser Asp
                85                  90                  95

Thr Ile Ile Pro Glu Val Pro Gln Leu Thr Asp Leu Ser Phe Val Asp
            100                 105                 110

Ile Thr Asp Ser Ser Ile Gly Leu Arg Trp Thr Pro Leu Asn Ser Ser
        115                 120                 125

Thr Ile Ile Gly Tyr Arg Ile Thr Val Val Ala Ala Gly Glu Gly Ile
130                 135                 140

Pro Ile Phe Glu Asp Phe Val Asp Ser Ser Val Gly Tyr Tyr Thr Val
145                 150                 155                 160

Thr Gly Leu Glu Pro Gly Ile Asp Tyr Asp Ile Ser Val Ile Thr Leu
                165                 170                 175

Ile Asn Gly Gly Glu Ser Ala Pro Thr Thr Leu Thr Gln Gln Thr Ala
            180                 185                 190

Val Pro Pro Pro Thr Asp Leu Arg Phe Thr Asn Ile Gly Pro Asp Thr
        195                 200                 205

Met Arg Val Thr Trp Ala Pro Pro Ser Ile Asp Leu Thr Asn Phe
210                 215                 220

Leu Val Arg Tyr Ser Pro Val Lys Asn Glu Glu Asp Val Ala Glu Leu
225                 230                 235                 240

Ser Ile Ser Pro Ser Asp Asn Ala Val Val Leu Thr Asn Leu Leu Pro
                245                 250                 255

Gly Thr Glu Tyr Val Val Ser Val Ser Ser Val Tyr Glu Gln His Glu
            260                 265                 270

Ser Thr Pro Leu Arg Gly Arg Gln Lys Thr Gly Leu Asp Ser Pro Thr
        275                 280                 285

Gly Ile Asp Phe Ser Asp Ile Thr Ala Asn Ser Phe Thr Val His Trp
290                 295                 300
```

```
Ile Ala Pro Arg Ala Thr Ile Thr Gly Tyr Arg Ile Arg His His Pro
305                 310                 315                 320

Glu His Phe Ser Gly Arg Pro Arg Glu Asp Arg Val Pro His Ser Arg
                325                 330                 335

Asn Ser Ile Thr Leu Thr Asn Leu Thr Pro Gly Thr Glu Tyr Val Val
            340                 345                 350

Ser Ile Val Ala Leu Asn Gly Arg Glu Glu Ser Pro Leu Leu Ile Gly
        355                 360                 365

Arg Ser Arg Ser His His His His His His
    370                 375

<210> SEQ ID NO 33
<211> LENGTH: 1399
<212> TYPE: DNA
<213> ORGANISM: Homo sapiens

<400> SEQUENCE: 33
ccccgaaaag tgccacctga cgtctaagaa accattatta tcatgacatt aacctataaa    60
aataggcgta tcacgaggcc ctttcgtctt cacctcgaga atcataaaa aatttatttg    120 ctttgtgagc ggataacaat tataatagat tcaattgtga gcggataaca atttcacaca    180
gaattcatta agaggagaa attaactatg agaggatctg tggtgacacc attgtctcca    240
ccaacaaact tgcatctgga ggcaaaccct gacactggag tgctcacagt ctcctgggag    300
aggagcacca ccccagacat tactggttat agaattacca caaccccctac aaacggccag    360 cagggaaatt ctttggaaga agtggtccat gctgatcaga gctcctgcac ttttgataac    420
ctgagtcccg gcctggagta caatgtcagt gtttacactg tcaaggatga caaggaaagt    480
gtccctatct ctgataccat catcccagag gtgccccaac tcactgacct aagctttgtt    540
gatataaccg attcaagcat cggcctgagg tggaccccgc taaactcttc caccattatt    600
gggtaccgca tcacagtagt tgcggcagga gaaggtatcc ctatttttga agattttgtg    660
gactcctcag taggatacta cacagtcaca gggctggagc cgggcattga ctatgatatc    720
agcgttatca ctctcattaa tggcggcgag agtgccccta ctacactgac acaacaaacg    780
gctgttcctc ctcccactga cctgcgattc accaacattg tccagacac catgcgtgtc    840 acctgggctc caccccatc cattgattta accaacttcc tggtgcgtta ctcacctgtg    900
aaaaatgagg aagatgttgc agagttgtca atttctcctt cagacaatgc agtggtctta    960
acaaatctcc tgcctggtac agaatatgta gtgagtgtct ccagtgtcta cgaacaacat    1020
gagagcacac tcttagagg aagacagaaa acaggtcttg attccccaac tggcattgac    1080
ttttctgata ttactgccaa ctctttact gtgcactgga ttgctcctcg agccaccatc    1140
actggctaca ggatccgcca tcatcccgag cacttcagtg ggagacctcg agaagatcgg    1200
gtgccccact ctcggaattc catcaccctc accaacctca ctccaggcac agagtatgtg    1260
gtcagcatcg ttgctcttaa tggcagagag gaaagtccct tattgattgg cagatccaga    1320
tctcatcacc atcaccatca ctaagcttaa ttagctgagc ttggactcct gttgatagat    1380
ccagtaatga cctcagaac                                                1399
```